US010736558B2

(12) United States Patent
Omari et al.

(10) Patent No.: US 10,736,558 B2
(45) Date of Patent: Aug. 11, 2020

(54) METHODS FOR ASSESSING SWALLOWING MOTOR FUNCTION

(71) Applicants: Taher Imad Omari, North Adelaide (AU); Nathalie Rommel, Leuven (BE)

(72) Inventors: Taher Imad Omari, North Adelaide (AU); Nathalie Rommel, Leuven (BE)

(*) Notice: Subject to any disclaimer, the term of this patent is extended or adjusted under 35 U.S.C. 154(b) by 515 days.

(21) Appl. No.: 15/488,079

(22) Filed: Apr. 14, 2017

(65) Prior Publication Data

US 2018/0000402 A1    Jan. 4, 2018

Related U.S. Application Data

(63) Continuation of application No. 13/823,072, filed as application No. PCT/AU2011/001174 on Sep. 13, 2011, now abandoned.

(30) Foreign Application Priority Data

Sep. 13, 2010 (AU) .............................. 2010/904104
Jun. 16, 2011 (AU) .............................. 2011/902359

(51) Int. Cl.
  *A61B 5/00* (2006.01)
  *A61B 5/03* (2006.01)
  (Continued)

(52) U.S. Cl.
  CPC ............ *A61B 5/4205* (2013.01); *A61B 5/036* (2013.01); *A61B 5/037* (2013.01); *A61B 5/0538* (2013.01);
  (Continued)

(58) Field of Classification Search
  CPC ....... A61B 5/0538; A61B 5/036; A61B 5/037; A61B 5/038; A61B 5/7235; A61B 5/7246; A61B 5/7275; A61B 5/7282
  See application file for complete search history.

(56) References Cited

U.S. PATENT DOCUMENTS

| 7,236,820 B2 | 6/2007 | Mabary et al. |
| 2005/0065450 A1* | 3/2005 | Stuebe .................. A61B 5/037 600/547 |

(Continued)

OTHER PUBLICATIONS

International Search Report and Written Opinion dated Sep. 13, 2011 for PCT/AU2011/001174.
(Continued)

*Primary Examiner* — Lynsey C Eiseman
*Assistant Examiner* — Amanda L Steinberg
(74) *Attorney, Agent, or Firm* — McAfee & Taft

(57) ABSTRACT

The present invention relates to methods for assessing swallowing motor function in a subject. The methods rely on obtaining intraluminal impedance and pressure measurements from the pharynx and/or esophagus of the subject during clearance of a bolus from the mouth and/or throat of the subject. The intraluminal impedance and pressure measurements are combined to derive a value for one or more pressure-flow variables in the pharynx and/or the esophagus of the subject. The value of the one or more pressure-flow variables is compared to a predetermined pharyngeal and/or esophageal reference value for the one or more pressure-flow variables in order to provide an assessment of swallowing motor function in the subject. The intraluminal impedance and pressure measurements can also be combined to generate a swallow risk index for the subject or to generate an obstructive risk index for the subject based on a combination of a value of more than one pressure-flow variable in the pharynx and/or esophagus of the subject. In this way, swallowing motor function in the subject can be assessed by comparing the swallow risk index or obstructive risk index for the subject to a predetermined reference swallow index or predetermined reference obstructive index, respectively. Products which make use of these methods are also encompassed by the present invention.

11 Claims, 31 Drawing Sheets
(7 of 31 Drawing Sheet(s) Filed in Color)

(51) Int. Cl.
    *A61B 5/053*    (2006.01)
    *G16H 50/30*    (2018.01)
    *G16H 50/20*    (2018.01)
    *G16H 40/63*    (2018.01)
    *G16H 20/40*    (2018.01)

(52) U.S. Cl.
    CPC .......... *A61B 5/7235* (2013.01); *A61B 5/7275* (2013.01); *A61B 5/7282* (2013.01); *G16H 40/63* (2018.01); *G16H 50/20* (2018.01); *G16H 50/30* (2018.01); *G16H 20/40* (2018.01)

(56) References Cited

U.S. PATENT DOCUMENTS

2006/0116564 A1* 6/2006 Mintchev ............... A61B 5/037
                                                    600/350
2007/0225613 A1* 9/2007 Mabary ................. A61B 5/037
                                                    600/547

OTHER PUBLICATIONS

Supplemental European Search Report and Written Opinion dated Sep. 13, 2011 for Application No. EP 11824347.
A Method to Objectively Assess Swallowing Function in Adults With Suspected Aspiration, Taher I. Omari et al. Gastroenterology 2011; 140:1454-1463.
A Novel Method for the Nonradiological Assessment of Ineffective Swallowing, Taher I Omari et al., The American Journal of Gastroenterology, vol. 106, Oct. 2011.

\* cited by examiner

FIGURE 2
A
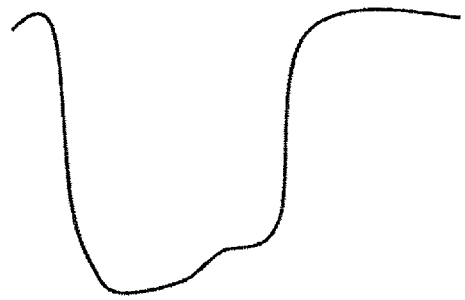
B
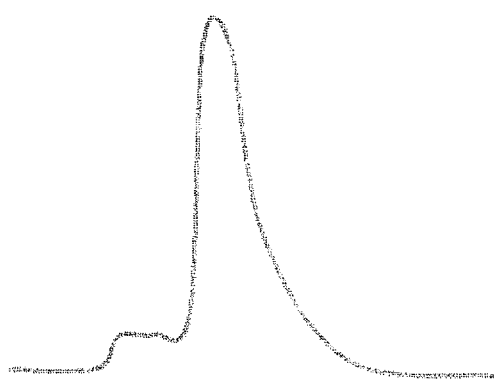
C
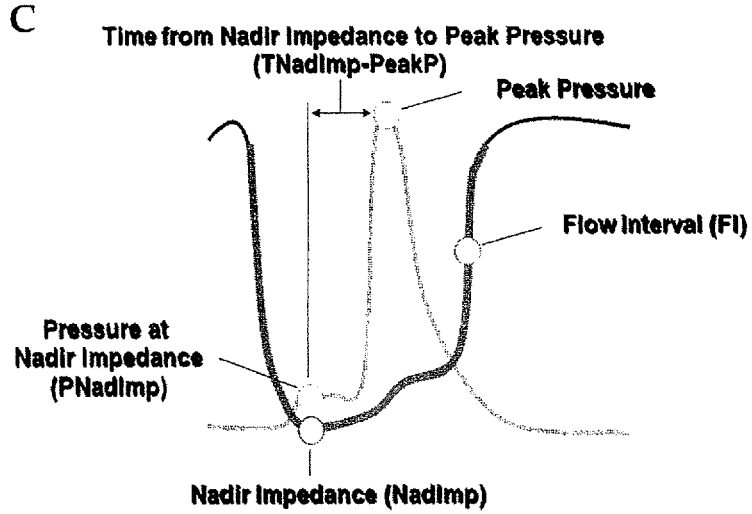

FIGURE 11
A.
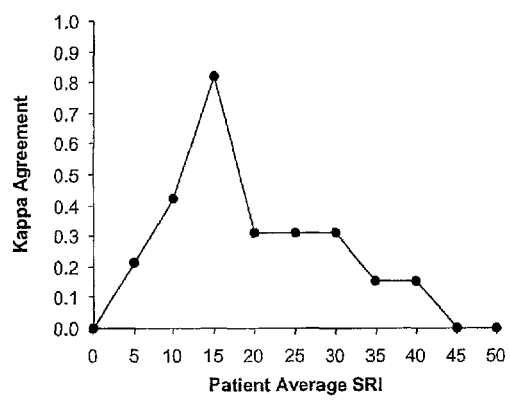
B.
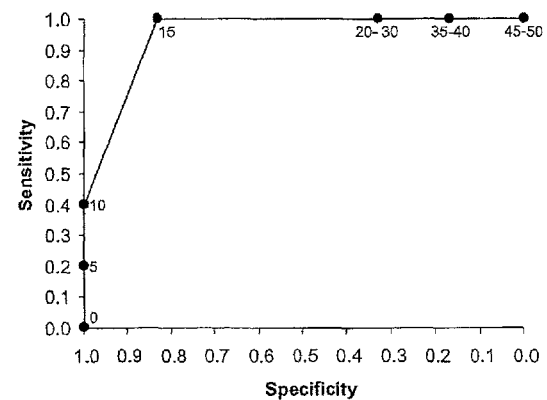

FIGURE 20
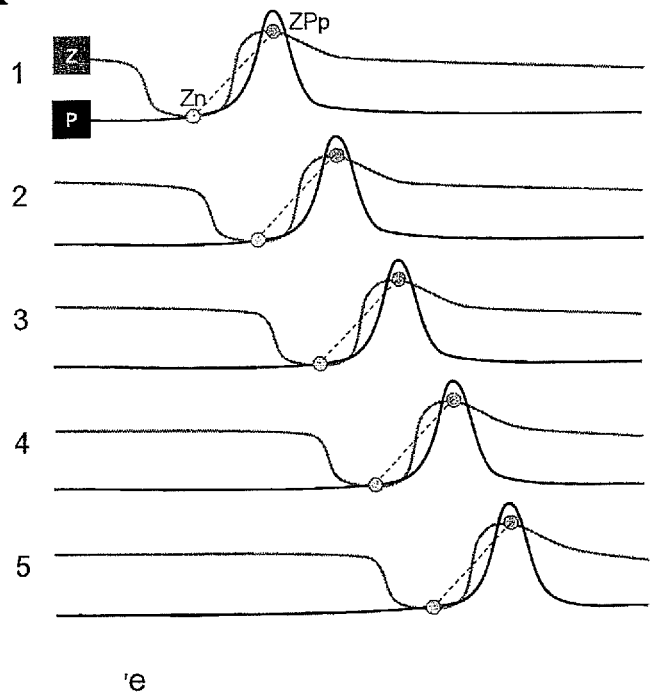
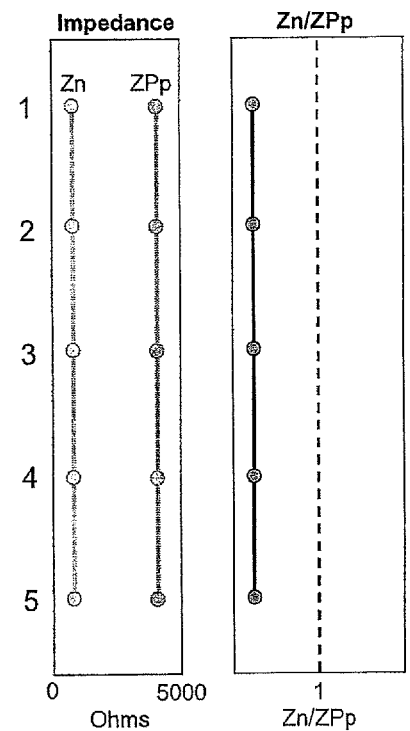
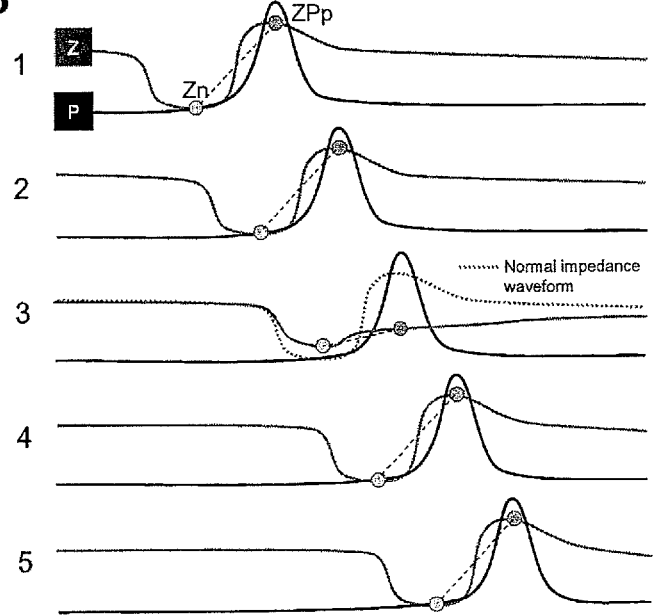
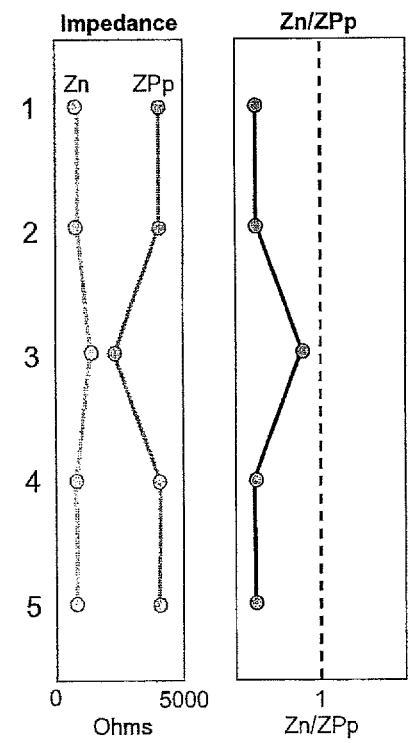

FIGURE 27

TABLE 3

|  |  | CONTROLS | | | PATIENTS | | |
| --- | --- | --- | --- | --- | --- | --- | --- |
|  |  | All Swallows | WITHOUT Residue | WITH Residue (p vs NO Residue) | All Swallows (p vs Control) | WITHOUT Residue | WITH Residue (p vs NO Residue) |
| No. Sw Total (first/cleaning) |  | 39 (18f/21c) | 27 (11f/16c) | 12 (7f/5c) | 76 (37f/39c) | 41 (20f/21c) | 35 (17f/18c) |
| UES Relaxation Interval msec | First Sw | 422 [348, 497] | 425 [323, 570] | 402 [39, 775] | 786 (0.001) [323, 1114] | 64 [381, 938] | 921 [561, 1201] |
|  | Cleaning Sw | 350 [286, 475] | 350 [302, 487] | 349 [13, 532] | 670 (<0.001) [463, 1138] | 489 (2.94, 721] | 1136 (<0.001) [784, 1480] |
|  | All Sw | 402 [325, 513] | 403 [325, 513] | 390 [275, 589] | 710 (<0.001) [464, 1144] | 540 [325, 884] | 1021 (<0.001) [638, 1224] |
| UES Intrabolus Pressure mmHg | First Sw | 30 [20, 48] | 24 [20, 40] | 35 [16, 55] | 16 (0.002) [8, 24] | 18 [11, 27] | 15 [7, 22] |
|  | Cleaning Sw | 7 [4, 37] | 6 [3, 22] | 37 [10, 42] | 17 [12, 24] | 17 [12, 24] | 16 [8, 28] |
|  | All Sw | 21 [7, 38] | 20 [8, 35] | 30 (0.065) [8, 45] | 16 [8, 24] | 17 [12, 24] | 15 [7, 24] |
| Nadir UES Pressure mmHg | First Sw | 15 [3, 33] | 4 [0, 33] | 15 [3, 36] | 5 [0, 12] | 10 [2, 16] | 2 (0.072) [0, 10] |
|  | Cleaning Sw | 2 [-1, 20] | 2 [1, 5] | 31 (0.036) [2, 38] | 9 [1, 16] | 13 [2, 18] | 9 [2, 13] |
|  | All Sw | 4 [0, 25] | 3 [1, 10] | 18 (0.035) [4, 36] | 25 (<0.001) [0, 30] | 12 [2, 19] | 3 (0.023) [0, 11] |
| UES resistance mmHg/sec | First Sw | 52 [29, 98] | 48 [29, 77] | 57 [39, 157] | 22 [10, 52] | 29 [22, 44] | 18 (0.035) [10, 29] |
|  | Cleaning Sw | 17 [12, 103] | 15 [10, 54] | 108 (0.091) [18, 204] |  | 36 [19, 64] | 16 (0.005) [8, 22] |
|  | All Sw | 42 [16, 100] | 30 [14, 59] | 77 (0.051) [26, 169] | 22 (0.004) [12, 38] | 30 [19, 53] | 16 (<0.001) [6, 23] |

TABLE 4

FIGURE 28

| Variable | All Patients | | Results Before Surgery vs Dysphagia Before Surgery | | Results Before Surgery vs Dysphagia After Surgery | | Results After Surgery vs Dysphagia After Surgery | |
|---|---|---|---|---|---|---|---|---|
| | Pre-Op | Post-Op | No Dysphagia Pre-Op | Dysphagia Pre-Op | No Dysphagia Post-Op | Dysphagia Post-Op | No Dysphagia | Dysphagia After Surgery |
| Esophageal | | | | | | | | |
| Peak P mmHg | 46 ±3 | 40 ±4 | 50 ±3 | 45 ±6 | 45 ±3 | 46 ±4 | 66 ±5 | 44 ±4 |
| Distal Peak P mmHg | 44 ±4 | 56 (0.069) ±6 | 45 [40,61] | 29 (0.037) [23,48] | 43 ±4 | 44 ±5 | 74 ±17 | 50 ±6 |
| PNadimp mmHg | 12 [7,22] | 12 [2,18] | 12 ±2 | 16 ±3 | 10 ±2 | 15 ±2 | 6 [3,11] | 15 (0.086) [8,17] |
| Distal PNadimp mmHg | 5 [4,9] | 9 [3,23] | 6 [4,12] | 4 [4,8] | 5 [1,6] | 5 [4,12] | 5 ±2 | 15 ±4 |
| IBP mmHg | 17 ±2 | 17 ±2 | 15 ±3 | 19 ±3 | 10 ±2 | 19 (0.042) ±2 | 10 ±2 | 18 ±3 |
| Distal IBP mmHg | 10 ±2 | 10 ±3 | 10 ±3 | 10 ±3 | 3 [2,7] | 8 (0.100) [5,16] | 9 ±2 | 18 ±4 |
| IBP Slope mmHg/sec | 9 ±2 | 9 ±2 | 7 [5,10] | 4 [3,23] | 5 [0,7] | 7 [4,18] | 9 [5,18] | 7 [8,13] |
| Distal IBP Slope mmHg/sec | 7 ±1 | 10 ±2 | 7 ±2 | 8 ±2 | 2 ±1 | 9 (0.047) ±2 | 8 ±2 | 10 ±2 |
| TNadimp-PeakP sec | 2.0 ±0.2 | 1.8 ±0.2 | 2.1 ±0.3 | 1.9 ±0.4 | 2.7 ±0.2 | 1.8 (0.080) ±0.2 | 2.6 ±0.7 | 1.6 (0.099) ±0.2 |
| Dist. TNadimp-PeakP sec | 2.8 ±0.3 | 2.4 ±0.3 | 2.9 ±0.4 | 2.7 ±0.4 | 4.0 ±0.3 | 2.5 (0.020) ±0.3 | 3.2 ±0.7 | 2.1 ±0.3 |
| Dysphagia Risk Index | 23 [14,95] | 33 [2,325] | 22 [11,172] | 40 [16,97] | 9 [-2,19] | 43 (0.017) [20,177] | 33 [8,61] | 32 [2,379] |
| EGJ | Pre-Op | Post-Op | No Dysphagia Pre-Op | Dysphagia Pre-Op | No Dysphagia Post-Op | Dysphagia Post-Op | No Dysphagia | Dysphagia Post-Op |
| Basal EGJ pressure mmHg | 7 [4,12] | 18 (0.017) [8,23] | 6 [3,10] | 8 [6,15] | 6 [2,10] | 7 [2,10] | 18 [8,29] | 15 [8,24] |
| Nadir EGJ pressure mmHg | -2 [-4,0] | 2 (0.016) [-2,10] | -3 ±1 | -1 ±1 | -2 ±2 | -2 ±1 | 3 [-2,8] | 2 [-2,11] |
| 4 sec IRP mmHg | 0 [-2,3] | 6 (0.009) [-1,14] | -1 ±1 | 1 ±1 | -1 ±2 | 1 ±1 | 6 [0,11] | 6 [0,15] |

TABLE 5

FIGURE 29

| | NO Dysphagia Sx Before or After Surgery | Dysphagia Sx Before and After Surgery | Dysphagia Sx After Surgery Only | ANOVA p |
|---|---|---|---|---|
| Before Surgery | | | | |
| Distal TNadImp-PeakP sec | 4.0 ±0.3 | 2.7 ±0.4 | 2.2* ±0.4 | 0.043 |
| Distal IBP Slope mmHg/sec | 2 ±1 | 7 ±2 | 10 ±3 | 0.089 |
| IBP mmHg | 10 ±2 | 19 ±3 | 18 ±4 | 0.133 |
| Dysphagia Risk Index | 9 [-2, 19] | 40 [16, 97] | 61* [22, 508] | 0.036 |
| After Surgery | | | | |
| Dist. TNadImp-PeakP sec | 3.2 ±0.7 | 2.0 ±0.4 | 2.2 ±0.6 | 0.346 |
| Dist. IBP Slope mmHg/sec | 8 ±2 | 12 ±3 | 8 ±3 | 0.613 |
| IBP mmHg | 10 [8, 13] | 18 [14, 22] | 14 [3, 29] | 0.129 |
| Dysphagia Risk Index | 34 ±14 | 370 ±202 | -119 ±272 | 0.267 |

TABLE 6

FIGURE 30

METHODS FOR ASSESSING SWALLOWING MOTOR FUNCTION

PRIORITY CLAIM

This international patent application claims priority to Australian provisional patent application 2010904104 filed on 13 Sep. 2010, and to Australian provisional patent application 2011902359 filed on 16 Jun. 2011, and U.S. patent application Ser. No. 13/823,072 filed on 17 May 2013, the contents of which are herein incorporated by reference.

FIELD OF THE INVENTION

The present invention relates generally to methods for assessing pharyngeal and/or esophageal motor function in a subject during swallowing. The methods may be used to identify ineffective swallowing in the subject, including ineffective swallowing due to an obstruction, and may further be used to determine risk of aspiration in the subject.

BACKGROUND OF THE INVENTION

Swallowing is a complex process which involves a number of interdependent and coordinated phases. Generally, these include the preparatory, oral, pharyngeal and esophageal phases indicative of the anatomic regions traversed by a swallowed food and/or liquid bolus. During the preparatory phase, a food bolus for example remains in the mouth while it undergoes physical and some chemical changes which make it suitable for transit through the aerodigestive tract. During the oral phase, the bolus is propelled from the mouth into the pharynx by a peristaltic pressure wave generated by sequential squeezing of the tongue against the hard and soft palates. During the pharyngeal phase, the upper esophageal sphincter opens and the bolus is transported into the esophagus by a combination of peristaltic contraction of the pharyngeal constrictors and tongue movement continued from the oral phase. Finally, during the esophageal phase of swallowing, the bolus is transported further into the esophagus and stomach for digestion.

The portion of the swallowing process encompassing the oral to pharyngeal phases is often referred to as oropharyngeal swallowing. Oropharyngeal swallowing begins with closure of the vocal cords, signifying the activation of airway protection, and ends when the vocal cords return to their resting state. Indeed during this time, respiration is reflexively inhibited. Therefore, oropharyngeal swallowing serves two functions, namely transit of the bolus and protection of the airway, in which both functions are highly coordinated.

Due to the complex nature of the swallowing process, pharyngeal and esophageal motor function must operate effectively and in a coordinated manner for a successful swallow to occur. When motor function is compromised, difficulty in swallowing (dysphagia) arises and an ineffective swallow ensues.

Dysphagia is most commonly a consequence of a disease, disorder or condition which impairs coordination, or weakens swallowing biomechanics. For example, dysphagia is often associated with acute events, such as stroke, brain injury, and head and neck cancers, or arises as a result of surgery associated with such cancers. In addition, radiotherapy and chemotherapy associated with cancer treatment tends to weaken the muscles and degrade the nerves associated with the physiology and nervous innervation of the swallow reflex. It is also common for individuals with progressive neuromuscular diseases, such as muscular dystrophy and myasthenia gravis, to experience increasing difficulty in swallowing initiation. Dysphagia is also associated neurological conditions (such as cerebral palsy, Guillain-Barre syndrome, Huntington's disease, multiple sclerosis, Parkinson's disease, and dementia), infectious illnesses, autoimmune illnesses, metabolic illnesses, myopathic illnesses, iatrogenic illnesses, and structural illnesses. Accordingly, dysphagia is generally considered an interdisciplinary phenomenon.

Dysphagia is often accompanied by aspiration due to ineffective airway protection during oropharyngeal swallowing. In effect, food particles, oral secretions and/or stomach contents become misdirected into the larynx and pass into the lungs. Pulmonary aspiration due to swallowing dysfunction (deglutitive aspiration) is the major reason for modification of feeding strategies (e.g. oral to tube feeding, avoidance of liquids etc) which can significantly impact on the quality of life of affected subjects. Furthermore, aspiration can lead to recurrent pneumonia, progressive lung disease, and respiratory disability. Therefore aspiration is a serious condition which can, if undetected, result in severe complications and potentially death. Accordingly, dysphagia and pulmonary aspiration represent significant clinical, social, and economic costs and issues. For example, epidemiological studies estimate a prevalence rate for dysphagia of 16% to 22% among individuals over the age of 50. In addition, dysphagia is extremely common in the paediatric population within a wide range of disorders. This hinders the provision of adequate nutrition, affecting growth and development leading to significant parental anxiety and family disruption. Indeed, in the United States approximately 800,000 individuals per year are affected by dysphagia that is a consequence of neurological disorders, and stroke survivors alone can account for about 100,000 cases of aspiration.

Despite the significantly high prevalence of swallowing disorders and associated complications, the current methods for the assessment of swallowing and for the evaluation of direct aspiration are far from optimal. For example, manometry has been used to assess pharyngo-esophageal motor function in a variety of pathologies that cause pharyngeal weakness or impaired upperesophageal sphincter (UES) relaxation. Such disorders lead to ineffective pharyngeal bolus clearance and/or aspiration. The manometric technologies used for this assessment have evolved from single point sensors, to movement-tolerant sleeve sensors and, most recently, high resolution manometry which incorporates multiple closely spaced solid state point sensors. These manometric methods have been utilised to describe the alterations in pressure patterns in relation to well recognized causes of aspiration. These include age-related changes, neurodegenerative disease, post-surgical dysfunctions, and abnormalities of the UES opening due to various factors. The use of manometry for assessment of aspiration risk has been very limited in routine clinical practice. This is because manometric criteria alone have not been shown to accurately assess risk of aspiration and/or post-swallow bolus residue.

Although intraluminal impedance measurement has emerged in recent years as a technique that can be used to detect failed esophageal bolus transport, the application of impedance measurement to examine pharynx motor function has proven extremely challenging. Pharyngeal swallow events occur over a much shorter time span than esophageal peristalsis and several factors cause large variations of the baseline level of impedance, such as variable mucosal contact, residue and secretions. These factors cause impedance signals to be much more noisy in the pharynx than in the esophagus, so that attempts to optimize criteria that identify aberrant bolus flow events and residue have only been partially successful.

Fluoroscopic observation of pharyngo-esophageal bolus transit is the standard tool for evaluation of swallowing function and direct aspiration. The limitations of fluoroscopy are however well known, the most important being prolonged exposure to radiation and the qualitative nature of the test, because it is not possible to derive robust numerical measures. Accordingly it is not appropriate for patient screening. As a result, subjects who are potentially at risk of aspiration are often not referred for fluoroscopy until they have deteriorated clinically and present with weight loss, eating difficulties, recurrent respiratory infections or aspiration pneumonia. Whilst fluoroscopy can identify a point of narrowing of the lumen (such as a stricture, ring or web) that may be impeding normal flow of the bolus, in many patients the test fails to identify any obvious abnormality and these patient are often defined as suffering from non-obstructive dysphagia. Furthermore, even if used for patient screening, there is clear evidence that fluoroscopy is poorly predictive of progression to aspiration pneumonia, and due to limits on investigation time, a normal fluoroscopy cannot entirely guarantee the absence of feed aspiration.

Indeed, at present there is no method that is sensitive for identification of subjects at high risk for deglutitive aspiration at a time when aspiration-associated complications might be prevented by intervention. Even observed clinical signs and symptoms (such as wet voice, wet breathing, and cough) have only a 33-67% sensitivity to predict aspiration of liquids on fluoroscopy. Furthermore, fluoroscopy-based parameters, such as pharyngeal residue, are relatively poor markers of aspiration.

On the basis of the aforementioned inadequacies of existing techniques, there is a substantial interest in developing new and effective methods which enable an assessment of swallowing function in individuals, so as to identify those individuals with ineffective swallowing (for example due to a functional abnormality causing an obstruction), and who are therefore at risk of aspiration.

Reference to any prior art in this specification is not, and should not be taken as, an acknowledgment or any form of suggestion that this prior art forms part of the common general knowledge in any country.

SUMMARY OF THE INVENTION

The present invention is predicated in part on the finding that manometry and impedance data obtained from a subject during swallowing can, when combined, provide valuable markers for the assessment of swallowing motor function in a subject.

Accordingly, in a first aspect the present invention provides a method for assessing swallowing motor function in a subject, the method including:
 (a) accessing intraluminal impedance measurements and pressure measurements obtained from the pharynx and/or esophagus of the subject during clearance of a bolus from the mouth and/or throat of the subject;
 (b) combining and analysing the intraluminal impedance and pressure measurements to derive a value for one or more pressure-flow variables in the pharynx and/or esophagus of the subject; and
 (c) assessing swallowing motor function in the subject by comparing the value of the one or more pressure-flow variables with a predetermined pharyngeal and/or esophageal reference value for the one or more pressure-flow variables.

In one embodiment, the subject is suspected to have dysphagia.

In some embodiments, the method is used to identify ineffective swallowing in the subject. In some embodiments, the method is used to determine risk of aspiration in the subject, diagnose an increased likelihood of aspiration in the subject, predict aspiration in the subject, and/or identify a subject susceptible to aspiration.

In some embodiments, the intraluminal impedance measurements are used to generate an impedance waveform of the bolus clearance.

In some embodiments, the pressure measurements are used to generate a pressure waveform of the bolus clearance.

In some embodiments, the intraluminal impedance measurements are used to guide analysis of the pressure measurements. For example, in one embodiment, combining and analysing the intraluminal impedance and pressure measurements includes measuring the nadir of the impedance waveform, and wherein the nadir of the impedance waveform is used as a time marker for analysis of the pressure waveform.

In one embodiment, one of the pressure-flow variables is the pressure at the nadir of the impedance waveform (PNadImp) in the pharynx and/or esophagus of the subject. In one embodiment, a higher PNadImp in the subject compared to the predetermined pharyngeal and/or esophageal PNadImp reference value is indicative of ineffective swallowing and/or risk of aspiration in the subject. In one embodiment, the predetermined pharyngeal PNadImp reference value is about 26 mmHg.

In some embodiments, one of the pressure-flow variables is the peak pressure of the pressure waveform (PeakP) in the pharynx and/or esophagus of the subject. In one embodiment, a lower PeakP in the subject compared to the predetermined pharyngeal and/or esophageal PeakP reference value is indicative of ineffective swallowing and/or risk of aspiration in the subject. In one embodiment, the predetermined pharyngeal PeakP reference value is about 93 mmHg.

In some embodiments, one of the pressure-flow variables is the time from the nadir of the impedance waveform to the peak pressure (TNadImp-PeakP) in the pharynx and/or esophagus of the subject. In one embodiment, a shorter TNadImp-PeakP in the subject compared to the predetermined pharyngeal and/or esophageal TNadImp-PeakP reference value is indicative of ineffective swallowing and/or risk of aspiration in the subject. In one embodiment, the predetermined pharyngeal TNadImp-PeakP reference value is about 371 msec.

In some embodiments, one of the pressure-flow variables is the duration of the drop in intraluminal impedance during bolus clearance (Flow Interval) in the pharynx and/or esophagus of the subject. In one embodiment, a longer Flow Interval in the subject compared to the predetermined pharyngeal and/or esophageal Flow Interval reference value is indicative of ineffective swallowing and/or risk of aspiration in the subject. In one embodiment, the predetermined pharyngeal Flow Interval reference value is about 1249 msec.

In some embodiments, the value of more than one pressure-flow variable is combined to generate a swallow risk index in the subject. In one embodiment, the swallow risk index has the following formula:

$$\frac{(\text{Flow Interval} \times PNadImp)}{(PeakP \times (PNadImp - PeakP + 1))} \times 100$$

In some embodiments, a swallow risk index which is higher than a predetermined reference swallow index is indicative of an ineffective swallow and/or a risk of aspiration in the subject. In one embodiment, the predetermined reference swallow index is 9, and a subject with a swallow risk index of about 10 or higher has an ineffective swallow. In another embodiment, the predetermined reference swallow index is 15, and a subject with a swallow risk index of about 16 or higher has an ineffective swallow and/or risk of aspiration.

In some embodiments of the first aspect of the invention, the method is used to predict the occurrence of dysphagia in the subject following therapy and/or surgery. In one embodiment, one of the pressure flow variables is intrabolus pressure (IBP) in the pharynx and/or esophagus of the subject. In one embodiment, a higher IBP in the subject compared to the predetermined pharyngeal and/or esophageal IBP reference value is a predictor for the occurrence of dysphagia in the subject following therapy and/or surgery. In one embodiment, the predetermined esophageal IBP reference value is about 12 mmHg.

In some embodiments, one of the pressure flow variables is intrabolus pressure slope (IBP Slope) in the pharynx and/or esophagus of the subject. In one embodiment, an elevated IBP Slope in the subject compared to the predetermined pharyngeal and/or esophageal IBP Slope reference value is a predictor for the occurrence of dysphagia in the subject following therapy and/or surgery. In one embodiment, the predetermined esophageal IBP Slope reference value is about 5 mmHg/sec.

In some embodiments, one of the pressure flow variables is time from the nadir of the impedance waveform to the peak pressure (TNadImp-PeakP) in the pharynx and/or esophagus of the subject. In one embodiment, a shorter TNadImp-PeakP in the subject compared to the predetermined pharyngeal and/or esophageal TNadImp-PeakP reference value is a predictor for the occurrence of dysphagia in the subject following therapy and/or surgery. In one embodiment, the predetermined esophageal TNadImp-PeakP reference value is about 3.5 sec.

In some embodiments, the value of more than one pressure-flow variable is combined to generate a dysphagia risk index in the subject. In one embodiment, the dysphagia risk index has the following formula:

$$IBP \times IBP\ Slope \times TNadImp\text{-}PeakP^{-1}$$

In some embodiments, a dysphagia risk index which is higher than a predetermined reference dysphagia index is a predictor for the occurrence of dysphagia in the subject following therapy and/or surgery. In one embodiment, the predetermined reference dysphagia index is 14.

In some embodiments, the surgery is an anti-reflux surgery. In one embodiment, the anti-reflux surgery is Nissan Fundoplication.

In some embodiments of the first aspect of the invention, the pressure measurements are used to guide analysis of the intraluminal impedance measurements. In one embodiment, one of the pressure flow variables is the nadir of the impedance waveform preceding peak pressure (Zn) in the pharynx and/or esophagus of the subject. In one embodiment, a higher Zn in the subject compared to the predetermined pharyngeal and/or esophageal Zn reference value is indicative of ineffective swallowing and/or risk of aspiration in the subject. In one embodiment the predetermined esophageal Zn reference value is about 0.025 msu.

In some embodiments, one of the pressure flow variables is the impedance at the time of peak pressure (ZPp) in the pharynx and/or esophagus of the subject. In one embodiment, a lower ZPp in the subject compared to the predetermined pharyngeal and/or esophageal ZPp reference value is indicative of ineffective swallowing and/or risk of aspiration in the subject. In one embodiment the predetermined esophageal ZPp reference value is about 0.208 msu. In one embodiment, if the ZPp is lower than the Zn in the subject, the ineffective swallowing is due to an obstruction in the pharynx and/or esophagus of the subject.

In some embodiments, the value of the one or more pressure flow variables is combined to generate an obstructive risk index in the subject. In one embodiment, the obstructive risk index has the following formula:

$$Zn/ZPp$$

In some embodiments, an obstructive risk index which is higher than a predetermined reference obstructive index indicates that the ineffective swallowing is due to an obstruction in the pharynx and/or esophagus of the subject. In one embodiment, the predetermined reference obstructive index is 1, and a subject with an obstructive risk index of greater than 1 has an ineffective swallow due to an obstruction in the pharynx and/or esophagus of the subject.

In some embodiments, the ineffective swallowing is due to an obstruction in the pharynx and/or esophagus of the subject, and the method identifies the location of the obstruction. In one embodiment, one of the pressure flow variables is the maximum nadir of the impedance waveform preceding peak pressure (max Zn) in the pharynx and/or esophagus of the subject during clearance of the bolus from the mouth and/or throat of the subject.

In some embodiments, one of the pressure flow variables is the minimum impedance at the time of peak pressure (min ZPp) in the pharynx and/or esophagus of the subject during clearance of the bolus from the mouth and/or throat of the subject. In one embodiment, the position of the min ZPp in the pharynx and/or esophagus of the subject is indicative of the position of the obstruction.

In some embodiments, the one or more pressure flow variables are the nadir of the impedance waveform preceding peak pressure (Zn) in the pharynx and/or esophagus of the subject during clearance of the bolus from the mouth and/or throat of the subject, and the impedance at the time of peak pressure (ZPp) in the pharynx and/or esophagus of the subject during clearance of the bolus from the mouth and/or throat of the subject, and wherein the position of the maximum Zn/ZPp in the pharynx and/or esophagus of the subject is indicative of the position of the obstruction.

In a second aspect, the present invention provides a method for assessing swallowing motor function in a subject, the method including:
  (a) accessing intraluminal impedance measurements and pressure measurements obtained from the pharynx and/or esophagus of the subject during clearance of a bolus from the mouth and/or throat of the subject;
  (b) combining the intraluminal impedance and pressure measurements;
  (c) generating a swallow risk index for the subject based on a combination of a value of more than one pressure-flow variable in the pharynx and/or esophagus of the subject, wherein the value is derived from an analysis of the combined intraluminal impedance and pressure measurements; and
  (d) assessing swallowing motor function in the subject by comparing the swallow risk index for the subject to a predetermined reference swallow index.

In one embodiment, the subject is suspected to have dysphagia. In one embodiment, the method is used to identify ineffective swallowing in the subject.

In some embodiments of the second aspect of the invention, the method is used to determine risk of aspiration in the subject, diagnose an increased likelihood of aspiration in the subject, predict aspiration in the subject, and/or identify a subject susceptible to aspiration.

In some embodiments, a swallow risk index for the subject which is higher than the predetermined reference swallow index indicates an ineffective swallow and/or risk of aspiration in the subject.

In some embodiments of the second aspect of the invention, the intraluminal impedance measurements are used to guide analysis of the pressure measurements.

In some embodiments, the intraluminal impedance measurements are used to generate an impedance waveform of the bolus clearance.

In some embodiments, the pressure measurements are used to generate a pressure waveform of the bolus clearance. In one embodiment, analysis of the combined intraluminal impedance and pressure measurements includes measuring the nadir of the impedance waveform, and wherein the nadir of the impedance waveform is used as a time marker for analysis of the pressure waveform. For example, in one embodiment, one of the pressure-flow variables is the pressure at the nadir of the impedance waveform (PNadImp) in the pharynx and/or esophagus of the subject.

In some embodiments of the second aspect of the invention, one of the pressure-flow variables is the peak pressure of the pressure waveform (PeakP) in the pharynx and/or esophagus of the subject. In one embodiment, one of the pressure-flow variables is the time from the nadir of the impedance waveform to the peak pressure (TNadImp-PeakP) in the pharynx and/or esophagus of the subject.

In some embodiments of the second aspect of the invention, one of the pressure-flow variables is the duration of the drop in intraluminal impedance during bolus clearance (Flow Interval) in the pharynx and/or esophagus of the subject.

In some embodiments of the second aspect of the invention, the swallow risk index of the subject is derived from the following formula:

$$\frac{(\text{Flow Interval} \times P\text{NadImp})}{(\text{PeakP} \times (P\text{NadImp} - \text{PeakP} + 1))} \times 100$$

In one embodiment, the predetermined reference swallow index is 9, and a subject with a swallow risk index of about 10 or higher has an ineffective swallow.

In one embodiment, the predetermined reference swallow index is 15, and a subject with a swallow risk index of about 16 or higher has an ineffective swallow and/or risk of aspiration.

In some embodiments of the second aspect of the invention, the method is used to predict the occurrence of dysphagia in the subject following therapy. In one embodiment, one of the pressure flow variables is intrabolus pressure (IBP) in the pharynx and/or esophagus of the subject. In one embodiment, a higher IBP in the subject compared to the predetermined pharyngeal and/or esophageal IBP reference value is a predictor for the occurrence of dysphagia in the subject following therapy and/or surgery. In one embodiment, the predetermined esophageal IBP reference value is about 12 mmHg.

In some embodiments of the second aspect of the invention, one of the pressure flow variables is intrabolus pressure slope (IBP Slope) in the pharynx and/or esophagus of the subject. In one embodiment, an elevated IBP Slope in the subject compared to the predetermined pharyngeal and/or esophageal IBP Slope reference value is a predictor for the occurrence of dysphagia in the subject following therapy and/or surgery. In one embodiment, the predetermined esophageal IBP Slope reference value is about 5 mmHg/sec.

In some embodiments of the second aspect of the invention, one of the pressure flow variables is time from the nadir of the impedance waveform to the peak pressure (TNadImp-PeakP) in the pharynx and/or esophagus of the subject. In one embodiment, a shorter TNadImp-PeakP in the subject compared to the predetermined pharyngeal and/or esophageal TNadImp-PeakP reference value is a predictor for the occurrence of dysphagia in the subject following therapy and/or surgery. In one embodiment, the predetermined esophageal TNadImp-PeakP reference value is about 3.5 sec.

In some embodiments of the second aspect of the invention, the value of more than one pressure-flow variable is combined to generate a dysphagia risk index in the subject. In one embodiment, the dysphagia risk index has the following formula:

$$\text{IBP} \times \text{IBP Slope} \times \text{TNadImp-PeakP}^{-1}$$

In some embodiments, a dysphagia risk index which is higher than a predetermined reference dysphagia index is a predictor for the occurrence of dysphagia in the subject following therapy and/or surgery. In one embodiment, the predetermined reference dysphagia index is 14.

In some embodiments of the second aspect of the invention, the surgery is an anti-reflux surgery. In one embodiment, the anti-reflux surgery is Nissan Fundoplication.

In a third aspect, the present invention provides a method for assessing swallowing motor function in a subject, the method including:

(a) accessing intraluminal impedance measurements and pressure measurements obtained from the pharynx and/or esophagus of the subject during clearance of a bolus from the mouth and/or throat of the subject;

(b) combining the intraluminal impedance and pressure measurements;

(c) generating an obstructive risk index for the subject based on a combination of a value of more than one pressure-flow variable in the pharynx and/or esophagus of the subject, wherein the value is derived from an analysis of the combined intraluminal impedance and pressure measurements; and (d) assessing swallowing motor function in the subject by comparing the obstructive risk index for the subject to a predetermined reference obstructive index.

In one embodiment, the subject is suspected to have dysphagia.

In some embodiments of the third aspect of the invention, the method is used to identify ineffective swallowing in the subject, wherein said ineffective swallowing is due to an obstruction in the pharynx and/or esophagus of the subject.

In some embodiments of the third aspect of the invention, an obstructive risk index for the subject which is higher than the predetermined reference obstructive index indicates ineffective swallowing in the subject, wherein said ineffective swallowing is due to an obstruction in the pharynx and/or esophagus of the subject.

In some embodiments of the third aspect of the invention, the intraluminal pressure measurements are used to guide analysis of the intraluminal impedance measurements.

In some embodiments of the third aspect of the invention, the pressure measurements are used to generate a pressure waveform of the bolus clearance.

In some embodiments of the third aspect of the invention, the intraluminal impedance measurements are used to generate an impedance waveform of the bolus clearance.

In one embodiment, one of the pressure flow variables is the nadir of the impedance waveform preceding peak pressure (Zn) in the pharynx and/or esophagus of the subject.

In some embodiments of the third aspect of the invention, one of the pressure flow variables is the impedance at the time of peak pressure (ZPp) in the pharynx and/or esophagus of the subject. In one embodiment, the obstructive risk index of the subject is derived from the following formula:

$$Zn/ZPp$$

In one embodiment, the predetermined reference obstructive index is 1, and a subject with an obstructive risk index of greater than 1 has an ineffective swallow due to an obstruction in the pharynx and/or esophagus of the subject.

In a fourth aspect, the present invention provides software for use with a computer, the computer including a processor and associated memory for storing the software, wherein the software includes a series of instructions executable by the processor to carry out a method according to any one or more of the first, second and third aspects of the invention.

In a fifth aspect, the present invention provides a computer readable media containing software according to a fourth aspect of the invention.

In a sixth aspect, the present invention provides an apparatus for enabling an assessment of swallowing motor function in a subject, the apparatus including:
   (a) a processor;
   (b) a memory; and
   (c) software resident in memory accessible to the processor, the software executable by the processor to carry out a method according to any one or more of the first, second and third aspects of the invention.

In a seventh aspect, the present invention provides a computer readable media including a set of instructions in the form of a computer software program, the instructions being executable by a processing device on-board a programmed computer, wherein execution of the instructions causes the programmed computer to:
   (a) accept, as an input, intraluminal impedance and pressure measurements obtained from the pharynx and/or esophagus of a subject during clearance of a bolus from the mouth and/or throat of the subject;
   (b) combine and analyse the intraluminal impedance and pressure measurements to derive a value for one or more pressure-flow variables in the pharynx and/or esophagus of the subject;
   (c) assess swallowing motor function in the subject by performing a comparison between the value of the one or more pressure-flow variables with a predetermined pharyngeal and/or esophageal reference value for the one or more pressure-flow variables; and
   (d) provide, as an output, an assessment of swallowing motor function in the subject on the basis of the comparison.

In one embodiment, the computer readable media further includes executable instructions which identify ineffective swallowing in the subject on the basis of the comparison.

In some embodiments, the computer readable media further includes executable instructions which determine risk of aspiration in the subject, diagnose an increased likelihood of aspiration in the subject, predict aspiration in the subject, and/or identify a subject susceptible to aspiration.

In some embodiments, the computer readable media further includes executable instructions which predict the occurrence of dysphagia in the subject following therapy and/or surgery.

In an eighth aspect, the present invention provides a combination product, the combination product including:
   (a) a device for obtaining intraluminal impedance and pressure measurements from the pharynx and/or esophagus of a subject during clearance of a bolus from the mouth and/or throat of the subject; and
   (b) software according to a fourth aspect of the invention, an apparatus according to a sixth aspect of the invention, or a computer readable media according to the fifth or seventh aspects of the invention.

BRIEF DESCRIPTION OF THE FIGURES

The patent or application file contains at least one drawing executed in color. Copies of this patent or patent application publication with color drawings) will be provided by the Office upon request and payment of the necessary fee.

FIG. 2 provides a series of graphs which show impedance (A) and pressure (B) measurements (represented as respective waveforms) derived from the passage of a bolus from the mouth to the esophagus of a subject. FIG. 2C shows how a combination of the impedance and pressure waveforms delineates four pharyngeal pressure-flow variables, namely PNadImp, Peak Pressure (PeakP), TNadImp-PeakP and Flow Interval.

FIG. 11 provides graphs showing agreement between paediatric patient average SRI cut-off criteria and the detection of aspiration-penetration during fluoroscopy. (A) Kappa agreement. (B) ROC curve.

FIG. 19A shows an example of a normal swallow, FIG. 19B is representative of ineffective bolus transport, and FIG. 19C shows an example of the change in pressure and impedance waveforms at the position of an obstruction. Changes in the values of Zn and ZPp are shown by arrows.

FIG. 20A shows an example of a normal swallow, FIG. 20B is representative of ineffective bolus transport, and FIG. 20C shows an example of the change in impedance values and Zn/ZPp ratio at the position of an obstruction.

FIG. 27 is a table providing the summary data of 115 swallows in controls and patients representing the relationships among important objective pharyngeal variables and the presence of post-swallow residue.

FIG. 28 is a table providing the summary data of 115 swallows in controls and patients representing the relationships among important objective UES variables and the presence of post-swallow residue.

FIG. 29 is a table providing pressure flow variables for viscous swallows pre and post surgery and in relation to the presence of dysphagia pre and/or post surgery.

FIG. 30 is a table providing pressure flow variables and the dyphagia risk index for viscous swallows before and after surgery grouped by patients with no dysphagia, dysphagia pre and post surgery and dysphagia post-surgery only.

DESCRIPTION OF THE INVENTION

Figure 1:
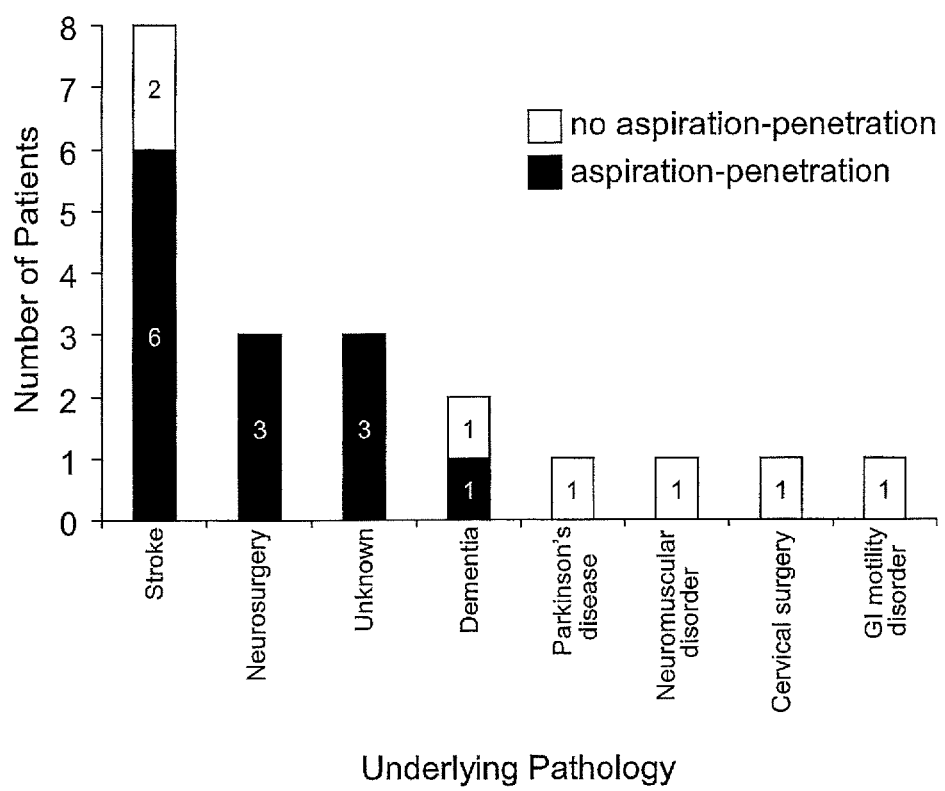
FIG. 1 is a graph summarising the subject cohort used for the studies described in Example 1. The graph shows the underlying medical pathology of each subject and the presence of aspiration-penetration as detected by video fluoroscopy.

The present invention arises from studies involving the analysis of manometry and impedance measurements during swallowing. In accordance with the present invention it has been found that combining data obtained from manometry and impedance measurements provides valuable markers for the assessment of swallowing motor function in a subject.

Accordingly, in a first aspect, the present invention provides a method for assessing swallowing motor function in a subject, the method including:

(a) accessing intraluminal impedance measurements and pressure measurements obtained from the pharynx and/or esophagus of the subject during clearance of a bolus from the mouth and/or throat of the subject;

(b) combining and analysing the intraluminal impedance and pressure measurements to derive a value for one or more pressure-flow variables in the pharynx and/or esophagus of the subject; and (c) assessing swallowing motor function in the subject by comparing the value of the one or more pressure-flow variables with a predetermined pharyngeal and/or esophageal reference value for the one or more pressure-flow variables.

In a second aspect, the present invention provides a method for assessing swallowing motor function in a subject, the method including:

(a) accessing intraluminal impedance measurements and pressure measurements obtained from the pharynx and/or esophagus of the subject during clearance of a bolus from the mouth and/or throat of the subject;

(b) combining the intraluminal impedance and pressure measurements;

(c) generating a swallow risk index for the subject based on a combination of a value of more than one pressure-flow variable in the pharynx and/or esophagus of the subject, wherein the value is derived from an analysis of the combined intraluminal impedance and pressure measurements; and (d) assessing swallowing motor function in the subject by comparing the swallow risk index for the subject to a predetermined reference swallow index.

In a third aspect, the present invention provides a method for assessing swallowing motor function in a subject, the method including:
(a) accessing intraluminal impedance measurements and pressure measurements obtained from the pharynx and/or esophagus of the subject during clearance of a bolus from the mouth and/or throat of the subject;
(b) combining the intraluminal impedance and pressure measurements;
(c) generating an obstructive risk index for the subject based on a combination of a value of more than one pressure-flow variable in the pharynx and/or esophagus of the subject, wherein the value is derived from an analysis of the combined intraluminal impedance and pressure measurements; and
(d) assessing swallowing motor function in the subject by comparing the obstructive risk index for the subject to a predetermined reference obstructive index.

In some embodiments of the aforementioned aspects of the invention, the subject is suspected to have dysphagia.

By allowing an assessment of swallowing motor function in a subject, these methods may be used to identify a subject who has an ineffective swallow and is therefore at risk of aspiration. Therefore, in some embodiments these methods can be used to determine risk of aspiration in a subject, diagnose an increased likelihood of aspiration in a subject, predict aspiration in a subject, and/or identify a subject susceptible to aspiration.

As used herein, the term "ineffective swallowing" or "abnormal swallow" or similar terms is taken to mean a swallow which is associated with aberrant bolus flow, indicated by bolus material entering the airways, and/or is a swallow that results in the presence of post-swallow residue in the pharynx or esophagus. Accordingly, a "normal" swallow is a swallow which allows bolus to be transported from the pharynx to the stomach with insignificant or no bolus material entering the airways and little or no post-swallow residue.

As used herein, the term "swallowing motor function" should be understood to mean the coordinated physiological events that enable the passage of a food and/or liquid bolus from the mouth to the stomach. An assessment of swallowing motor function will typically involve an analysis of pharyngeal and esophageal motor function associated with the pharyngeal and esophageal phases, respectively, of the swallow. The pharyngeal phase is initiated as the tongue propels the bolus posteriorly and the base of the tongue contacts the posterior pharyngeal wall, eliciting a reflexive action that begins a complex series of events—the soft palate elevates to prevent nasal reflux the pharyngeal constrictor musculature contracts to push the bolus through the pharynx; the epiglottis inverts to cover the larynx and prevent aspiration of contents into the airway; the vocal folds adduct to further prevent aspiration; the hyolaryngeal complex moves anteriorly and superiorly, which, in combination with the pressure generated by a bolus, provides anterior traction and intrabolus pressure to open the cricopharyngeus. In contrast, the esophageal phase is completely involuntary and consists of peristaltic waves that propel the food and/or liquid to the stomach.

As set out above, the methods of the present invention include accessing intraluminal impedance measurements and pressure measurements obtained from the pharynx and/or esophagus of a subject during clearance of a bolus from the mouth and/or throat of the subject. As would be understood by a person skilled in the art, "clearance of a bolus" refers to the movement of a solid and/or liquid from the mouth and/or throat of a subject to the stomach.

It is to be made clear that the intraluminal impedance measurements and pressure measurements which are accessed for the methods of the present invention may be accessed from impedance and pressure measurements that have previously been obtained from the subject, and for example have been stored on a data/memory system, or the measurements may be obtained directly from the subject as a bolus clears from the mouth and/or throat of the subject (i.e. in real-time). In the former case, the intraluminal impedance and pressure measurements are therefore obtained in isolation of, and therefore separate to, the methods of the present invention.

Obtaining an "intraluminal impedance" measurement refers to detecting the occurrence of changes (during bolus passage through the pharynx and/or esophagus) in a resistance to electrical current across adjacent electrodes positioned in a serial manner along an axial length of the pharynx and/or esophagus in the gastrointestinal tract.

Intraluminal impedance may be measured in any suitable way, as would be understood by a person skilled in the art. For example, impedance may be measured by way of a narrow indwelling catheter upon which electrodes are longitudinally spaced. When placed in the pharynx and/or esophagus the electrodes are in electrical contact with the luminal mucosa. Such catheters are routinely used for gastrointestinal investigations, most notably the measurement of the frequency and extent of gastro-esophageal reflux in patients with gastro-esophageal reflux disease. A high frequency electrical current is applied through consecutively connected impedance electrode pairs. The spaces between electrodes form linear segments along the catheter. The impedance to current flow for each segment is measured and stored in a sequential scan cycle fast enough to capture the impedance change along the catheter during a swallow accurately. The current is generated and switched by external signal processing hardware and is applied across catheter electrodes via an electrical connector and wires to the electrodes on the catheter. In between swallows, the level of impedance recorded is proportional to the conductance of the luminal mucosa. However, when a conductive bolus material (e.g. a swallowed bolus) passes along the catheter, this causes the measured level of impedance to drop across consecutive electrode pairs (due to the conductance of the bolus material). When the bolus material is cleared from the lumen then the measured level of impedance returns to the baseline value for each impedance segment.

Impedance measurements may be captured electronically and recorded by a data acquisition system (of which there are many commercially available). Impedance patterns may be analysed through the visual detection of the occurrence of impedance drops, with bolus presence defined by a drop of impedance to <50% of baseline levels. There are several semi-automated analysis software platforms that allow this analysis to be performed.

Obtaining a "pressure measurement" (also referred to as manometry) in the pharynx and/or esophagus refers to detecting the occurrence of changes (during bolus passage through the pharynx and/or esophagus) in pressure at these sites as a result of the contraction and relaxation of the pharyngeal and esophageal muscles during peristaltic movement of a bolus from the mouth to the stomach. Static pressures due to bolus passage (intrabolus pressure) can also be measured.

In some embodiments, pressure may be measured in the pharynx and/or esophagus via an indwelling catheter. As would be understood by a person skilled in the art, there are several methods for achieving this, including: (1) perfusion manometry—whereby a multi-lumen water-perfused catheter is introduced, with lumen vented in a longitudinal sequence along the catheter. The catheter lumen are perfused and intraluminal pressures are transferred to pressure transducers external to the catheter via the water in the catheter lumen; (2) use of solid state electronic (usually piezo-resistive) transducers which are mounted along the catheter, electrically isolated from the patient and connected to an external signal processing unit by wires within the catheter; (3) using optic fibre technology whereby deformation by pressure of a Bragg grating (etched onto an optic fibre) causes a change in the wavelength of light proportionate to pressure on the catheter, and (4) other methods utilised in commercial products including sensors measuring a change in capacitance as an analog of pressure and sensors using the deflection of an optic fibre due to applied pressure.

In some embodiments, both pressure and impedance can be recorded simultaneously by a catheter incorporating both pressure sensors and impedance electrodes. Examples of such catheters include those sold by Unisensor USA Inc, Portsmouth, N.H. In one embodiment, a 3.2 mm diameter solid state manometric and impedance catheter incorporating twenty five 1 cm-spaced pressure sensors and twelve 2 cm long impedance segments may be used. However, it would be understood by a skilled person that any method for recording pressure and impedance knows in the art, whether conducted simultaneously or not, may be used.

It has been found that the combination of manometry data and impedance measurements indicating bolus position provide adjunctive information. When the two measurements are combined and properly analysed together, they provide a more complete picture of swallowing motor function. Accordingly, use of the term "combining" in the context of the present invention is taken to mean that the impedance and pressure measurement data are analysed together so that one set of data is used to guide analysis of the other.

This approach contrasts with the standard approach of evaluating impedance and pressure findings separately. For example, if impedance measurement detects failure of bolus clearance, the pressure measurement is then separately analysed to determine a possible cause. Therefore, the term "combining" is not taken to mean that the data obtained from the impedance measurements is analysed in isolation to the pressure measurement data and then both sets of data are combined to provide an assessment of swallow mechanics.

While manometry provides information about the contractile pressures that normally drive a bolus to the stomach, in certain situations, manometry alone may not provide sufficient information to fully assess bolus movement, particularly with respect to making a definitive diagnosis of certain disorders. By co-registering manometry and impedance data sets in both time and position according to the present invention, the interaction between contractile pressure and bolus movement during swallowing can be analysed in a precise and informative manner, and in a way that is not possible by analysing these two data sets independently. This enables a more reliable assessment of swallowing motor function.

According to the aforementioned aspects of the present invention, the intraluminal impedance and pressure measurements are combined, and analysis of the combined measurements derives a value for one or more pressure-flow variables in the pharynx and/or esophagus of the subject.

The intraluminal impedance and pressure measurements may be combined such that in one embodiment, the impedance measurements are used to guide analysis of the pressure measurements. Alternatively, in another embodiment the pressure measurements are used to guide analysis of the impedance measurements.

In some embodiments, analysis of the intraluminal impedance measurements includes the generation of an impedance waveform of the bolus clearance. Similarly, in some embodiments, analysis of the pressure measurements includes generation of a pressure waveform of the bolus clearance. As used herein, an "impedance waveform" or a "pressure waveform" are taken to mean the typical shape of a plot of impedance or pressure change over time. Impedance levels typically drop in relation to bolus presence and rise again with clearance of the bolus, hence the typical waveform drops below baseline then rises back to baseline. Pressure levels usually rise with luminal contraction onto the catheter and drop when the contraction subsides, hence the typical waveform rises from baseline then drops back to baseline.

According to the aforementioned aspects of the present invention, and as described above, analysing the combined intraluminal impedance and pressure measurements derives a value for one or more pressure-flow variables in the pharynx and/or esophagus of the subject. As used herein, a "pressure-flow variable" is taken to mean a characteristic of the pressure waveform or impedance waveform or both wave forms (as is the case with timing variables) that are associated with swallowing motor function and are altered with pathology. A pressure-flow variable may be a characteristic of motor function of the pharynx and/or the esophagus during swallowing.

To derive a value for a pressure-flow variable, pressure and impedance measurements may be combined and analysed by using characteristics of the impedance waveform, such as the time of its nadir (lowest point), as a time reference for direct measurement of pressure, or to measure the interval of time to a pressure event, such as the peak of a pharyngeal/oesophageal contraction. The absolute value of nadir impedance recorded in any location is related to the presence of bolus and the diameter of the lumen, hence anatomical regions of abnormal narrowing (such as strictures, webs, bars) may be identified by an increase in absolute impedance recorded. For example, the nadir of the impedance waveform corresponds with when the lumen (pharynx or esophagus) is maximally distended/filled by a conductive bolus. The nadir impedance of different channels can be easily identified and thus gives a point in time and space at which pressure can be measured. Accordingly, in one embodiment of the aforementioned aspects of the invention, combining and analysing the intraluminal impedance and pressure measurements includes measuring the nadir of the impedance waveform, and wherein the nadir of the impedance waveform is used as a time marker for analysis of the pressure waveform. In effect, the pressure at the nadir of the impedance waveform (PNadImp) represents one pressure-flow variable of swallow function. The pressure at nadir impedance is indicative of resistance within the pharyngo-esophageal segment with a higher pressure indicating more resistance.

From this impedance detected time point, the time interval to attainment of peak contractile pressure (Peak Pressure, PeakP, or Pp) of the pharynx or esophagus can then be measured. The time interval from nadir impedance to peak pressure (TNadImp-PeakP) is a marker of swallowing efficiency with a shorter time indicating less efficiency. While manometry alone can reliably detect peak pressure, it does not reliably detect the time when the lumen (pharynx or esophagus) is maximally distended/filled. This time represents a reference time point that provides sensitivity to determining swallowing abnormalities. Therefore, without the use of impedance to guide the determination of the initial time point for pressure measurement, the analysis would not be possible.

By combining and analysing impedance and pressure measurements, the pressure at nadir impedance and time from nadir impedance to peak pressure are pressure-flow variables that may be used for assessing swallowing motor function. The critical identification of nadir impedance to define a point in space and time to commence analysis allows for automation of analysis, thus simplifying the calculation method for the user. Computer-based algorithms can derive a wide variety of variables referenced to this time, for example the pressure at the mid-point of nadir impedance to peak pressure, can be used to approximate intrabolus pressure and the deferential of this pressure and the pressure at nadir impedance can also indicate the slope (or "ramp") of pressure increase which is increased in the setting of obstruction. As measurement is made along the entire pressure impedance array, variables can be determined by averaging along the array or for regions corresponding to particular areas of interest, such as sphincteric regions (UES, LES) and the distal vs proximal parts of the pharynx and esophagus.

Examples of pressure-flow variables which can be identified by the methods of the present invention include, but are not limited to, time of nadir impedance, value of nadir impedance, pressure at nadir impedance, time of peak pressure, value of nadir impedance preceding peak pressure, time from nadir impedance to peak pressure, peak pressure, value of impedance at the time of peak pressure, intrabolus pressure, intrabolus pressure slope, pressure at defined time points along the interval from nadir impedance to peak pressure (e.g. half time between), rate of pressure increase from nadir impedance to peak pressure (and time point between), and ratio of pressure at nadir impedance to peak pressure.

The "value" attributed to each pressure-flow variable will be dictated by the nature of the variable. For example, a variable associated with changes in pressure due to the passage of the bolus to the stomach will generally carry a value measured as a pressure unit, for example mmHg. A variable associated with a particular time point or time period of the swallow will typically carry a time value. Finally, a variable associated with impedance at particular points in bolus passage will generally carry an Ohms value. The maximum, minimum, median, mode, and/or average of any one of these variables for the entire array, or array corresponding to specific regions (UES, LES, proximal/mid/distal pharynx or esophagus) may represent a value for that pressure-flow variable.

According to the first aspect of the invention, once the value of one or more pressure-flow variables has been derived from the combined intraluminal and impedance measurements taken from a subject, the value is compared to a predetermined reference value for that pressure-flow variable to allow an assessment of the swallowing motor function in the subject. For example, the value of a pressure-flow variable derived from the combined analysis of measurements taken from the pharynx (or esophagus) of the subject are compared to a predetermined pharyngeal (or esophageal) reference value for that variable.

The value for each pressure-flow variable in a subject with a normal swallow will typically fall within a uniform range, which in the context of the present invention defines the "predetermined reference value" for that variable. Accordingly, a value obtained from the swallow of a subject for that pressure-flow variable which falls above or below the predetermined reference value, will be indicative of an abnormal or ineffective swallow in the subject, and/or will be indicative of a risk of aspiration in the subject.

In some embodiments of the present invention, one of the pressure-flow variables is the pressure at the nadir of the impedance waveform (PNadImp) in the pharynx and/or esophagus of the subject. This variable measures the pressure in the pharyngeal and/or esophageal lumen when the bolus is being maximally propelled. Higher value s of PNadImp correspond to resistance to bolus flow and/or ineffective bolus propulsion. Accordingly in one embodiment, a higher PNadImp in a subject compared to a predetermined pharyngeal and/or esophageal PNadImp reference value is indicative of ineffective swallowing in the subject, and/or will be indicative of a risk of aspiration in the subject. With respect to the pharynx, the predetermined pharyngeal PNadImp (pPNadImp) reference value for a normal swallow in an adult is typically within the range of from 0 to about 26 mmHg such that a subject with a pPNadImp of about 27 mmHg or higher has a swallow with higher resistance to bolus flow and/or less effective bolus propulsion than a normal swallow which in turn may predispose to aspiration risk.

In some embodiments of the present invention, one of the pressure-flow variables is the peak pressure of the pressure waveform (PeakP) in the pharynx and/or esophagus of the subject. For example, with respect to the pharynx, PeakP indicates contractile vigour of the pharyngeal stripping wave which clears bolus from the pharynx A low PeakP is indicative of weak pressures. Accordingly, in one embodiment, a lower PeakP in the subject compared to a predetermined pharyngeal and/or esophageal PeakP reference value is indicative of ineffective swallowing in the subject, and/or will be indicative of a risk of aspiration in the subject. With respect to the pharynx, the predetermined pharyngeal PeakP (pPeakP) reference value for a normal swallow in an adult is typically within the range of from about 93 to about 255 mmHg such that a subject with a pPeakP of about 92 mm Hg or lower has an ineffective swallow and/or risk of aspiration.

In some embodiments of the present invention, one of the pressure-flow variables is the time from the nadir of the impedance waveform to the PeakP (TNadImp-PeakP) in the pharynx and/or esophagus of the subject. For example, with respect to the pharynx TNadImp-PeakP indicates the effectiveness of propulsion of the bolus (by the tongue) in advance of the pharyngeal contraction. A shorter TNadImp-PeakP is suggestive of weak propulsion. Accordingly, a shorter TNadImp-PeakP in a subject compared to a predetermined pharyngeal and/or esophageal TNadImp-PeakP reference value is indicative of ineffective swallowing in the subject, and/or will be indicative of a risk of aspiration in the subject. With respect to the pharynx, the predetermined pharyngeal TNadImp-PeakP (pTNadImp-PeakP) reference value for a normal swallow in an adult is typically within the range of from about 371 to about 640 msec such that a subject with a pTNadImp-PeakP of about 370 msec or shorter has an ineffective swallow and/or risk of aspiration.

In some embodiments of the present invention, one of the pressure-flow variables is the duration of the drop in intraluminal impedance during bolus clearance (Flow Interval) in the pharynx and/or esophagus of the subject. Flow Interval is an estimate of the bolus presence before, during, and after the swallow. A longer Flow Interval in a subject compared to a predetermined pharyngeal and/or esophageal Flow Interval reference value is indicative of ineffective swallowing in the subject, and/or will be indicative of a risk of aspiration in the subject. With respect to the pharynx, the predetermined Flow Interval (pFlow Interval) reference value for a normal swallow in an adult is typically within the range of from about 100 to about 1250 msec such that a subject with a pFlow Interval of 1251 msec or longer has an ineffective swallow and/or risk of aspiration.

As would be understood by a person skilled in the art, a pressure-flow variable according to the present invention need not be limited to one or more of PNadImp, PeakP, TNadImp-PeakP and Flow Interval. Any pressure-flow variable which provides an informative characteristic of the pressure waveform or impedance waveform associated with swallow motor function may be used either in isolation, or in combination, with any one or more of the aforementioned variables.

According to the second aspect of the present invention, and in some embodiments of the first aspect of the present invention, a value of more than one pressure-flow variable is combined to generate a swallow risk index in the subject. The value of the swallow risk index in the subject is essentially an indicator of the effectiveness of swallowing motor function in the subject, which in turn enables the identification of an ineffective swallow and risk of aspiration in the subject.

In some embodiments of the present invention, the swallow risk index has the following formula:

$$\frac{(\text{Flow Interval} \times PNadImp)}{(PeakP \times (PNadImp - PeakP + 1))} \times 100$$

In some embodiments of the present invention, a swallow risk index which is higher than a predetermined reference swallow index is indicative of an ineffective swallow and/or risk of aspiration in the subject. The "predetermined reference swallow index" essentially represents a swallow risk index value or range of swallow risk index values which are derived from a subject or subjects with a normal swallow. Accordingly, a swallow risk index which is higher than the predetermined reference swallow index value, or outside the predetermined reference swallow index value range, is indicative of an ineffective swallow and/or is indicative of a risk of aspiration in the subject.

With reference to the above formula, when the value of each of the pressure-flow variables derived from the pharynx of an individual with a normal swallow is incorporated into the formula, a predetermined reference swallow index of between 0 to about 9 is obtained, and is therefore indicative of a normal swallow. In some embodiments, a subject who has a swallow risk index of between about 10 to about 15 will have post-swallow bolus residue indicative of an ineffective swallow. Furthermore, a subject who has a swallow risk index of about 16 or higher is also at risk of aspiration.

It will be appreciated that a swallow risk index may be obtained from any combination of pressure-flow variables identified by the methods of the present invention and which are informative with respect to swallowing motor function. The swallow risk index need not be restricted to those variables identified in the formula above.

In some embodiments, the method according to the aforementioned aspects of the invention may be used to predict the occurrence of dysphagia in the subject following therapy and/or surgery. For example, a subject who has undergone surgery for the treatment of a gastrointestinal disorder (such as gastroesophageal reflux disease) will often develop post-operative complications due to restriction of the esophago-gastric junction. Furthermore, upper esophageal sphincter (UES) obstruction can occur following radio-therapy for head and neck cancer, following cervical surgery, in relation to neurological diseases such a cerebral palsy and in relation to anatomical abnormalities (bars/strictures). In addition, esophageal body obstruction can occur in relation to the formation of strictures/webs which occlude the lumen. Obstruction of the UES or esophageal body, and restriction of the esophago-gastric junction are common causes of dysphagia.

The inventor has found that one or more pressure-flow variables derived from the methods of the present invention are able to predict the occurrence of dysphagia in subjects which have undergone therapy and/or surgery for various diseases and conditions, including those described above. In one embodiment, one of the pressure-flow variables is intrabolus pressure (IBP) in the pharynx and/or esophagus of the subject. This variable measures the pressure required to move a bolus through the pharynx or esophagus, wherein IBP increases in circumstances of resistance to bolus movement (for example following EGJ restriction produced by fundoplication). Accordingly, in one embodiment, a higher IBP in a subject compared to a predetermined pharyngeal and/or esophageal IBP reference value is a predictor for the occurrence of dysphagia in the subject following therapy and/or surgery. With respect to the esophagus, the predetermined esophageal IBP (eIBP) reference value is typically within the range of from 0 to about 12 mmHg such that a subject with an eIBP of about 13 mmHg or higher is predicted to be at risk of dysphagia, post-surgery.

In some embodiments, one of the pressure-flow variables is intrabolus pressure slope (IBP Slope) in the pharynx and/or esophagus of the subject. This variable measures the rate of intrabolus pressure change over time, wherein the rate of change is elevated closer to an obstruction. Accordingly, in one embodiment, an elevated IBP Slope in the subject compared to a predetermined pharyngeal and/or esophageal IBP Slope reference value is a predictor for the occurrence of dysphagia in the subject following therapy and/or surgery. With respect to the esophagus, the predetermined esophageal IBP Slope (eIBP Slope) reference value is typically within the range of from 0 to about 5 mmHg/sec such that a subject with an eIBP Slope of about 6 mmHg or higher is predicted to be at risk of dysphagia, post-surgery.

In some embodiments, one of the pressure-flow variables is time from the nadir of the impedance waveform to the peak pressure (TNadImp-PeakP) in the pharynx and/or esophagus of the subject. As discussed above, and with reference to the esophagus, this variable measures the time interval from maximum bolus flow to oesophageal contraction and is related to the speed and extent of bolus propulsion into the oesophageal lumen balanced by resistive elements in the lumen that slow movement of the bolus. Accordingly, in one embodiment, a shorter TNadImp-PeakP in the subject compared to a predetermined pharyngeal and/or esophageal TNadImp-PeakP reference value is a predictor for the occurrence of dysphagia in the subject following therapy and/or surgery. With respect to the esophagus, the predetermined esophageal TNadImp-PeakP (eTNadImp-PeakP) reference value is in the range of from about 3.5 sec to about 8 sec such that a subject with an eTNadImp-PeakP of about 3.4 sec or less is predicted to be at risk of dysphagia, post-surgery.

Although the inventor has found that IBP, IBP Slope and TNadImp-PeakP are pressure-flow variables which can predict the occurrence of dysphagia in the subject following therapy and/or surgery, it is to be understood that the invention includes any other pressure-flow which also acts as predictor of dysphagia post-therapy and/or post-surgery, and which has been identified by the methods of the present invention.

In some embodiments, the value of more than one of the pressure-flow variables that can predict the occurrence of dysphagia in the subject following therapy and/or surgery may be combined to generate a dysphagia risk index in the subject. The value of the dysphagia risk index is essentially a predictor of dysphagia in the subject post-therapy and/or post-surgery. In some embodiments of the present invention, the dysphagia risk index has the following formula:

$$IBP \times IBP\ Slope \times TNadImp\text{-}PeakP^{-1}$$

In some embodiments of the present invention, a dysphagia risk index which is higher than a predetermined reference dysphagia index is a predictor for the occurrence of dysphagia in the subject following therapy and/or surgery. The "predetermined reference dysphagia index" essentially represents a dysphagia risk index value or range of dysphagia risk index values which are derived from a subject or subjects who develop dysphagia symptoms post-surgery and/or post-therapy. Accordingly, a dysphagia risk index which is higher than the predetermined reference dysphagia index value, or outside the predetermined reference dysphagia index value range, is a predictor for the occurrence of dysphagia in the subject following therapy and/or surgery.

With reference to the above formula, the inventor has found that when the value of each of the pressure-flow variables derived from the esophagus of an individual with a normal swallow is incorporated into the formula, a predetermined reference dysphagia index of between 0 to about 14 is obtained, and is therefore indicative of an absence of dysphagia symptoms post-surgery and/or post-therapy. Accordingly, a subject who has a dysphagia risk index of about 15 or higher post-surgery and/or post-therapy is predicted to be at risk of developing dysphagia.

In one embodiment, the surgery is an anti-reflux surgery, for example Nissan Fundoplication.

It will be appreciated that a dysphagia risk index may be obtained from any combination of pressure-flow variables identified by the methods of the present invention and which are informative with respect to swallowing motor function. The dysphagia risk index need not be restricted to those variables identified in the formula above.

As referred to above, in some embodiments of the first aspect of the invention, and in some embodiments of the third aspect of the invention, the pressure measurements which are obtained from the pharynx and/or esophagus of the subject during clearance of the bolus from the mouth and/or throat of the subject can be used to guide analysis of the intraluminal impedance measurements. For example, pressure measurements obtained during the contractile wave can be used as a reference point to obtain an impedance value at any time in the contractile wave.

Accordingly, in some embodiments one of the pressure-flow variables is the nadir of the impedance waveform preceding peak pressure (Zn) in the pharynx and/or esophagus of the subject. This variable measures the impedance in the pharyngeal and/or esophageal lumen when the bolus is being maximally propelled and with the lumen maximally distended by the bolus, i.e. prior to the pharyngeal and/or esophageal contractile wave. Higher values of Zn correspond to resistance to bolus flow, possibly due to luminal narrowing, and/or ineffective bolus propulsion. Accordingly, in one embodiment, a higher Zn in the subject compared to a predetermined pharyngeal and/or esophageal Zn reference value is indicative of ineffective swallowing in the subject and risk of dysphagia due to bolus hold up. With respect to the esophagus, the predetermined esophageal Zn reference value for a normal swallow in an adult is typically within the range of 0.001-0.027 median standardised units (msu) as derived from measurements taken along the length of the esophagus during bolus transit. Still further, when the maximum value of Zn (max Zn) along the esophagus in normal subjects is considered, the predetermined esophageal Zn reference value for max Zn in an adult with a normal swallow is typically within the range of 0.002-0.031 median standardised units (msu). Therefore, a subject with a Zn of about 0.025 or higher, or a max Zn of about 0.03 or higher, has a swallow with abnormal resistance to bolus flow and/or less effective bolus propulsion than a normal swallow which in turn may predispose to bolus hold up.

In some embodiments of the present invention, one of the pressure-flow variables is the impedance at the time of peak pressure (ZPp) in the pharynx and/or esophagus of the subject. This variable measures the impedance in the pharyngeal and/or esophageal lumen during the pharyngeal and/or esophageal contractile wave. Failure of a bolus to efficiently clear the pharyngeal and/or esophageal lumen will result in a low ZPp value. This is because bolus residue acts a conductor for current flow between luminal electrodes measuring impedance levels during swallowing.

During an ineffective swallow, ZPp will actually approach Zn. Accordingly, in one embodiment, a lower ZPp in the subject compared to a predetermined pharyngeal and/or esophageal ZPp reference value is indicative of ineffective swallowing in the subject, and/or will be indicative of a risk of bolus hold up in the subject. With respect to the esophagus, when the minimum value of ZPp (min ZPp) along the esophagus during bolus transport in normal subjects is considered, the predetermined esophageal ZPp reference value for min ZPp in an adult with a normal swallow is typically within the range of 0.188-0.779 median standardised units (msu). Therefore, a subject with a min ZpP of about 0.208 msu or lower has an ineffective swallow and/or risk of bolus hold up.

As indicated above, during an ineffective swallow ZPp will actually approach Zn. As an extension of this, when the pharyngeal and/or esophageal lumen is physically obstructed (either due to a zone of narrowing, or due to reduced luminal compliance which reduces the degree to which the lumen can distend/stretch to accommodate passage of a bolus) the reduced cross-sectional area increases the value of Zn such that ZPp drops to below Zn. This is due to the presence of residue and the fact that the pharyngeal and/or esophageal contractile wave "bares down" upon the impedance segment with much greater force than normal. Accordingly, in some embodiments if the ZPp is lower than the Zn in the subject, the ineffective swallowing is due to an obstruction in the pharynx and/or esophagus of the subject.

According to the third aspect of the present invention, and in some embodiments of the first aspect of the present invention, a value of more than one pressure-flow variable is combined to generate an obstructive risk index in the subject. The value of the obstructive risk index in the subject is essentially an indicator as to whether the ineffective swallowing in the subject is due to an obstruction in the pharynx and/or esophagus of the subject.

In some embodiments, the obstructive risk index has the following formula:

$$Zn/ZPp$$

In some embodiments of the present invention, an obstructive risk index which is higher than a predetermined reference obstructive index indicates that the ineffective swallowing is due to an obstruction in the pharynx and/or esophagus of the subject. The "predetermined reference obstructive index" essentially represents an obstructive risk index value or range of obstructive risk index values which are derived from a subject or subjects with a normal and/or unobstructed swallow. Accordingly, an obstructive risk index which is higher than a predetermined reference obstructive index value, or which is outside the predetermined reference obstructive index range, is indicative of an ineffective swallow due to an obstruction in the pharynx and/or esophagus.

With reference to the above formula, when the value of each of the pressure-flow variables derived from the esophagus of an individual with an unobstructed swallow is incorporated into the formula, a predetermined reference obstructive index range of less than 1 is obtained, and is therefore indicative of an unobstructed swallow. In some embodiments, a subject who has an obstructive risk index of greater than 1 indicates that the ineffective swallow is due to an obstruction in the pharynx and/or esophagus of the subject.

In some embodiments, the obstructive risk index has the following formula:

$$NadImp \times TNadImp\text{-}PeakP^{-1}$$

With reference to this formula, if the lumen being distended is focally narrowed/obstructed then the rate of bolus flow through the narrowing and the bolus volume within the narrowing is reduced which leads to the value of NadImp rising and TNadImp-PeakP becoming shorter within the narrowing. Accordingly, a subject with an obstructive risk index derived from the above formula which is higher than a predetermined reference obstructive index derived from this formula indicates that the ineffective swallow is due to an obstruction in the pharynx and/or esophagus of the subject.

It will be appreciated that an obstructive risk index may be obtained from any combination of pressure-flow variables identified by the methods of the present invention and which are informative with respect to the presence of an obstruction. The obstructive risk index need not be restricted to those variables identified in the formulae above.

In some embodiments, the methods of the present invention may be used to identify the location of an obstruction along the pharynx and/or esophagus of a subject. For example, obstruction of the upperesophageal sphincter (UES) or esophageal body is common cause of dysphagia. As indicated above, such obstructions often occur following treatment for head and neck cancers, cervical surgery, in relation to neurological diseases such a cerebral palsy and in relation to anatomical abnormalities (bars/strictures). Esophageal body obstruction can also occur in relation to formation of strictures/webs which occlude the lumen. Regardless of the cause, the ability to identify the precise location of an obstruction may help guide interventions for obstruction (e.g. dilatation). In the pharynx, radiological imaging sometimes is unable to distinguish failure of UES opening due to obstruction vs failed UES opening to poor bolus propulsion.

One or more pressure-flow variables derived from the methods of the present invention may identify the precise location of an abnormality/inefficiency which is causing an obstruction. For example, contraction of the pharyngeal and/or esophageal lumen moves the bolus toward the stomach. The pressure and impedance characteristics of the contractile wave will vary at a point in the lumen where an obstruction is present. Accordingly, in one embodiment, one of the pressure flow variables is the maximum nadir of the impedance waveform preceding peak pressure (max Zn) in the pharynx and/or esophagus of the subject during clearance of the bolus from the mouth and/or throat of the subject.

As indicated above, this variable corresponds with when the lumen (pharynx or esophagus) is being maximally propelled (i.e. maximally distended/filled by the conductive bolus). At the point where the lumen being distended is focally narrowed/obstructed then the bolus volume within the narrowing is reduced thereby leading to the value of Zn recorded within the narrowing being higher (i.e. max Zn) than elsewhere in the lumen Mere no obstruction exists.

In some embodiments, one of the pressure-flow variables is the minimum impedance at the time of peak pressure (min ZPp) in the pharynx and/or esophagus of the subject during clearance of the bolus from the mouth and/or throat of the subject. As indicated above, this variable relates to the impedance in the pharyngeal and/or esophageal lumen during the contractile wave. At the point where the lumen being distended is focally narrowed/obstructed then the failure of a bolus to efficiently clear the pharyngeal and/or esophageal lumen at this point will result in a low ZPp value (i.e. min ZPp). Accordingly, the position of the min ZPp in the pharynx and/or esophagus of the subject is indicative of the position of the obstruction.

As indicated above, when the pharyngeal and/or esophageal lumen is physically obstructed the reduced cross-sectional area increases the value of Zn such that ZPp drops to below Zn. Therefore, the position of the maximum Zn/ZPp ratio as the bolus passes through the pharyngeal and/or esophageal lumen is indicative of the position of the obstruction. Accordingly, in some embodiments, the one or more pressure flow variables are the nadir of the impedance waveform preceding peak pressure (Zn) in the pharynx and/or esophagus of the subject during clearance of the bolus from the mouth and/or throat of the subject, and the impedance at the time of peak pressure (ZPp) in the pharynx and/or esophagus of the subject during clearance of the bolus from the mouth and/or throat of the subject, and wherein the position of the maximum Zn/ZPp in the pharynx and/or esophagus of the subject is indicative of the position of the obstruction.

In some embodiments, one of the pressure-flow variables is time from the nadir of the impedance waveform to the peak pressure (TNadImp-PeakP) in the pharynx and/or esophagus of the subject. If the lumen being distended is focally narrowed/obstructed then the rate of bolus flow through the narrowing is reduced. This leads to the value of TNadImp-PeakP becoming shorter within the narrowing hence allowing the position of an obstruction to be identified.

Although the inventor has found that min Zn, max ZPp, maximum Zn/ZPp and TNadImp-PeakP, are pressure-flow variables, or combinations of pressure-flow variables, which can enable the position of an obstruction to be identified in a subject, it is to be understood that the invention includes any other pressure-flow variable (or combination of pressure-flow variables) which is also altered in relation to obstruction (and which has been identified by the methods of the present invention), therefore identifying the position of an obstruction. Furthermore, it is to be understood that the methods of the present invention can also be applied to identify obstructions in other regions of the gastrointestinal tract, such as the upper esophageal sphincter, lower esophageal sphincter, pylorus, duodenum, jejunum, illeo-cecal junction and colon.

It will be understood by a person skilled in the art that various steps of the methods of the present invention may be performed in silico. For example, the intraluminal impedance and pressure measurements may be combined and analysed by a computer software program, which may also have the capacity to derive a value for one or more pressure-flow variables. The program may also include instructions for assessing swallowing motor function by performing a comparison between the value of the one or more pressure-flow variables with a predetermined pharyngeal and/or esophageal reference value for the one or more pressure-flow variables.

Accordingly, in a fourth aspect, the present invention provides software for use with a computer, the computer including a processor and associated memory for storing the software, wherein the software includes a series of instructions executable by the processor to carry out a method according to a first, second and/or third aspect of the present invention.

In a fifth aspect, the present invention provides a computer readable media containing software according to a fourth aspect of the present invention.

In a sixth aspect, the present invention provides an apparatus for enabling an assessment of swallowing motor function in a subject, the apparatus including:
  (a) a processor;
  (b) a memory; and
  (c) software resident in memory accessible to the processor, the software executable by the processor to carry out a method according to a first, second a nd/or third aspect of the present invention.

In a seventh aspect, the present invention provides a computer readable media including a set of instructions in the form of a computer software program, the instructions being executable by a processing device on-board a programmed computer, wherein execution of the instructions causes the programmed computer to:
  (a) accept, as an input, intraluminal impedance and pressure measurements obtained from the pharynx and/or esophagus of a subject during clearance of a bolus from the mouth and/or throat of the subject;
  (b) combine and analyse the intraluminal impedance and pressure measurements to derive a value for one or more pressure-flow variables in the pharynx and/or esophagus of the subject;
  (c) assess swallowing motor function in the subject by performing a comparison between the value of the one or more pressure-flow variables with a predetermined pharyngeal and/or esophageal reference value for the one or more pressure-flow variables; and
  (d) provide, as an output, an assessment of swallowing motor function in the subject on the basis of the comparison.

For example, execution of the instructions enables a computer process to proceed as follows. At the initiation of the computer process, intraluminal impedance and pressure measurements obtained from the pharynx and/or esophagus of the subject during clearance of a bolus from the mouth and/or throat of the subject are input. Input of the measurements can be performed manually by a user of the media, or the media itself may do this automatically once access to the measurements is enabled. The intraluminal impedance and pressure measurements are then combined and analysed to derive a value for one or more pressure-flow variables in the pharynx and/or esophagus of the subject. The value of the one or more pressure-flow variables is compared with a predetermined pharyngeal and/or esophageal reference value for the one or more pressure-flow variables, and an assessment of swallowing motor function in the subject is then made on the basis of the assessment. The assessment is provided as an output visible to a user of the media. The computer process then ends.

In one embodiment, the computer readable media further includes executable instructions which identify ineffective swallowing in the subject on the basis of the comparison. In some embodiments, the computer readable media further includes executable instructions which determine risk of aspiration in the subject, diagnose an increased likelihood of aspiration in the subject, predict aspiration in the subject, and/or identify a subject susceptible to aspiration. In some embodiments, the computer readable media further includes executable instructions which predict the occurrence of dysphagia in the subject following therapy and/or surgery. In some embodiments, the computer readable media further includes executable instructions which identify the position of an obstruction in the subject.

In an eighth aspect, the present invention provides a combination product, the combination product including:
  (a) a device for obtaining intraluminal impedance and pressure measurements from the pharynx and/or esophagus of a subject during clearance of a bolus from the mouth and/or throat of the subject; and
  (b) software according to a fourth aspect of the invention, an apparatus according to a sixth aspect of the invention, or a computer readable media according to a fifth or seventh aspect of the invention.

A device suitable for inclusion in the combination product according to the eighth aspect of the present invention is typically a catheter which incorporates both pressure sensors and impedance electrodes, as described above. It would be understood that the software, apparatus, or computer readable media may form an integral part of the device, or could be a separate entity to the device.

In some embodiments of the aforementioned aspects of the present invention, the subject is suspected to have dysphagia.

In some embodiments, the methods of the present invention may be useful for predicting curative therapy for aspiration or obstruction. For example, in the case of the pharynx, if the obstruction is localised to the upper esophageal sphincter, then this may contribute to aspiration. Knowledge of this may predict improvement with therapy (e.g. dilatation, myotomy, botox). In the case of the oesophagus, knowing the location of the obstruction allows the esophagus to be targeted by dilatation.

As used herein, the singular forms "a", "an" and "the" include plural aspects unless the context already dictates otherwise.

Where a range of values is expressed, it will be clearly understood that this range encompasses the upper and lower limits of the range, and all values in between these limits.

"About" as used in the specification means approximately or nearly and in the context of a numerical value or range set forth herein means±10% of the numerical value or range recited or claimed.

The present invention is further described by the following non-limiting examples. It is to be understood that the following description is for the purpose of describing particular embodiments only and is not intended to be limiting with respect to the above description.

Example 1

Assessment of Pharyngeal Motor Function Relevant to Aspiration—Adults

The aim of this study was to develop a new approach for the objective assessment of pharyngeal mechanical function relevant to aspiration. This used high resolution intraluminal manometry combined with impedance measurement (herein referred to as manometry and impedance). These data were explored for criteria that would enable recognition of individuals at high risk for clinically significant aspiration, without performance of fluoroscopy.

Methods

Subjects

Twenty subjects (13 male, mean 68.2 years, range 30-95 yrs) were studied. These subjects had been referred to a swallowing clinic for a videomanometric study of the pharynx and oesophagus because of clinical suspicion of deglutitive aspiration due to a deglutition disorder. Underlying diseases/conditions were identified through a review of medical records. The majority of subjects had a history of neurological disease or neurosurgery (FIG. 1). For comparison, ten healthy adult subjects (hereinafter "controls") were recruited who had no swallowing difficulties and did not display other symptoms suggestive of a motility disorder (5 male, mean 36.6 years, range 24-47 years). The study protocol was approved by the Research Ethics Committee, University Hospitals Leuven, Belgium.

Measurement Technique

Studies were performed in the Radiology Department, University Hospitals Leuven with a 3.2 mm diameter solid state manometric and impedance catheter incorporating twenty five 1 cm-spaced pressure sensors and 12 adjoining impedance segments, each of 2 cm (Unisensor USA Inc, Portsmouth, N.H.). Subjects were intubated after topical anaesthesia (lignocaine spay) and the catheter was positioned with sensors straddling the entire pharyngo-esophageal segment (velo-pharynx to proximal esophagus). Pressure and impedance data were acquired at 20 Hz (Solar GI acquisition system, MMS, The Netherlands) with the subject sitting. As per routine clinical fluoroscopy, test boluses of 5 and/or 10 ml liquid were administered orally via syringe. All bolus stock contained 1% NaCl. Video-loops of the fluoroscopic images of swallows were simultaneously acquired at 25 frames/second. The first swallow that followed bolus administration to the mouth was defined as the first swallow. If the first swallow failed to clear the bolus from the oral cavity, tongue-base, velleculae and/or piriform sinus, then the subject was asked to swallow again; these subsequent swallows were defined as clearing swallows. For controls, 8×10 ml liquid boluses were administered, 3 of these being recorded during fluoroscopy, which was the maximum allowed by the Research Ethics Committee, KU Leuven. The further 5 boluses were recorded with only manometry and impedance.

Fluoroscopic Assessment of Aspiration/Penetration

Fluoroscopic images from subject and control studies were scored for residue and for the occurrence of aspiration-penetration without knowledge of the manometric findings. However, the subject/control status of the studies was not blinded, because, to the experienced analyst, subject swallows were for the most part distinguishable from the swallows of the control group. Aspiration-penetration was assessed using a validated 8-point score (Rosenbek J C et al., 1996, Dysphagia 11(2):93-98), influenced primarily by the depth to which material passes in the airway and by whether or not material entering the airway is expelled during the swallow sequence (Score 1=no aspiration, 2-5=penetration, 6-8=aspiration). Swallows were also assessed dichotomously for the presence or absence of post-swallow residue in the valleculae, piriform sinus and/or posterior pharyngeal wall.

Data Analysis

Manometry and impedance recordings were combined so as to correlate precisely in time with fluoroscopic images. The combined recordings were analysed to derive four different pharyngeal pressure-flow variables indicative of timing and duration of maximal bolus flow, pressure during maximal bolus flow and pharyngeal contractile pressure. FIG. 2 illustrates manometry and impedance recordings represented as respective waveforms (FIGS. 2A and 2B), which when combined (FIG. 2C) delineate the four pharyngeal pressure-flow variables. Derivation of the variables is described in detail below.

Raw manometric and impedance data for each fluoroscopically observed swallow were exported from the recording system in ASCII text format and then analysed by a separate computer using MAT LAB (version 7.9.0.529; The MathWorks Inc). Pressure and impedance data were smoothed by a cubic interpolation method which doubled the temporal data and increased the amount of spatial data by a factor of 10 (pressure) and 20 (impedance), hence achieving a virtual increase from 1 pressure and 0.5 impedance values per 1 cm sampled every 5 msec (20 Hz) to 10 pressure and impedance values per cm sampled every 2.5 msec (40 Hz). Given that baseline levels of impedance vary greatly along the pharyngo-esophageal segment due to variability of mucosa to electrode contact and the presence of secretion or residue, the standard approach to impedance analysis (time below/above variably defined thresholds relative to baseline) is very unreliable. A new method of impedance analysis was developed which analysed the shape of the impedance waveform (as shown in FIG. 2), rather than the magnitude of impedance change. In order to do this reliably, the raw impedance data were standardised to the median impedance (presented therefore as median standardised units (msu) rather than ohms).

Pharyngeal Pressure-Flow Variables

From the pressure colour iso-contour plot (FIG. 3A), two regions of interest (ROI) were defined. The $1^{st}$ ROI demarcated the extent of the entire pharyngeal stripping wave for assessment of pressures along and relative to the stripping wave (see below). The $2^{nd}$ ROI defined the region of the pharynx distal from the tongue base and was used to determine the pattern of impedance drop and recovery as a marker of bolus presence in the distal pharynx (see below).

$1^{st}$ Region of Interest Analysis

Figure 3:
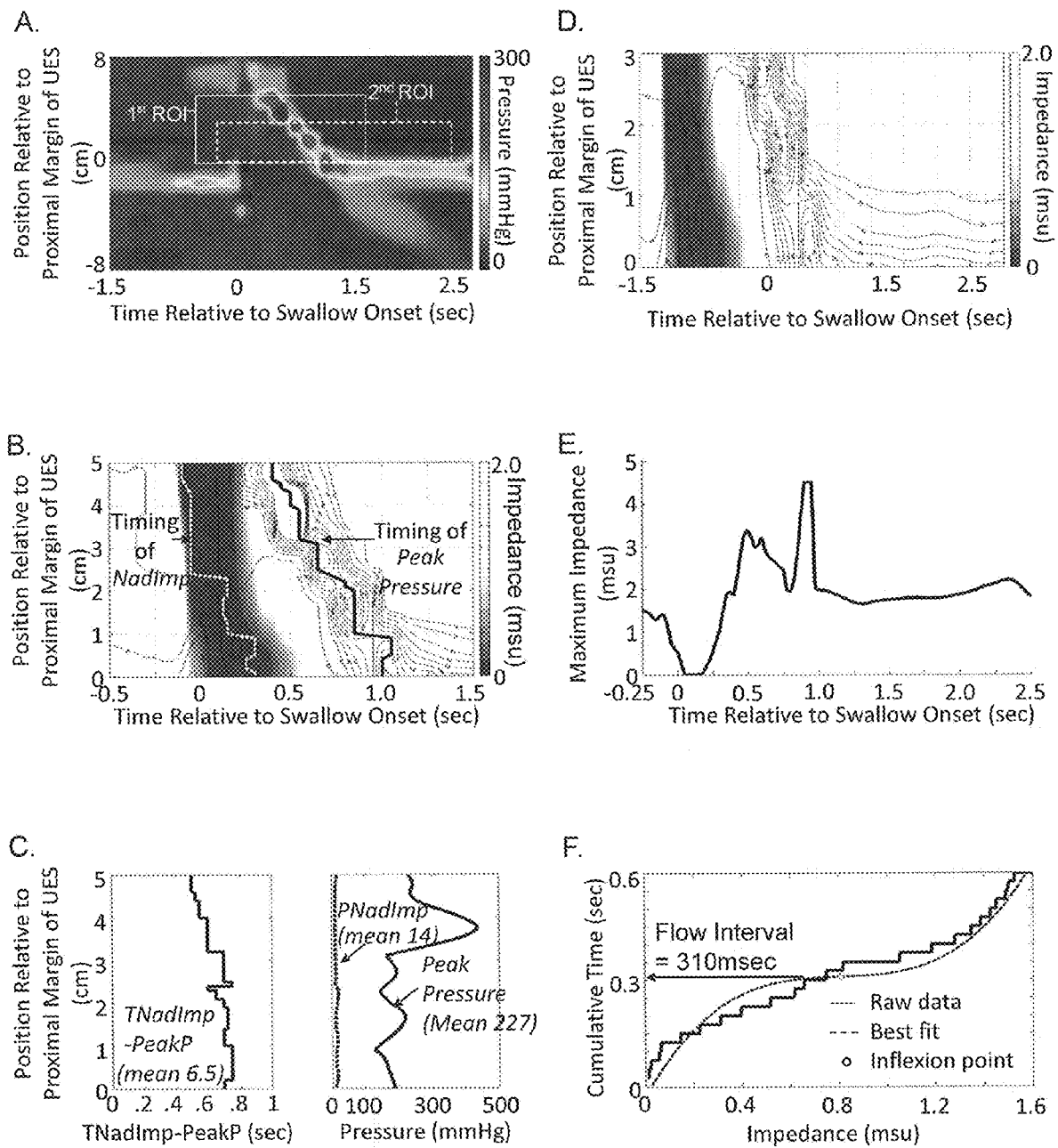
FIG. 3 shows a series of iso-contour plots and graphs summarising how the impedance and pressure measurements were analysed to calculate the pharyngeal pressure-flow variables PNadImp, PeakP, TNadImp-PeakP and Flow Interval. (A) A pressure colour iso-contour plot showing a first region of interest ($1^{st}$ ROI) used to calculate PNadImp, PeakP and TNadImp-PeakP, and a second ROI ($2^{nd}$ ROI) used to calculate Flow Interval. (B) Pressure impedance iso-contour plot for the $1^{st}$ ROI showing the timing of pharyngeal nadir impedance and PeakP. (C) Graphical plots of TNadImp-PeakP, PNadImp and PeakP with average values shown. (D) Pressure impedance iso-contour plot for the $2^{nd}$ ROI. (E) A graphical plot of maximum impedance (along y-axis of $2^{nd}$ ROI) over time (x-axis of $2^{nd}$ ROI). (F) Impedance cumulative time plot (derived using data in D) showing raw data, the third-order polynomial best fit and the inflexion point of the best fit curve used to define the Flow Interval.

The $1^{st}$ ROI encompassed the spatial region from velopharynx to the proximal margin of the UES high pressure zone and the time interval from 0.5 sec before to 1.0 sec after swallow onset (FIGS. 3A and 3B). The timings of the pharyngeal impedance nadir (NadImp) and peak pressure (PeakP) were determined (FIG. 3B) at all positions along the 1$^{st}$ ROI. The average pressure at NadImp (average PNadImp), average PeakP and average time delay from NadImp to peak pressure (average TNadImp-PeakP) for the 1$^{st}$ ROI (FIG. 3C) were then calculated from these point data.

2$^{nd}$ Region of Interest Analysis

The 2$^{nd}$ ROI encompassed the pharyngeal stripping wave from tongue-base to proximal margin of the UES high pressure zone; measurements were analysed from 0.25 sec before to 2.5 sec after swallow onset (FIGS. 3A and 3D). The interval/duration of impedance drop (Flow Interval) within the ROI was determined with a method based on one previously described for measurement of UES relaxation interval from pressure values recorded in the region of the UES high pressure zone (Ghosh S K et al., 2006, *Am. J. Physiol. Gastrointest. Liver Physiol.*, 291: 525-531).

The maximum impedances within the 2nd ROI were measured at all time points and plotted spatially (FIG. 3E). An impedance vs cumulative time plot was derived by progressively increasing impedance thresholds from 0-2 msu in steps of 0.01 msu and determining the amount of time that the impedance was below each step level (FIG. 3F), this plot was then mathematically described using third-order polynomial equation (the typical equation for a curve with one inflexion). The cumulative time of the inflexion point of a smoothed best-fit curve was used to objectively calculate the flow interval (FIG. 3F).

UES Relaxation Variables

UES relaxation characteristics were measured using the established method of Ghosh S K et al., 2006 (supra) which objectively calculated UES relaxation interval (UES-RI), the UES nadir relaxation pressure (NadUESP), the median intrabolus pressure (median UES-IBP) and the UES resistance (calculated as NadUESP/UES-IBP).

Statistical Analysis

Non-parametric grouped data were presented as medians (inter-quartile range) and compared using the Mann-Whitney Rank Sum Test. For multiple comparisons Kruskal-Wallis ANOVA on ranks with pair-wise multiple analysis procedures (Dunn's method) was used. Correlation was determined using Spearman Rank Order Correlation. The association of variables with presence of aspiration was also assessed using Multiple Logistic Regression and ANOVA with Odds Ratio (95% CI). The sensitivities and specificities were determined for the different objective variables to detect of fluoroscopically defined aspiration. The level of concordance between criteria and the presence of aspiration was also expressed with Cohen's kappa Statistic. The scale for kappa values is: 0.00=no agreement, 0.00-0.2=slight, 0.21-0.40=fair 0.41-0.60=moderate, 0.61-0.8=substantial, 0.81-1.00=almost perfect. For all tests a p<0.05 indicated statistical significance.

Results

In the subjects, 54 first swallows were evaluated with the three modalities of fluoroscopy, manometry and impedance. Of these, 28 swallows (in 17 subjects) failed to clear the bolus fully and in these subjects a further 40 clearing swallows were recorded. Deglutitive aspiration was observed during a total of 35 swallows comprising 14 first and 21 clearing (in 13 subjects). The median [IQR] aspiration score was 7 for these aspiration-associated swallows [5, 8]. Clearance failure was a weak risk factor for aspiration (odds ratio 1.24 [1.04, 1.48], p<0.05).

In controls, 26 first swallows were evaluated with the three modalities, and 47 were recorded without fluoroscopy. Of fluoroscopically recorded swallows, 8 (in 4 controls) exhibited trace amounts of residue and therefore failed to clear. Deglutitive aspiration-penetration was never observed during any fluoroscopically recorded control swallows.

First Swallows: Controls vs Patients

Figure 4:
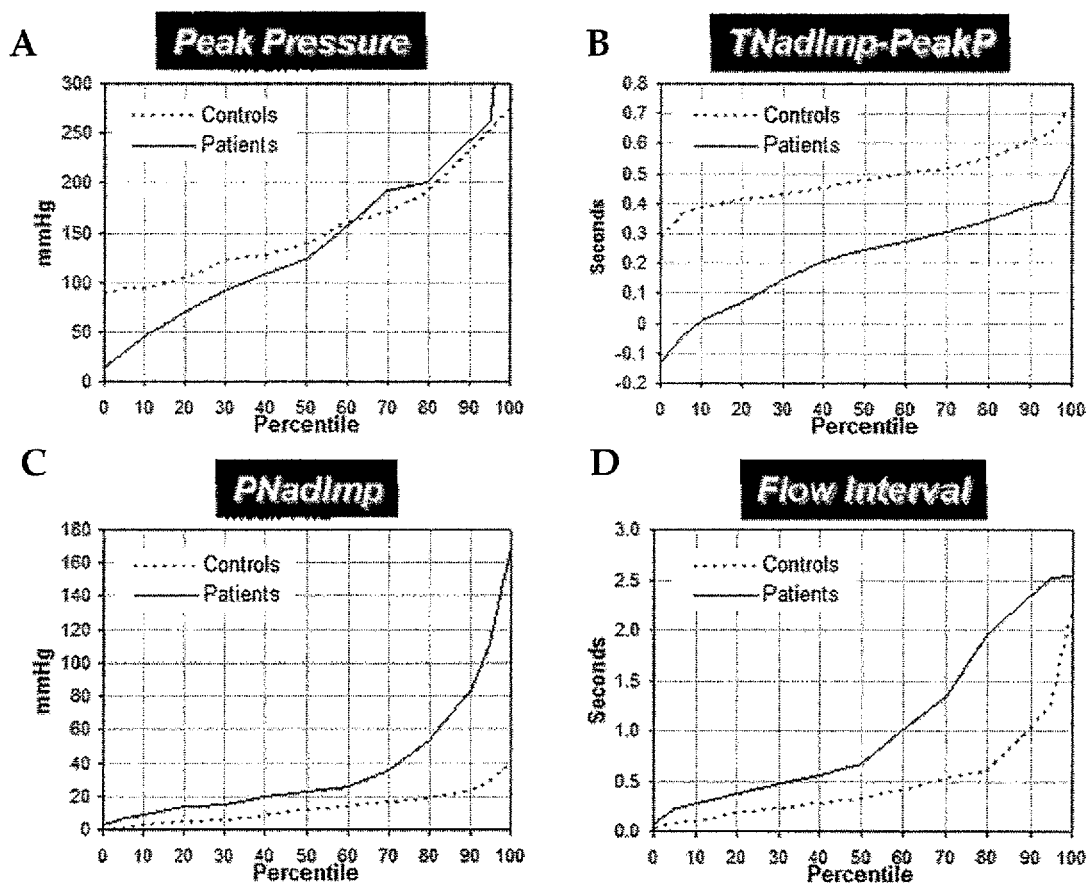
FIG. 4 shows graphs summarising results of the analysis of combined impedance and pressure measurements and the pressure-flow variables that were significantly different in subjects compared to controls. (A) Peak Pressure (PeakP); (B) TNadImp-PeakP; (C) PNadImp; and (D) Flow Interval.

Percentile charts for four swallow variables (based on First swallows) are shown in FIG. 4. Reference ranges (5th-9th percentile) for variables based on these charts are PNadImp: 0-26 mmHg; PeakP: 93-255 mmHg; TNadImp-PeakP: 371-640 msec, and Flow Interval: 100-1250 msec. For first swallows, UES-IBP and NadUESP were the only variables that were not significantly different in subjects compared to controls (Table 1). Patient first swallows with aspiration had a lower PeakP, longer Flow Interval, shorter TNadImp-PeakP and longer UES-RI than those without aspiration (Table 1; and FIGS. 4A, 4B and 4C). Patient first swallows with residue had a longer Flow Interval than those without residue (1290 [580, 2300] vs 490 [320, 1120] msec respectively, p=0.008). Other first swallow variables were not different in relation to the presence/absence of residue.

TABLE 1

|  | CONTROLS All First Swallows | PATIENTS | | |
|---|---|---|---|---|
|  |  | All First Swallows (p-value vs CONTROL) | First Swallows WITHOUT Aspiration | First Swallows WITH Aspiration (p-value vs NO Asp) |
| No. Swallows Analysed | 72 | 54 | 40 | 14 |
| PeakP mmHg | 138 [110, 178] | 99 (<0.001) [66, 163] | 118 [72, 193] | 72 (0.018) [28, 111] |
| P NadImp mmHg | 12 [5, 17] | 21 (<0.001) [13, 36] | 24 [14, 53] | 21 (0.547) [13, 34] |
| Flow Interval msec | 320 [210, 590] | 800 (<0.001) [470, 2090] | 640 [340, 1300] | 1980 (0.001) [1170, 2530] |
| TNadImp-PeakP msec | 320 [210, 590] | 190 (<0.001) [30, 300] | 260 [100, 350] | 50 (0.006) [20, 160] |
| UES-RI msec | 520 [400, 580] | 1030 (<0.001) [750, 1300] | 980 [660, 1220] | 1250 (0.015) [900, 1970] |
| UES-IBP mmHg | 12 [6, 20] | 13 (0.311) [9, 22] | 10 [6, 24] | 14 (0.453) [9, 22] |
| NadUESP mmHg | 6 [1, 13] | 5 (0.627) [2, 10] | 5 [2, 10] | 5 (0.898) [0, 13] |
| UES resistance mmHg/sec | 22 [11, 41] | 13 (0.012) [8, 25] | 14 [10, 26] | 9 (0.082) [4, 24] |

Summary data of 126 first swallows in controls and patients showing the relationships among important objective variables (pharyngeal variables shaded) and the presence of aspiration-penetration. Data presented as median [IQR]. P-values of Mann-Whitney Rank Sum Test for control vs patient and no aspiration vs aspiration shown in parentheses. Data for which p < 0.05 highlighted in bold text.

Fluorscopically recorded control first swallows with residue had higher Peak Pressures (183 [137, 246] vs 116 [95.6, 1334] mmHg respectively, p=0.01) and longer PNad Imp-PeakP (0.47 [450, 510] vs 400 [370, 450] msec respectively, p=0.01) than those without residue. The Flow Interval was not different during swallows with residue (320 [230, 560] vs 300 [210, 380] msec respectively, p=0.483), neither were other first swallow variables, however, we noted that the variables most likely to be influenced by UES resistance were all evaluated in relation to residue (PNadImp 17 vs 6 mmHg, p=0.162; UES-IBP 13 vs 21 mmHg, p=0.091; NadUESP 16 vs 8 mmHg, p=0.128; UES resistance 42 vs 25 mmHg/sec, p=0.162).

Clearing Swallows: Subjects

Clearing swallows in subjects with aspiration had a longer Flow Interval than those without aspiration (2400 [2120, 2540] vs 450 [380, 930] msec respectively, p<0.001). No other clearing swallow variables were significantly different in relation to aspiration.

Subject clearing swallows with residue had a longer Flow Interval than those without residue (2240 [860, 2520] vs 440 [390, 2060] msec respectively, p=0.022). Clearing swallows with residue also had a higher UES-IBP (20 [10, 28] vs 12 [4, 20] mmHg respectively, p=0.047), a higher NadUESP (10 [5, 14,] vs 2 [1, 6] mmHg respectively, p=0.007) and higher DSR (26 [12, 34] vs 14 [6, 21] mmHg/sec respectively, p=0.049). PeakP, PNadImp, TNadImp-PeakP and UES-RI were not significantly different in relation to residue.

Derivation of the Swallow Risk Index Having observed that swallows in subjects with suspected aspiration have lower PeakP, higher PNadImp, longer Flow Interval and shorter TNadImp-PeakP than asymptomatic controls, we derived a swallow risk index (SRI) based on the following formula:

$$SRI = \frac{(\text{Flow Interval} * PNadImp)}{(\text{Peak Pressure} * (PNadImp - PeakP + 1))} * 100$$

Figure 5:
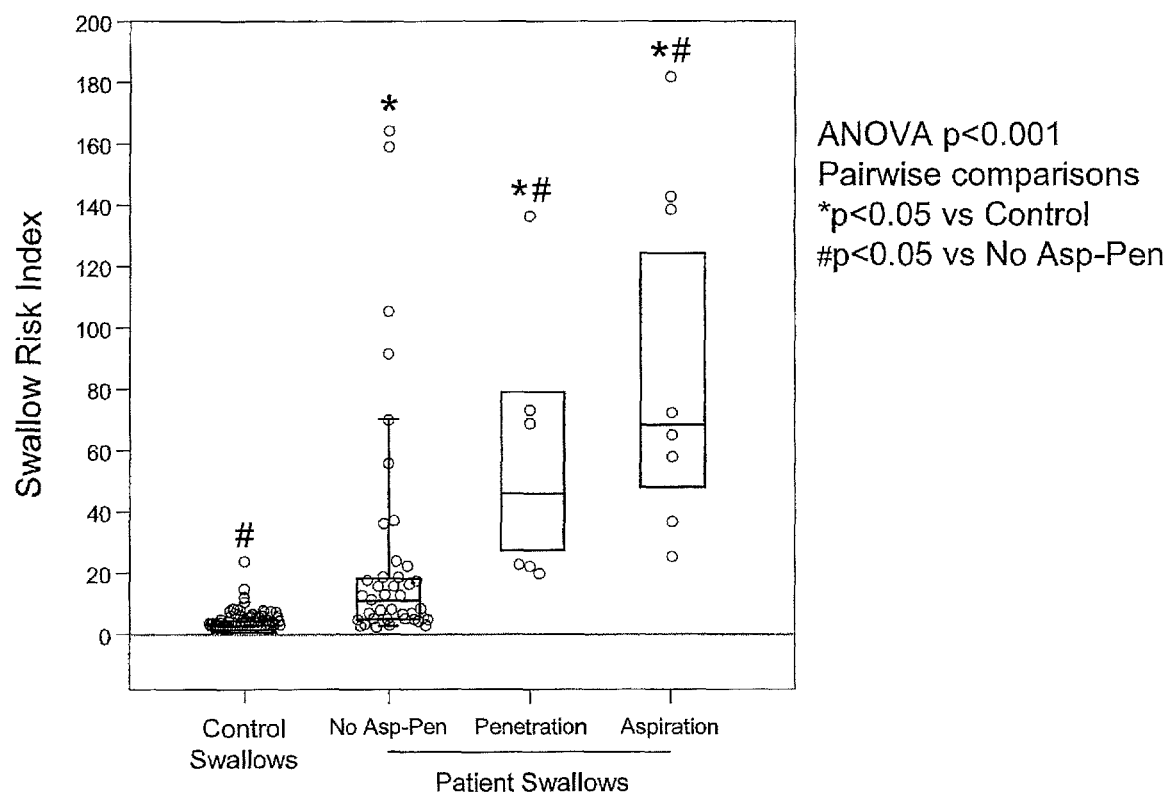
FIG. 5 is a box plot showing median and inter-quartile ranges for first swallow SRI in controls and subjects. Subject data are further stratified based on aspiration score. No aspiration=score 1, penetration=score 2-5 and aspiration=score 6-8. Grey circles show the data from individual swallows. Groups were compared using Kruskal-Wallis One Way Analysis of Variance on Ranks and Pairwise Multiple Comparison Procedures (Dunn's Method).

The overall median SRI for first swallows was significantly elevated in subjects compared to controls (17.4 [5.7, 59.6] vs 1.7 [0.6, 3.7] respectively, p<0.001). Amongst swallows from the subject cohort, the median SRI's for swallows during which no aspiration was observed were lower compared to swallows with aspiration (First swallow SRI 11.9 [3.9, 21.3] without aspiration vs 66.8 [24.6, 136.8] with aspiration, p<0.001; Clearing swallow mean SRI was 22.4 [10.5, 56.3] without aspiration vs 64.9 [35.7, 105.2] with aspiration, p<0.01). Logistic regression also revealed that the odds ratio for the correlation of aspiration with SRI was 8.1 [2.0, 32.6] (p=0.003) for first swallows and 19.6 [2.3, 164.8] (p=0.006) for clearing swallows. The SRI increased significantly in line with increased severity of aspiration as is shown in FIG. 5 for first swallows. The median SRI also differentiated clearing swallows with penetration (22.4 [10.5, 56.3]) and aspiration 79.1 [49.3, 107.3], from clearing swallows with no aspiration (15.7 [5.8, 89.8]) (ANOVA p=0.002, pair wise p<0.05 aspiration vs no-aspiration). Bolus volume had no significant effect on the SRI (First swallow SRI 23.0 [6.8, 72.4] vs 15.9 [3.6, 24.6], p=0.169 and clearing swallow SRI 56.3 [22.4, 91.4] vs 24.6 [12.8, 78.1], p=0.267 for 5 ml and 10 ml boluses respectively).

Predictive Value of First Swallow SRI

Figure 6:
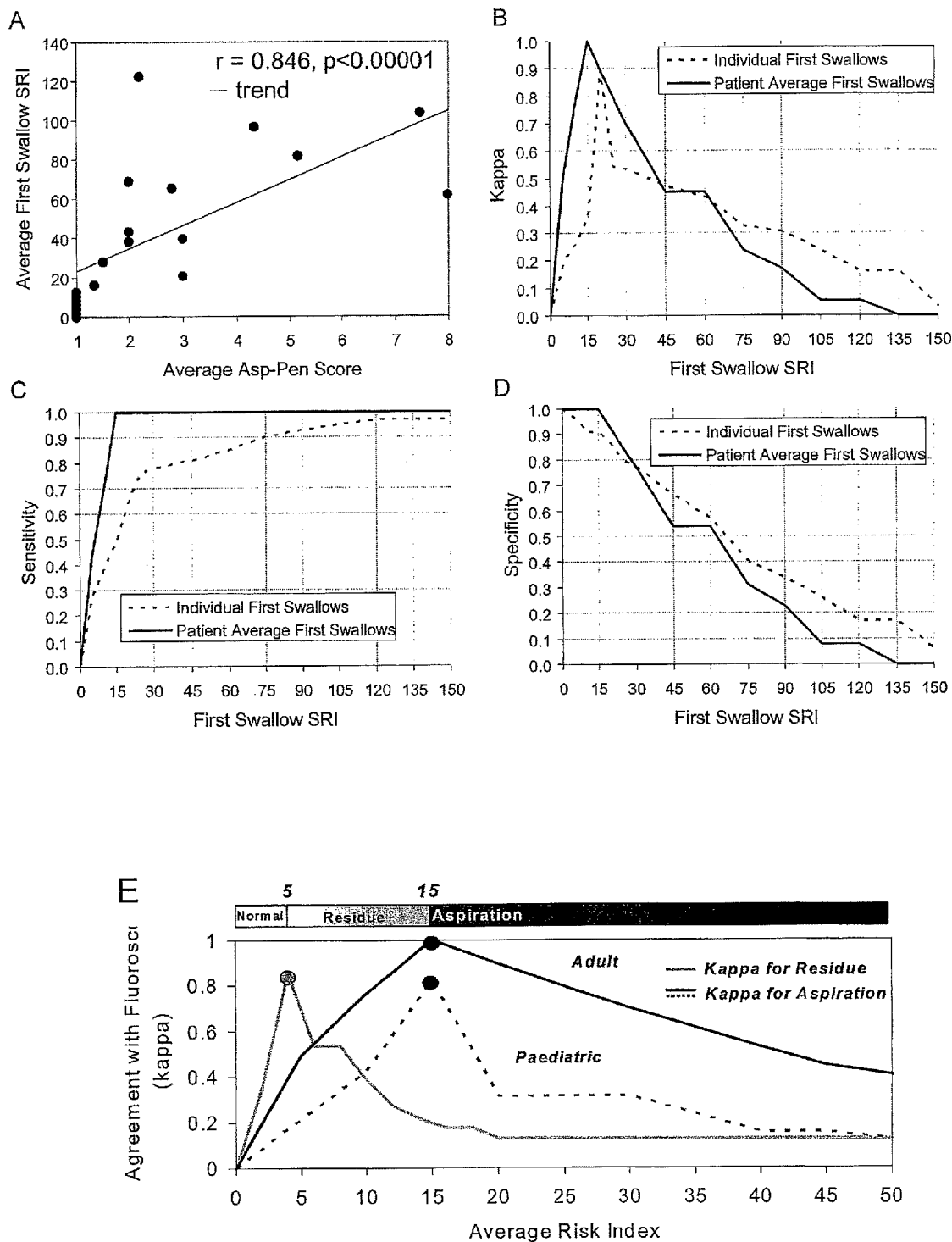
FIG. 6 shows graphs which establish that the first swallow SRI recorded in an individual subject can predict presence or absence of aspiration during fluoroscopy. (A) Correlation of patient average aspiration score with average first swallow SRI. (B) Kappa agreement between individual and average first swallow SRI cut-off values and the presence/absence of aspiration-penetration during fluoroscopy. Sensitivity and specificity curves for individual and average first swallow SRI are shown also in graphs C and D respectively. (E) Kappa agreement showing that a lower cut-off of SRI exhibited utility for defining post-swallow residue.

An assessment was performed to establish whether the first swallow SRI recorded in an individual subject could predict the presence/absence of aspiration during fluoroscopy. The average first swallow SRI correlated strongly with the average aspiration score for all fluoroscopically recorded swallows (Spearman Rank Order Correlation of 0.846, p<0.00001) (FIG. 6A). An average first swallow SRI of 15.0 was a perfect threshold for accurate prediction of aspiration in the patient cohort (FIG. 6B) and was also optimal in terms of sensitivity and specificity (FIGS. 6C and 6D) and Kappa (6E). As shown in FIG. 6E a lower cut-off of SRI exhibited utility for defining post-swallow residue.

Discussion

A novel automated approach to the analysis of pharyngeal manometry and impedance recordings was used to identify subjects with deglutitive penetration-aspiration. A swallow risk index was developed that is based upon the objective calculation of four pharyngeal pressure-flow variables. This new methodology is capable of identifying individual patients at deglutitive aspiration risk without use of fluoroscopy. The approach is based on the premise that the pathophysiology of deglutitive aspiration is multi-factorial. Hence, prediction of deglutitive aspiration risk requires the measurement of pressure and flow with high spatial resolution along the entire pharynx and the derivation of measures that assess the timing of bolus propulsion (TNadImp-PeakP), pressure during bolus flow (PNad Imp), peak pharyngeal pressure and pharyngeal flow interval.

Previous approaches to the evaluation of the mechanics of pharyngeal bolus flow with pressure/impedance have only been partially successful. These prior studies concentrated on optimising impedance-based criteria, but the interpretation of the impedance signal is especially difficult in patients with suspected aspiration-penetration, because of pooling of secretions and altered motor function. The data presented above shows that incomplete pharyngeal emptying (i.e. residue after an initial swallow) is a relatively insensitive test on its own for patterns of motor function that result in aspiration-penetration (odds ratio 1.240, p<0.05). Indeed, pharyngeal/UES motor function does not always empty the pharynx in healthy subjects, as the data from the control subjects presented above shows. The limitations of impedance recording have been addressed by the present study by strategies that extract more reliable information from the impedance signal, which was then used to guide the analysis of pharyngeal pressures. This approach achieved a more direct measure of the spatial organisation of pharyngeal motor function. This contrasts with the standard approach which evaluates impedance and pressure findings separately.

The combined manometry and impedance recordings were evaluated with auto mated analysis algorithms which derived the variables presented above. The entire impedance signal during swallowing was also analysed automatically and processed in a way that reduced noise. This is a novel approach to evaluation of impedance signals which are usually scored according to periods of time during which impedance is above or below a certain cut-off value. Interestingly, the flow interval for first swallows was not elevated in relation to the presence of residue in controls, and, whilst elevated with residue in affected subjects, correlated more strongly with aspiration-penetration (OR 3.3 [1.5, 7.4], p=0.004) than bolus residue (OR 2.4 [1.1, 5.2, p=0.021), suggesting that the flow interval is a very useful single measure of deglutitive function/dysfunction.

Figure 7:
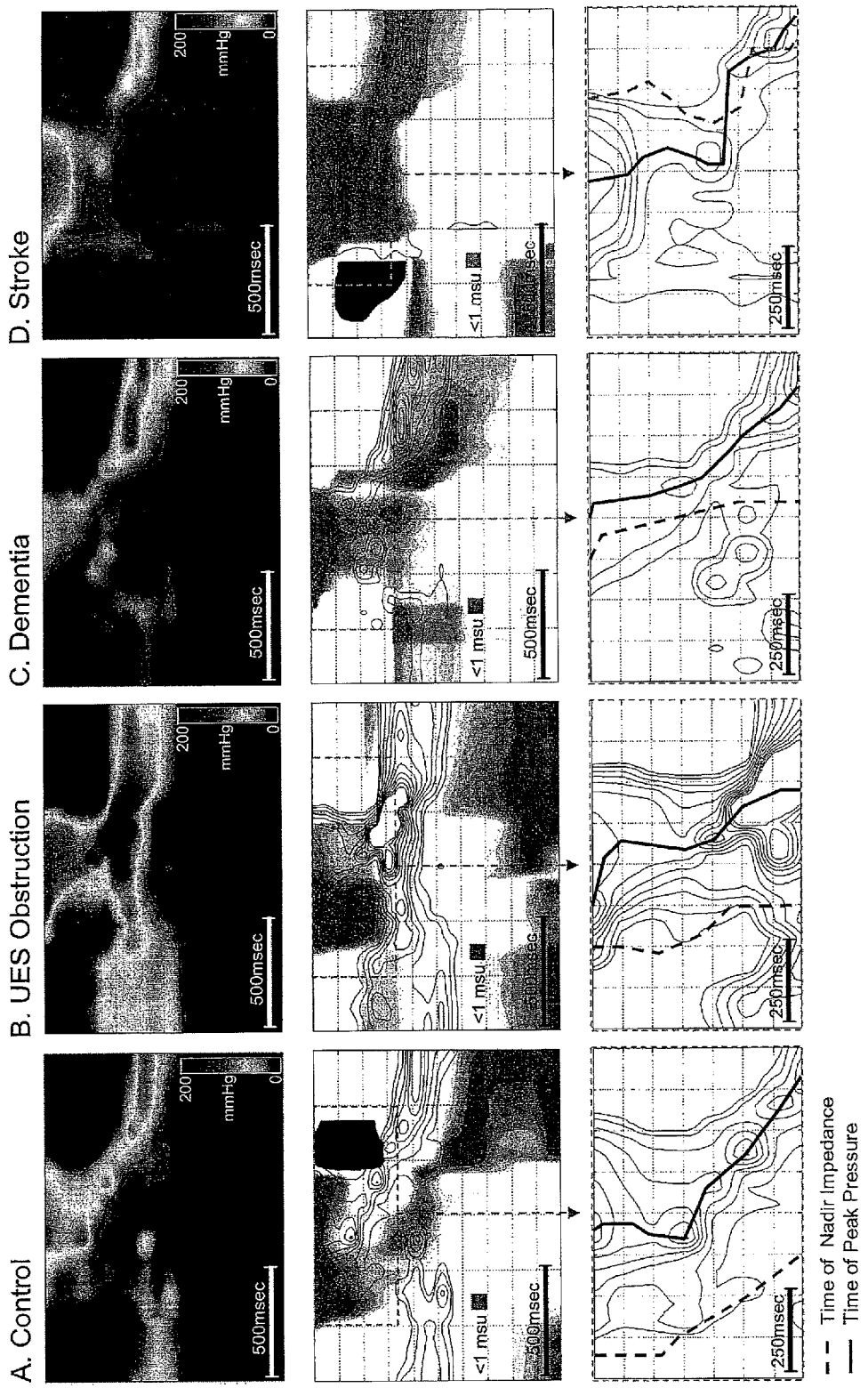
FIG. 7 provides a series of iso-contour plots showing that the pattern of abnormal pharyngeal and UES motor function in subjects varies with different pathologies that produce obstruction or weakness. Example tracings of first swallows (10 ml liquid) recorded in a control subject are shown in relation to three different pathologies (individual results for pharyngeal variables and aspiration-penetration scores are shown in FIG. 8). (A) A 39 year old asymptomatic male control. (B) A 58 year old man who developed symptoms post anterior cervical fusion (C5-C6) surgery in whom fluoroscopy demonstrated high obstruction and no evidence of aspiration (aspiration-penetration score 1). (C) An 88 year old man with Dementia (Alzheimer's) and intermittent signs of aspiration on liquids in whom fluoroscopy demonstrated penetration (aspiration-penetration score 2). (D) A 57 year old stroke patient (male, right hemisphere) who had continuous signs of aspiration on liquids and in whom fluoroscopy demonstrated aspiration (aspiration-penetration score 7). Top row: iso-contour plots of pressure only. Second row: Pressure-impedance iso-contour plots showing pressure as lines (10 mmHg iso-contours) with impedance superimposed (iso-contour showing impedance levels <1 msu). Iso-contour plots of pressure within the dotted box are in the Third Row. In these plots dotted and solid lines define the timing of NadImp and the timing of peak pressure respectively.
Figure 8:
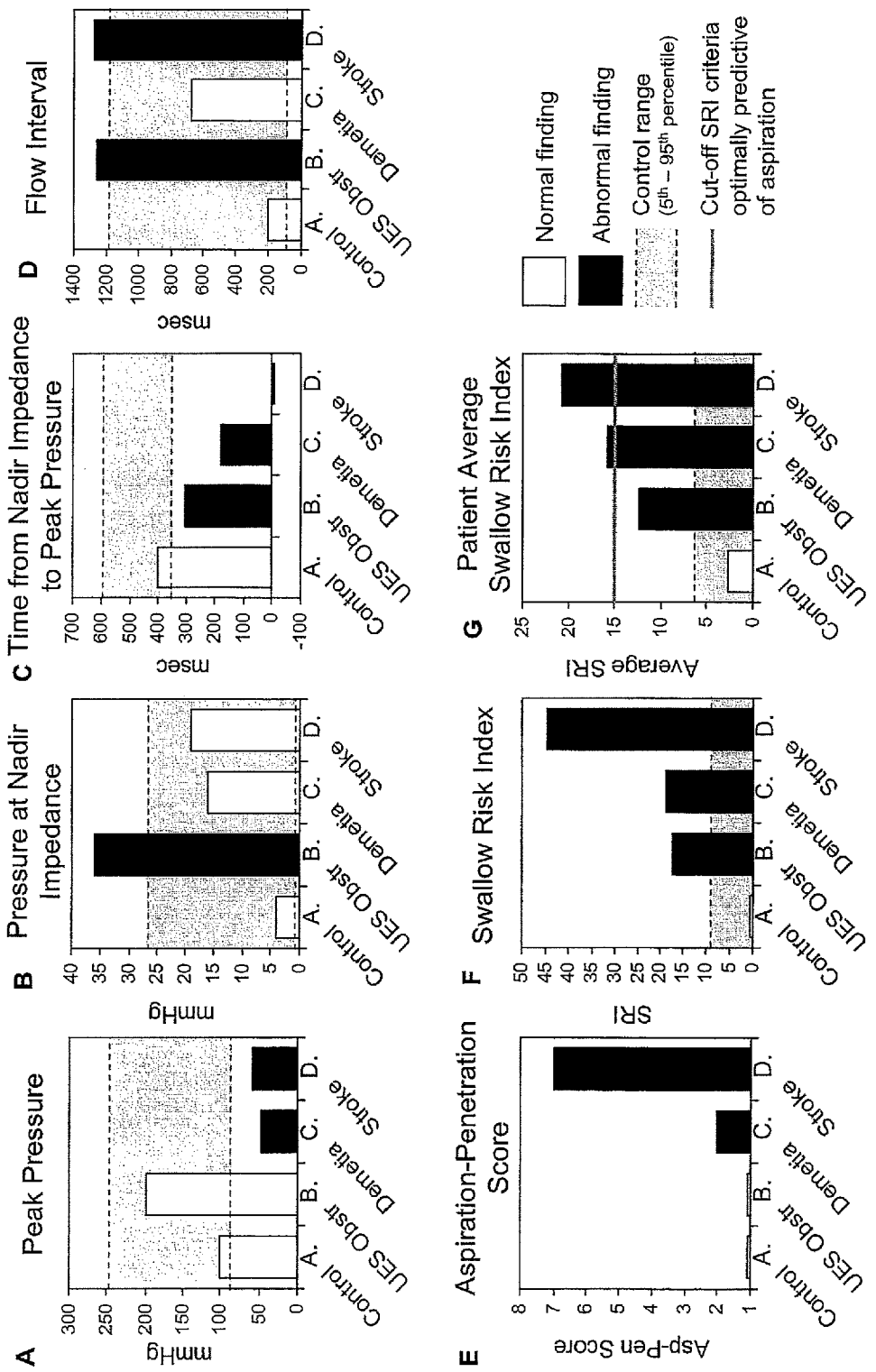
FIG. 8 provides graphs summarising a comparison of pharyngeal variables and aspiration-penetration scores for the four subjects for which data from sample individual swallows are shown in FIG. 7. Individual data for PeakP, PNadImp, TNadImp-PeakP, Flow Interval, aspiration-penetration score and SRI are shown, as is the patient average SRI for all (3-5) first swallows in each subject. Control ranges for each variable are shown by grey shading; abnormal findings compared to controls are indicated as black bars. For graphs comparing subject average SRI, the grey line indicates the optimal cut-off criteria.

However, flow interval alone cannot in itself diagnose the cause of dysfunction, hence the importance of inclusion of other direct measures. As illustrated in FIGS. 7 and 8, the pattern of abnormal pharyngeal and UES motor function in subjects varies with different pathologies that produce obstruction or weakness. For example, obstruction subject B, compared to dementia and stroke subjects C and D, had a normal PeakP but elevated PNadImp. Stroke subject D had a mean TNadImp-PeakP<0 (i.e. on average nadir impedance occurred after peak pressure) this is suggestive of highly ineffective bolus propulsion in advance of the pharyngeal stripping wave. Dementia and stroke subjects C and D had the highest SRI, consistent with fluoroscopy findings of penetration and aspiration respectively.

Because the SRI takes into account several different measures of function, it delivers an accurate assessment of aspiration risk regardless of the pattern of functional impairment. Recognition of particular patterns of impairment of pressure-flow variables should allow a relatively specific diagnosis of varying swallow mechanical dysfunctions that result in aspiration. From such analysis, it may be possible to devise well targeted therapeutic interventions.

The automated and objective methods used for deriving pharyngeal pressure-flow variables is a major strength of this study. Though these methods are complex in themselves, they are simple to apply, since the operator only needs to define the region of interest on the specially developed analysis system. This new method receives the data directly from high resolution manometric systems as text, a standard output of such equipment.

This study also evaluated UES relaxation pressure-time variables (UES-RI, NadUESP, UES-IBP and UES resistance). Whilst UES-RI and UES resistance were significantly different in our subjects, only UES-RI was significantly altered in relation to the presence of aspiration-penetration. This is an interesting finding, given that the most frequently used interventions for aspiration, UES myotomy and Botulinum toxin injection, are aimed at weakening the UES. Such interventions are however known to have inconsistent efficacy in subjects with CNS damage who represent the majority of the subjects in our study cohort. Undoubtedly there are subjects who have problems with aspiration-penetration because of impaired UES opening, but these were not well represented in the cohort.

In the present study, the analysis of a large number of variables recorded with very high time resolution from the manometric and impedance tracings would have been impossible without automation. This wealth of variables that were measured allowed the exploration of which combinations of variables were most effective for identifying subjects with aspiration-penetration, hence the derivation of the SRI. The results of the present study showed that average data from as few as 3-5 first swallows are sufficient for determining a reliable estimate of a subject's aspiration risk.

The present studies were all performed using topical anaesthesia. Topical anaesthesia is important for providing a level of comfort so that the procedure can be performed quickly and effectively. Used judiciously, mucosal anaesthesia appears to have had no effect on the outcomes, given the large differences seen between subjects and controls and swallows with or without aspiration. Other possible factors that may have influenced our findings are the fact that our control group were relatively young compared to the subject group. This is relatively unimportant as our major analysis and conclusions with respect to aspiration are based upon exploration of data from subjects only. The subject cohort of the present study predominantly had neurological diseases but was nevertheless varied and included subjects with a wide age range. The subjects were studied prospectively as they were referred for investigation and therefore there was no control over which subjects were to be investigated in the present study. This study design means that the cohort is typical of the overall population of subjects in whom aspiration is suspected on clinical grounds.

The fact that the predictive value of the SRI appears to be robust in the face of the potential confounding factors discussed immediately above engenders confidence that this methodology has very real potential for clinical implementation as a screening tool for aspiration risk. There are many populations at risk for aspiration-penetration, such as post-stroke subjects, subjects with diverse neurological and muscle diseases or those who have had pharyngeal or neurological surgery. These subjects are well represented in the study cohort and demonstrated elevated SRI in relation to aspiration. These subjects are most often not investigated by fluoroscopy until they demonstrate clinical signs and symptoms of aspiration. The value of using this methodology as a screening tool to trigger early intervention requires further investigation by way of outcome studies to determine if, for example, SRI predicts clinical deterioration and what interventions are of most value.

In conclusion, the present study provides novel findings in control subjects and in a cohort of subjects with predominantly neurological problems who were referred for investigation of suspected aspiration. These show that combined high resolution solid state manometry and impedance recordings can be objectively and automatically analysed to derive robust multiple pressure-flow variables that are altered in relation to pathology. Importantly a swallow risk index can be derived through the combination of these pressure-flow variables and used to predict circumstances when aspiration is likely.

Example 2

Assessment of Pharyngeal Motor Function Relevant to Aspiration—Children

The aim of this study was to apply the approach developed in Example 1, i.e. the use of high resolution intraluminal manometry combined with impedance measurement, for the objective assessment of pharyngeal function relevant to aspiration in infants and children. This approach was evaluated to determine if it enables recognition of paediatric patients at high risk for clinically significant aspiration, without performance of fluoroscopy.

Methods

Subjects

Figure 9:
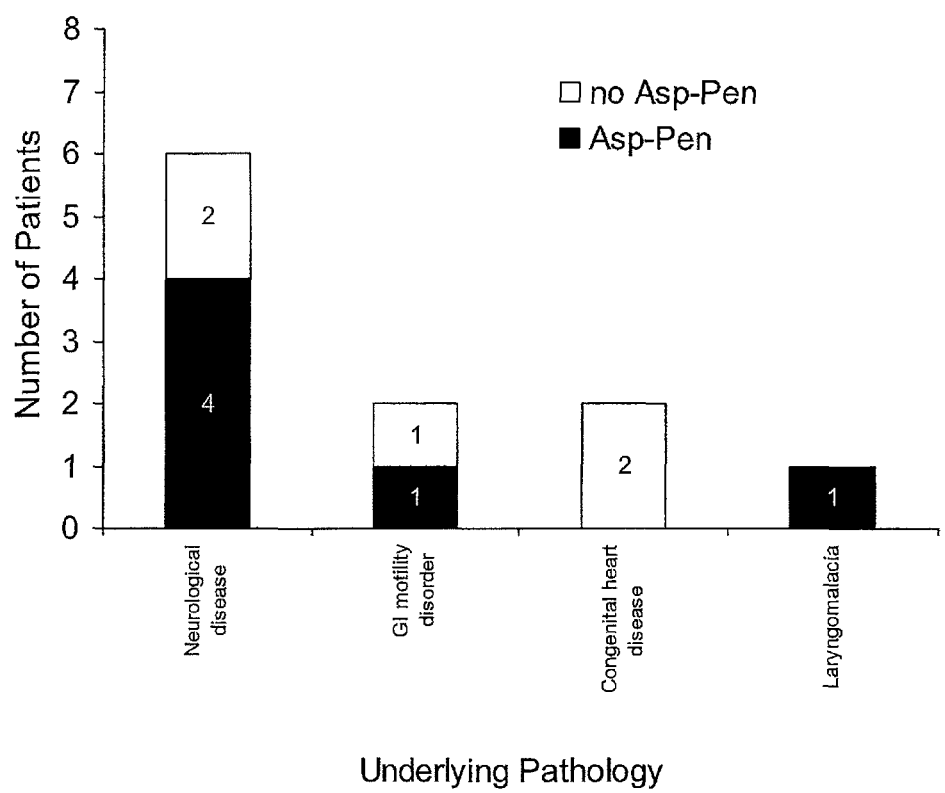
FIG. 9 is a graph summarising the paediatric patient cohort used for the studies described in Example 2. The graph shows the underlying medical pathology and presence of aspiration-penetration detected on video fluoroscopy.

Eleven paediatric dysphagic patients (mean 6 years, range 5 months-13.4 years) we re referred for a videomanometry study of the pharynx and esophagus. Underlying diseases/conditions were identified through a review of medical records. The majority of patients had a neurological history (FIG. 9).

Measurement Technique

All fluoroscopy studies were performed in the Paediatric Radiology Department, University Hospitals Leuven. Studies were performed using a 3.2 mm diameter solid state manometric and impedance catheter incorporating twenty five 1 cm-spaced pressure sensors and twelve 2 cm long impedance segments (Unisensor USA Inc, Portsmouth, N.H.). Subjects were intubated with topical anaesthesia (lignocaine gel) used to reduce discomfort and the catheter was positioned with sensors straddling the entire pharyngo-esophageal segment (velo-pharynx to proximal esophagus). Pressure and impedance data were acquired (upright position) at 20 Hz (Solar GI acquisition system, MMS, The Netherlands). As per routine clinical fluoroscopy, test boluses of 1-10 ml liquid (dependent on age and tolerance) were administered orally via syringe. All bolus stock contained 1% NaCl to improve bolus conductivity. Video-loops of the fluoroscopy images of swallows were simultaneously acquired (25 frames/sec). The first swallow that followed bolus administration to the mouth was defined as the first swallow. If the first swallow failed to clear the bolus from the oral cavity, tongue-base, valleculae and/or piriform sinus, and the patient swallowed again whist being screened, then these subsequent swallows were also analysed and defined as clearing swallows.

Fluoroscopic assessment of aspiration/penetration, data analysis, pharyngeal pressure-flow variables, UES relaxation variables and statistical analysis were conducted according to Example 1.

Results

Twenty nine first swallows were evaluated with the three modalities of fluoroscopy, manometry and impedance. Of these, 15 swallows (in 8 patients) failed to clear the bolus fully and in these patients a further 38 clearing swallows were recorded. Bolus volumes administered to the mouth varied from 1-10 ml (mean 2.2±2 ml). Mostly boluses administered were of 1 ml (19 of 29 first swallows). The potential confounding effects of first swallow volume were investigated by Mann-Whitney Rank Sum Test (of 1 ml vs volumes >1 ml), Kruskal-Wallis ANOVA on ranks and Spearman Rank Order Correlation. No direct comparison of any variable with administered volume achieved statistical significance. Swallow variables for first and clearing swallows were only different for UES-RI (Table 2) and therefore data for first and clearing swallows were grouped for the purposes of comparison between swallows with and without aspiration and bolus residue.

TABLE 2

|  | All First Swallows | All Clearing Swallows (p-value vs FIRST SWs) | Swallows WITHOUT Aspiration | Swallows WITH Aspiration (p-value vs NO Asp) |
|---|---|---|---|---|
| No. Swallows Analysed | 29 | 38 | 51 | 16 |
| PeakP mmHg | 193 [131, 207] | 167 (0.296) [103, 211] | 190 [128, 210] | 106 (0.058) [94, 208] |
| PNadImp mmHg | 28 [18, 59] | 23 (0.224) [14, 34] | 24 [14, 39] | 30 (0.236) [19, 46] |
| Flow Interval msec | 625 [412, 1291] | 783 (0.737) [403, 1332] | 550 [375, 1043] | 1342 (0.003) [644, 1876] |
| TNadImp-PeakP msec | 299 [216, 339] | 287 (0.467) [197, 326] | 299 [211, 332] | 269 (0.542) [207, 337] |
| Swallow Risk Index SRI | 11 [4, 22] | 10 (0.945) [4, 25] | 6 [3, 16] | 22 (0.001) [16, 41] |
| UES Relaxation Interval msec | 429 [313, 607] | 583 (0.022) [394, 825] | 471 [350, 703] | 611 (0.192) [392, 877] |
| UES Intrabolus Pressure mmHg | 21 [15, 28] | 25 (0.466) [12, 34] | 23 [13, 33] | 24 (0.659) [18, 30] |
| Nadir UES Pressure mmHg | 15 [10, 18] | 16 (0.894) [10, 19] | 16 [11, 19] | 14 (0.780) [10, 18] |
| UES resistance mmHg/sec | 55 [30, 72] | 40 (0.296) [31, 58] | 46 [31, 70] | 38 (0.358) [31, 54] |

Summary data of 67 bolus swallows in patients showing the relationships among important objective variables (pharyngeal variables shaded) and the presence of aspiration-penetration. Data presented as median [IQR]. P-values of Mann-Whitney Rank Sum Test for control vs patient and no aspiration vs aspiration shown in parentheses. Data for which p < 0.05 are highlighted in bold text.

Changes in Swallow Variables in Relation to Fluoroscopy Findings

Aspiration-penetration was observed during a total of 16 swallows comprising 8 first and 8 clearing (in 8 patients). The median [IQR] aspiration score was 8 [5, 8] for these aspiration-associated swallows. Patient swallows with aspiration-penetration had a longer flow interval and higher SRI than those without aspiration (Table 2) and, on a swallow by swallow basis, the presence of aspiration-penetration was significantly related to a longer flow interval (OR 4.2 [1.6, 11.1], p<0.001) and higher SRI (OR 23.4 [1.4, 391], p<0.05). A trend for lower peak pressure was also apparent (p=0.058, Table 2).

Figure 10:
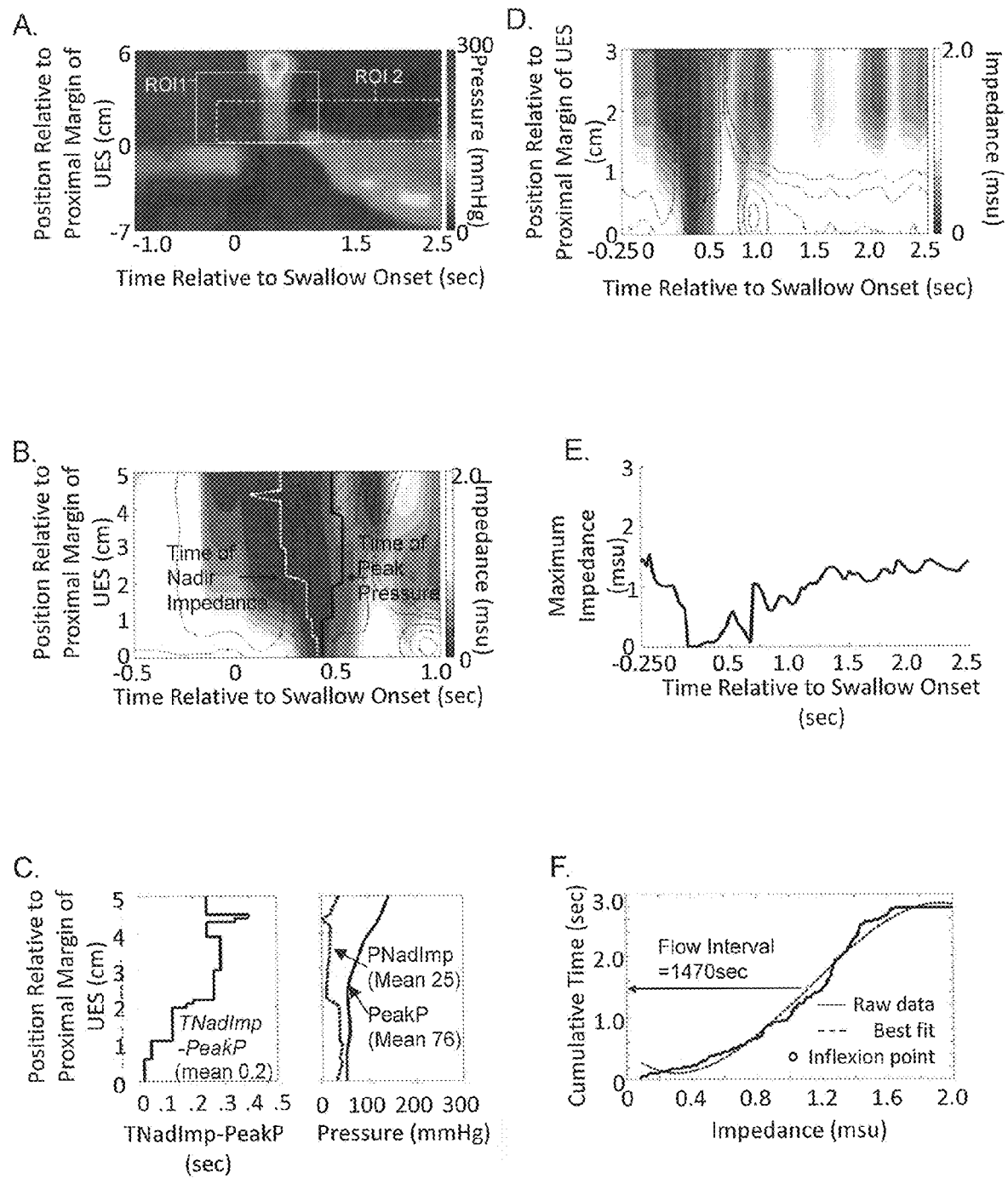
FIG. 10 shows a series of iso-contour plots and graphs of pharyngeal swallow variables in a 9 year old male patient with cerebral palsy. In this patient aspiration-penetration was apparent during liquid swallows (average asp-pen score 3, range 1-8). This example swallow was given an asp-pen score 5 and the SRI was 41 and the average SRI for this patient was 20. (A) A pressure iso-contour plot showing region of interest 1 (ROI 1) used to calculate PNadImp, PeakP and TNadImp-PeakP and ROI 2 used to calculate Flow Interval. (B) Pressure impedance iso-contour plot for ROI 1 showing the timing of pharyngeal nadir impedance and peak pressure. (C) Plots of TNadImp-PeakP, PNadImp and PP with average values shown. (D) Pressure impedance iso-contour plot for ROI 2. (E) A plot of maximum impedance over time. (F) Impedance cumulative time plot showing raw data, the third-order polynomial best fit and the inflexion point of the best fit curve was used to define the Flow Interval.

Both longer flow interval and higher SRI correlated with higher aspiration scores (Spearman Rank Order Correlations of r=0.336, p=0.006 and r=0.381, p=0.002 respectively). All other swallow variables were not significantly different in relation to the presence/absence of aspiration (Table 2). Example tracings and calculations from a patient with deglutitive aspiration are provided in FIG. 10 (A-F).

Patient swallows with bolus residue compared to those without residue had lower peak pressure (100 [88, 113] vs 194 [164, 212] mmHg, p<0.001), a longer flow interval (1290 [580, 2300] vs 1177 [704, 1668] msec, p=0.006) respectively, p=0.008), a longer UES-RI (625 [534, 921] vs 450 [313, 0.611] msec, p=0.007) and higher UES-IBP 30 [24, 37] vs 20 [11, 27] mmHg, p=0.001). Other swallow variables were not significantly different in relation to the presence/absence of residue. The presence of bolus residue following clearance failure was not related to aspiration score (odds ratio 1.1 [0.9, 1.3], p=0.339).

Predictive Value of Swallow Risk Index for Detecting Aspiration

We assessed whether the average SRI recorded in an individual patient could predict the presence/absence of aspiration during fluoroscopy of the same patient. The average SRI correlated strongly with the average aspiration score (Spearman Rank Order Correlation of 0.753, p=0.006). Based on kappa values, an average SRI of 15 was the optimal threshold for accurate prediction of aspiration in the patient cohort (kappa 0.82) (FIG. 11A) and was also optimal in terms of sensitivity (1.0) and specificity (0.83) (FIG. 11B).

Discussion

The present study has again established that combined manometry and impedance measurements can detect alterations in pressure-flow characteristics of pharyngeal swallow that predispose to aspiration risk, this time in paediatric patients with suspected aspiration and high dysphagia.

Whilst it has been widely demonstrated that volume swallowed can influence individual functional parameters, in the current study these volume effects appeared small and there was no significant volume effect on the SRI. This further demonstrates the added value of combining variables to derive the SRI. This is particularly encouraging of utility in paediatric patients, in Mom the volume administered during swallow testing is very difficult to control and, even if a standardised volume is administered to the mouth, it may nevertheless take several swallows to consume. The fact that the predictive value of the SRI appears to be robust in the face of the potential confounding factors such as age and control of bolus volume is supportive of this new methodology having very real clinical potential as a screening tool for aspiration risk in the paediatric population.

Example 3

Assessment of Pharyngeal Motor Function Relevant to Post-Swallow Bolus Residue

The aim of this study was to apply the approach developed in Example 1, i.e. the use of high resolution intraluminal manometry combined with impedance measurement, for the objective assessment of pharyngeal function relevant to post-swallow bolus residue. This approach was evaluated to determine if it enables recognition of subjects with swallowing dysfunction causing bolus residue, without performance of fluoroscopy.

Methods

Subjects 23 dysphagic patients (17 adults, 6 children, 14 males, mean age 55 years, age range 2-95 years) were referred to the paediatric and adult swallowing clinics for a videomanometry study of the pharynx and esophagus. Underlying diseases/conditions were identified through a review of medical records. Sixteen patients had a neurological history comprising 7 adults with stroke, 4 children with cerebral palsy, 2 adults with Parkinson's disease, 2 adults with dementia and 1 adult post neurosurgery. Of the remainder of patients, 1 adult was post cervical surgery, 1 child had cardiovascular disease, 2 adults had a motility disorder and 2 adults and 1 child had unknown aetiologies at the time of study. For comparison, ten healthy adult subjects were recruited who had no swallowing difficulties, nor other symptoms suggestive of a motility disorder (5 male, mean 36.6 years, range 24-47 years). The study protocol was approved by the Research Ethics Committee, University Hospitals Leuven, Belgium.

Measurement Technique

All fluoroscopy studies were performed in the Radiology Department, University Hospitals Leuven. Studies were performed using a 3.2 mm diameter solid state manometric and impedance catheter incorporating twenty five 1 cm-spaced pressure sensors and twelve 2 cm long impedance segments (Unisensor USA Inc). Subjects were intubated (topical anaesthesia—Lignocane) and the catheter was positioned with sensors straddling the entire pharyngo-esophageal segment (velo-pharynx to proximal esophagus). Pressure and impedance data were acquired (upright position) at 20 Hz (Solar GI acquisition system, MMS, The Netherlands). Semi-solid test boluses were administered orally via syringe. All bolus stock contained 1% NaCl to enhance conductivity. As per routine clinical fluoroscopy, test boluses to patients were of 1-15 ml semi-solid. For controls, 2×10 ml semi-solid boluses were administered, both being recorded during fluoroscopy. Video-loops of the fluoroscopy images of swallows were simultaneously acquired (25 frames/sec). The first swallow that followed bolus administration to the mouth was defined as the first swallow. If the first swallow failed to clear the bolus from the oral cavity, tongue-base, valleculae and/or piriform sinus, and the subject/control was asked to swallow again whist being screened, these subsequent swallows were also analysed and defined as clearing swallows.

Fluoroscopic Assessment of Bolus Residue and Aspiration-Penetration Fluoroscopic images from patient and control studies were scored for residue and the occurrence of aspiration-penetration blind to the impedance findings. Swallows were also assessed for the presence or absence of post-swallow residue in the valleculae, piriform sinus and/or posterior pharyngeal wall and also scored from 1-6 according to the number of structures showing evidence of residue: No residue in any of these structures was assigned a score of 1. If residue was present, then additional scores were weighted towards the anatomical regions in which residue posed an aspiration risk (+1 for valleculae, +2 for piriform sinus and +2 for posterior pharyngeal wall). Hence valleculae only=2, posterior pharyngeal wall or piriform sinus only=3, valleculae and posterior pharyngeal wall or piriform sinus=4, posterior pharyngeal wall and piriform sinus=5; all structures=6. Swallows were assessed for the presence of aspiration-penetration using a validated 8-point score (Rosenbek J C, supra), influenced primarily by the depth to which material passes in the airway and by whether or not material entering the airway is expelled during the swallow sequence (Score 1=no aspiration, 2-5=penetration, 6-8=aspiration).

Data analysis, pharyngeal pressure-flow variables, UES relaxation variables and statistical analysis were conducted according to Example 1. However, in this study, we evaluated the SRI in relation to bolus residue.

Results

Seventy six swallows were recorded in patients with the three modalities of manometry, impedance and fluoroscopy. Swallows comprised 37 first swallows, of which 24 failed to clear, and a further 39 clearing swallows. Thirty nine swallows were recorded in controls with all modalities comprising 18 first swallows and a further 21 clearing swallows.

Patient vs Control Swallows

There was little scope to standardise bolus volume administered to patients, nevertheless there were no significant differences amongst first swallow variables recorded following administration of different bolus volumes. Comparisons amongst the different swallow variables calculated for semi-solid boluses in patients and controls are shown in Tables 3 and 4.

Figure 27:
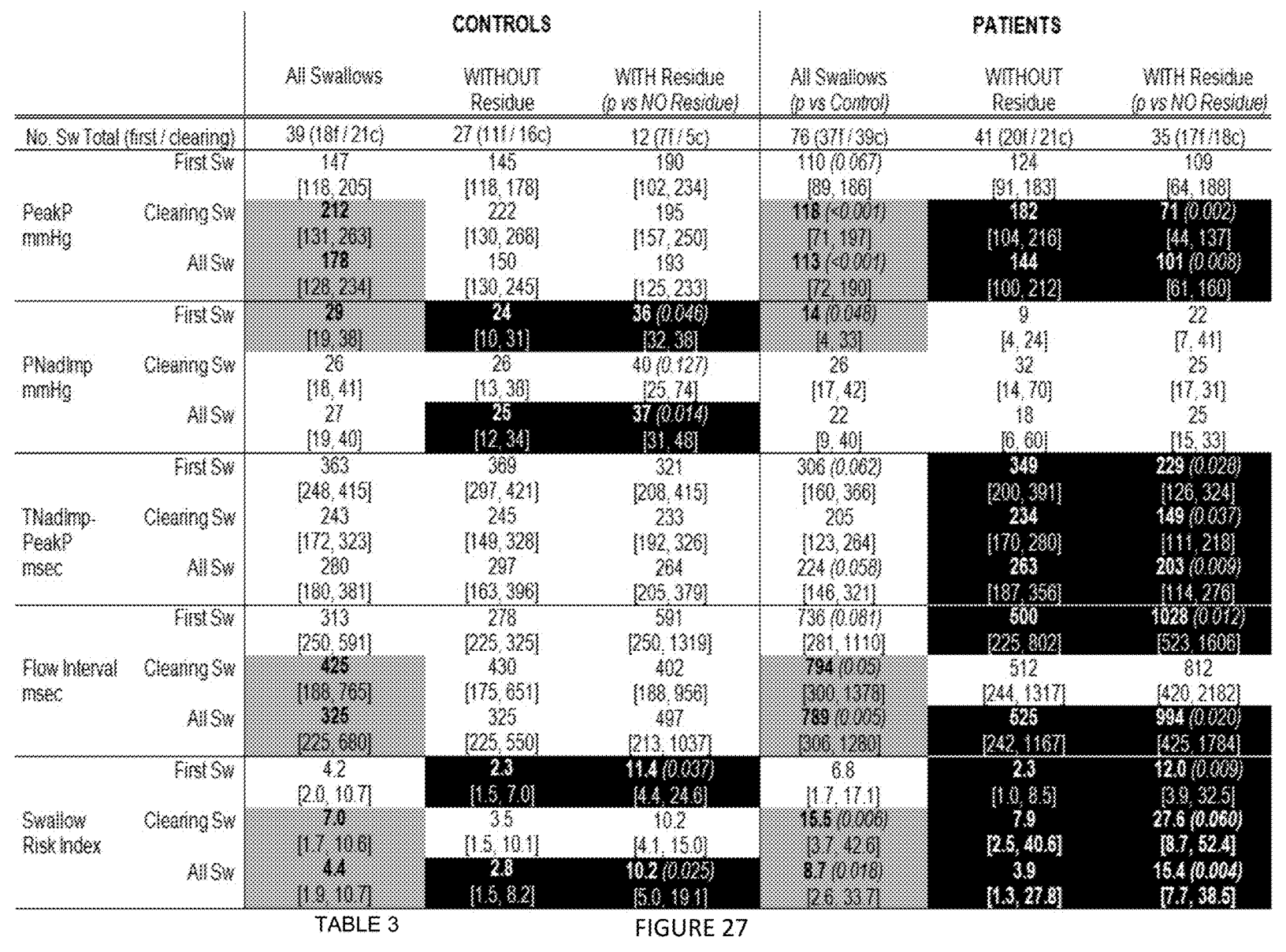

Table 3, as found in FIG. 27, provides summary data of 115 swallows in controls and patients showing the relationships among important objective pharyngeal variables and the presence of post-swallow residue. Data is presented as median [IQR]. Mann-Whitney Rank Sum Test P-values <0.1 for control vs patient and residue vs no residue are shown in parentheses. Data for which p<0.05 are shaded grey for control vs patient and shaded black for no-residue vs residue.

Table 4, as found in FIG. 28, provides summary data of 115 swallows in controls and patients showing the relationships among important objective UES variables and the presence of post-swallow residue. Data presented as median [IQR]. Mann-Whitney Rank Sum Test P-values <0.1 for control vs patient and residue vs no residue are shown in parentheses. Data for which p<0.05 are shaded grey for control vs patient and shaded black for no-residue vs residue.

For pharyngeal variables (Table 3) patient swallows, compared to control, had lower PeakP, lower PNadImp, shorter TNadImp-PeakP (trend p=0.053), longer Flow Interval and a higher SRI. For UES variables (Table 4) patient swallows, compared to control, had a longer UES-RI, lower UES-IBP and lower UES resistance. The swallow risk index was elevated in patients compared to controls (Table 3).

In patients, 46% of swallows had residue compared to 31% of control swallows. Qualitatively, the amount of residue was also less in controls, however, as the scoring system employed only assessed residue based on its presence and the number of structures involved, this difference was not apparent within the quantitative score (median residue score of 3 [2, 5] vs 3 [2, 4] for swallows with residue in patients and controls respectively).

Several variables were different in relation to the presence of post-swallow residue and there were clear differences between patients and controls in terms of the specific variables altered. PeakP, for example, was significantly lower during patient swallows with residue compared to those without residue; however PeakP did not differ in this way in controls (Table 3). Patient swallows with residue had significantly shorter TNadImp-PeakP, longer Flow Interval, longer UES-RI and lower UES resistance; none of these variables were significantly different in control swallows with residue (Tables 3 and 4). Conversely, control swallows with residue had an elevated PNadImp, which was not the case with patient swallows with residue (Table 3). Finally, control swallows with residue had a significantly higher Nadir UESP and UES resistance Mile patient swallows with residue conversely had a significantly lower Nadir UESP and UES resistance (Table 4). In contrast to all individual variables, the swallow risk index was significantly higher in relation to residue for swallows in both patients and controls (Table 3).

Figure 12:
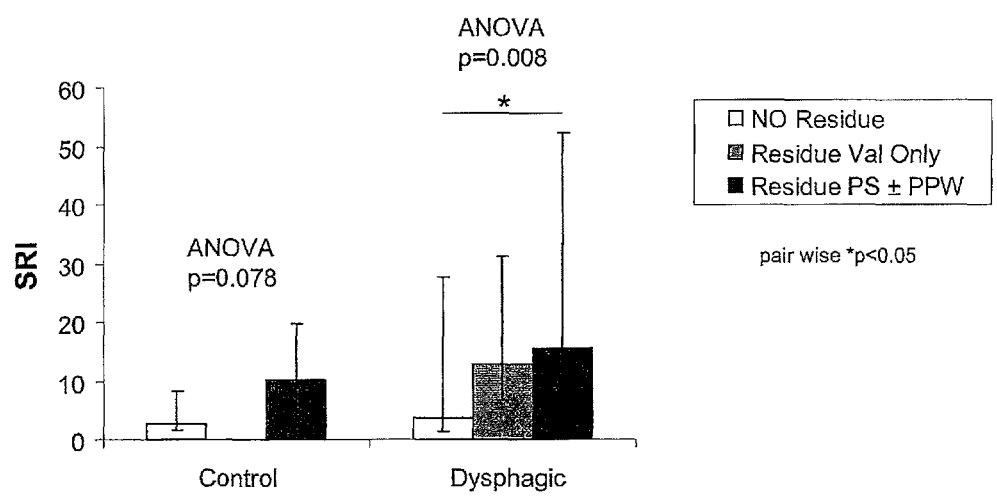
FIG. 12 is a graph showing swallow risk index (SRI) calculations for subjects and controls used in the study described in Example 3. The SRI for all swallows was recorded in control subjects and dysphagic patients grouped according to the severity of residue based on anatomical location in the valleculae only (Val) or piriform sinus (PS) and/or posterior pharyngeal wall (PPW). Data presented as median [IQR], p=values shown for Kruskal-Wallis One Way Analysis of Variance on Ranks of SRI. *$p<0.05$ for no residue vs PS±PPW using Pairwise Multiple Comparison Procedures (Dunn's Method).

Variables were similarly altered in relation to bolus residue score. In patients, higher bolus residue score correlated with lower PeakP (r=−0.285, p=0.013), shorter TNadImp-PeakP (r=−0.313, p=0.006), longer Flow Interval (r=0.242, p=0.035) and longer UES-RI (r=0.428, p=0.0001), Mile similar relationships were not observed in controls. In controls, higher bolus residue score correlated with higher PNadImp (r=0.381, p=0.017), higher UES-IBP (r=0.328, p=0.042) and higher Nadir UESP (r=0.351, p=0.028), Mile similar relationships were not observed in patients. Residue score correlated with lower UES resistance (r=−0.324, p=0.004) in patients but inversely higher UES resistance (r=0.341, p=0.034) in controls. A higher residue score correlated with higher SRI in both patients (r=0.329, p=0.004) and controls (r=0.333, p=0.0387). FIG. 12 shows the relationship between the extent of residue and the median SRI in patients and controls.

Figure 13:
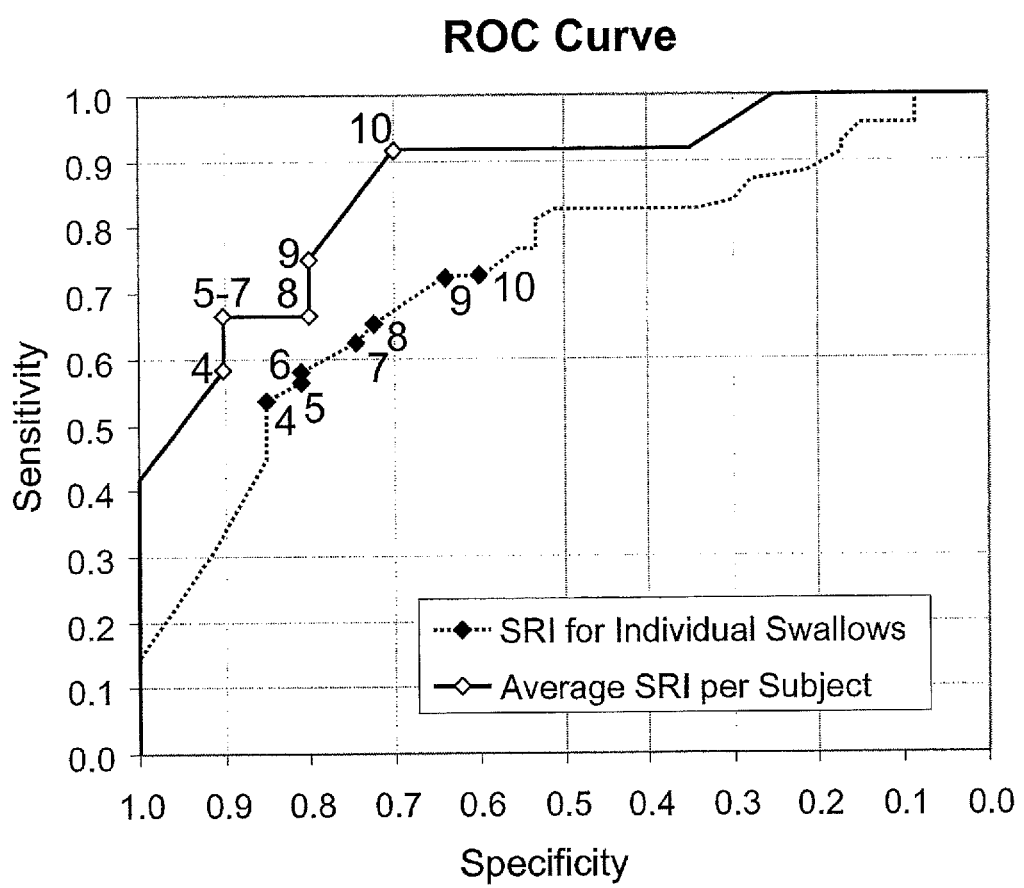
FIG. 13 is a receiver operator curve summarising the predictive value of the swallow risk index (SRI) for determining the presence or absence of bolus residue. Receiver operator curves are based on SRI calculated for individual swallows as well as the average SRI determined for each individual. Numbers indicate data points corresponding to SRI values of 4-10.

As the SRI was the only variable significantly elevated in relation to residue in both patients and controls, we assessed the predictive value of SRI for detecting residue. Receiver operator curves showing the sensitivity and specificity of SRI are shown in FIG. 13, this shows that the predictive value of the SRI for detection of residue can be improved by averaging the findings over several swallows. An average SRI cut-off of 9 appears to be optimal for detecting residue with an overall sensitivity of 75% and specificity of 80% (81%/71% in patients only and 80%/75% in controls only).

Patient Swallows with Aspiration-Penetration Six aspiration-penetration episodes were recorded on fluoroscopy in 4 patients (3 penetration/3 aspiration; average aspiration-penetration score 4.8, range 2-8; average residue score 5.2, range 2-6). Of these, two episodes occurred during first swallows and four during clearing swallows. Despite low numbers of analysable events, swallows with aspiration compared to those without, had a lower PeakP (55 [30, 100] vs 120 [81, 193] mmHg respectively, p=0.005) and a longer UES-RI (1179 [857, 1474] vs 644 [741, 1029] msec, p=0.018) and there was also a clear statistical trend in favour of a shorter TNadImp-PeakP (160 [−11, 246] vs 227 [149, 333] msec, p=0.073) and a higher SRI (22.3 [13.1, 61.8] vs 8.3 [2.5, 33.4], p=0.075).

Discussion

A novel automated approach to the analysis of pharyngeal manometry and impedance recordings was used to characterise pharyngeal function in relation to ineffective deglutition leading to bolus residue. While, bolus residue was evident on both patients with dysphagia as well as asymptomatic controls, the specific functional variables related to the presence of residue differed between patients and controls. In contrast, a swallow risk index, which was based upon the objective calculation of four pharyngeal pressure-flow variables, was elevated in relation to residue in both patients and controls.

Our prior studies have concentrated on optimising criteria for the direct detection of bolus residue using intraluminal impedance. However, we discovered large differences in the optimal criteria determined for controls and patients as well a large inter-patient differences related to pathology. Our new approach combines pressure and impedance measurement to derive a range of new swallow function variables which can be combined in a manner that predicts whether swallows are likely to be ineffective based on the SRI. This contrasts with the standard approach which evaluates impedance and pressure findings separately. As we clearly show, pharyngeal/UES motor function does not always empty the pharynx in healthy controls, and our new approach is therefore markedly superior, having high predictive value in both controls as well as patients.

Many swallows in both patients and controls were observed to be ineffective and failed to completely clear the bolus. We were surprised to discover that residue was scored similarly for patients and controls, even though, qualitatively, controls exhibited only trace amounts of residue coating structures, whilst in patients residue tended to be of greater volume. The fact that the impedance-based Flow Interval, was significantly longer in relation to residue, in patients only and not controls, provides some evidence for the volume of residue being larger in patients. This aspect of bolus quantity was not assessed in the derivation of the residue score because it was considered too subjective. This highlights one of the major limitations of fluoroscopy-based scoring systems. The aspiration-penetration score for example, has been found to have a high degree of inter/intra-rater reliability, however even this widely utilised system is limited by the fact that it does not distinguish volume aspirated and therefore trace vs large volume aspiration below the vocal cords is scored equally.

Although residue scores were similar the functional variables found to be altered in relation to residue were very different in controls vs patients. In controls, residue was mostly related to variables suggestive of increased UES resistance due to impaired UES relaxation, i.e. increased PNadImp (suggestive of increased pharyngeal intrabolus pressure), increased UES-IBP, increased Nadir UESP and increased UES resistance. In contrast, residue in patients was mostly related to poor bolus propulsion and pharyngeal/UES weakness, i.e. short TNadImp-PeakP, low pharyngeal PeakP, prolonged UES-RI, low nadir UESP and low UES resistance. These findings in our patients are perhaps not surprising given that the majority had a neurological basis for their dysphagia.

Despite these large differences in controls compared to patients with respect to the specific functional variables governing pharyngeal effectiveness, the swallow risk index was nevertheless elevated in relation to residue and was highly predictive of residue for both controls and patients. This clearly demonstrates the inherent value of taking into account several different measures of function, which in turn delivers a more accurate global assessment of pharyngeal effectiveness. In practise, having utilised a global measure such as the SRI to establish pharyngeal effectiveness, one could then turn to individual functional variables to identify pathophysiological causes. This potentially allows for a relatively specific diagnosis of varying mechanical dysfunctions. From such analysis, it may be possible to devise well targeted therapeutic interventions and, in turn, track the effectiveness of such interventions.

The fact that the predictive value of the SRI, in relation to residue, appeared to be similar for patients and controls and robust in the face of the potential confounding factors, such as age, engenders confidence that this methodology has very real potential for clinical implementation.

Example 4

Identification of Pressure-Flow Variables as Markers of Susceptibility for Development of Post-Operative Dysphagia The aim of this experiment was to determine if the methods of the present invention could be used for an objective assessment of esophageal function in order to predict post-operative dysphagia following Nissan Fundoplication surgery.

Esophageal dysphagia, the failure of food boluses to clear from the esophageal lumen, is a post-operative complication of antireflux surgery for gastroesophageal reflux disease (GERD). The genesis of this problem lies in fact that anti-reflux operation (e.g. Nissan Fundoplication) causes a restriction at the esophago-gastric junction, which, whilst beneficial for reducing gastroesophageal reflux from the stomach into the esophagus, may also interrupt normal antegrade flow from the esophageal lumen into the stomach during swallowing. Whist dysphagia is a common symptom of GERD which often resolves following surgery, approximately 1 in 3 patients develop dysphagia as a consequence of surgery. It would be very useful to determine which patients are susceptible to developing post-operative complications of dysphagia; however, there are no tests presently that can be performed pre-operatively which will predict the likelihood of dysphagia due to surgery.

There have been several studies that have evaluated intraluminal manometry of the esophagus and esophagogastric junction to determine if pressure variables (lower esophageal sphincter pressure and peristaltic pressures) can predict post-operative dysphagia. These studies have not been able to identify a measurable parameter predictive of dysphagia. Intraluminal impedance has also been used to define bolus transit and clearance in patients and this method similarly fails to predict post-operative dysphagia.

This important clinical question has been addressed using the novel analysis method of the present invention which combines pressure and impedance measurements to produce novel esophageal pressure-flow variables guided predominately by the timing of the impedance nadir recorded during bolus flow. The aim of this study was to determine if one or more of these variables was a marker of susceptibility for development of post-operative dysphagia.

Methods

Figure 14:
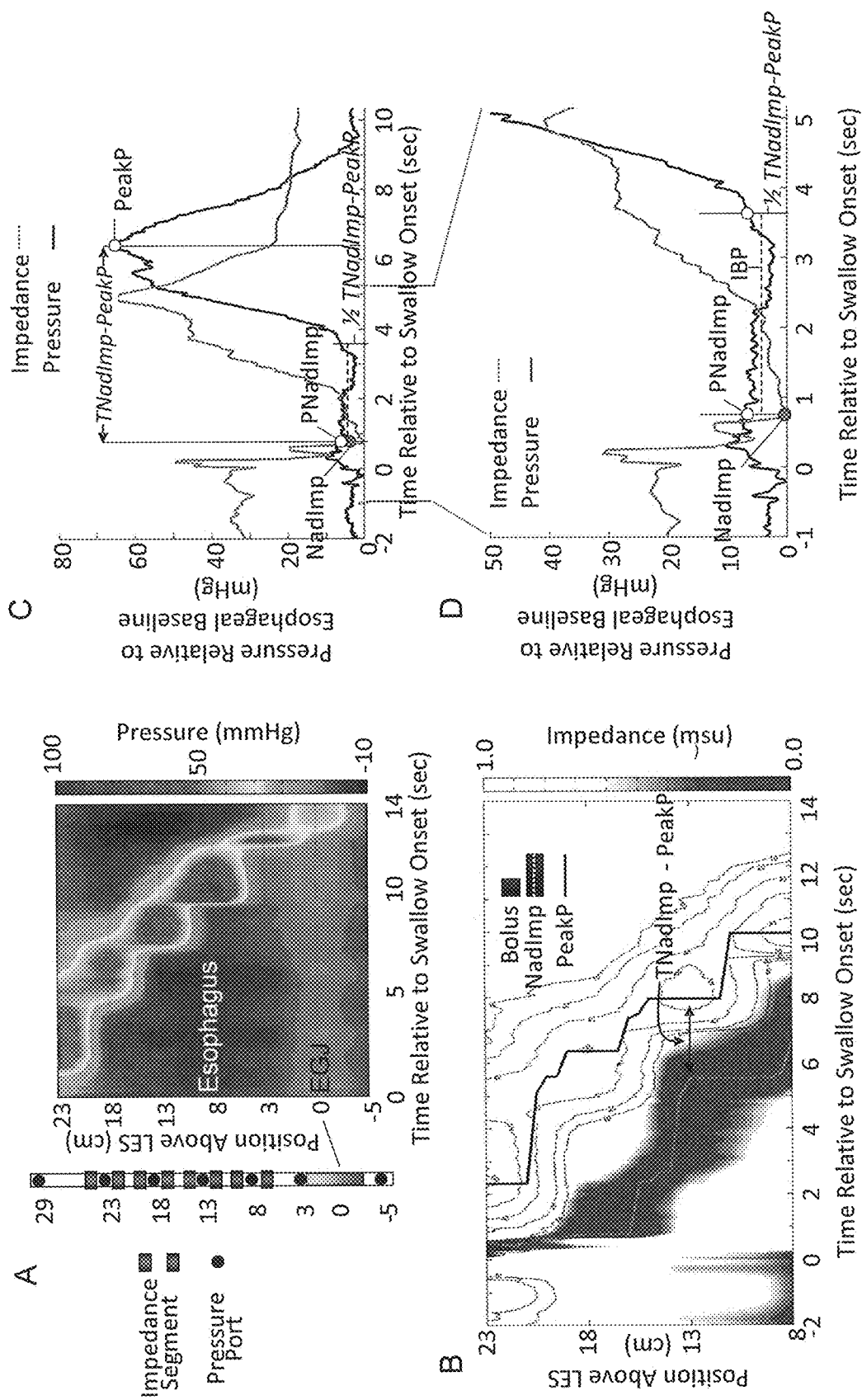
FIG. 14 is a summary of the analysis methods used in the study described in Example 4. (A) A schematic of the catheter used showing the location of pressure ports and impedance electrodes. An example pressure isocontour plot of esophageal and EGJ pressures are also shown. (B) A combined pressure-impedance plot showing simultaneous recordings from pressure and impedance channels. Pressures shown as iso-contour lines, grey shading shows regions of low impedance indicative of the presence of bolus. The timings of NadImp and PeakP are marked at all positions down the plot. (C) A line plot of pressure and impedance recorded at 18 cm proximal to the EGJ. This illustrates how variables PNadImp, TNadImp-PeakP and Peak P are determined at all positions down the plot. (D) An expanded plot of C, illustrating how the IBP was determined at all positions down the plot.

Manometry and impedance recordings from 18 adult GERD patients (8 female/10 male, aged from 31-70 years) who received Nissan Fundoplication surgery were analysed. All patients underwent esophageal manometry using a 9 channel perfusion manometry catheter incorporating 4 impedance segments 5 cm apart. The configuration of the catheter is shown in FIG. 14A. Studies were performed both before and after surgery in the Department of Surgery, University of Adelaide. Subjects were intubated and the catheter was positioned to record esophageal and esophagogastric junction pressures. Ten×10 ml viscous boluses were administered orally via syringe and the resulting motility recorded.

Assessment of Dysphagia Symptoms

Evidence of symptoms of dysphagia was obtained at the time of study. The dysphagia score of Dakkak and Bennett, 1992, *J. Clin. Gastroenterol.* 14: 99-100 was used. This assesses dyphagia severity based on ability to swallow nine items of food. A score of 1 or more out of 45 is indicative of the presence of Dysphagia symptoms.

Data Analysis

Raw manometric and impedance data for each bolus swallow were visualised over 30 second windows and exported from the recording system in ASCII text format and then analysed by a separate computer using MATLAB (version 7.9.0.529; The MathWorks Inc). Pressure and impedance data were smoothed by a cubic interpolation method which doubled the temporal data and increased the amount of spatial data by a factor of 10, hence achieving a virtual increase from 1 value per 5 cm sampled at 30 Hz to 10 values per cm sampled at 60 Hz. The raw impedance data were standardised to the median impedance (presented therefore as median standardised units (msu) rather than ohms).

Derivation of Esophageal Pressure-Flow Variables

The spatial region of the esophageal pressure wave recorded across the 4 pressure sensor and impedance segment array was analysed in a separate pressure-impedance plot (FIG. 14B). The timings of the esophageal impedance nadir (NadImp) and Peak Pressure (PeakP) and the time interval from NadImp to Peak Pressure (TNadImp-PeakP) were automatically determined at all positions along the plot (FIG. 14B).

Having identified NadImp and PeakP at all positions, the rate of progression of NadImp (NadImp rate) and Peak Pressure (PeakP rate) were calculated. Guided by the timing of NadImp, the following variables were also determined at each position and averaged for both the entire pressure-impedance array and for the distal half only of the pressure-impedance array:

The pressure at the time of NadImp (PNadImp) (FIG. 14C).

Pressure of PeakP (FIG. 14C).

The median intrabolus Pressure (mIBP); estimated by calculating the median pressure recorded from NadImp to the mid time point of TNadImp-PeakP (FIG. 14D).

The IBP slope, defined by the change in pressure over time from PNadImp to the pressure at the mid time point of TNadImp-PeakP.

All esophageal pressures during swallowing were reference to baseline pre-swallow esophageal pressures.

Derivation of Esophago-Gastric Junction Relaxation Pressures

Esophago-gastric junction (EGJ) relaxation characteristics were measured using the established method of Kahrilas P J et al., 2008, *J. Clin. Gastroenterol.* 42: 627-635. The cumulative duration of EGJ relaxation was plotted from the minimum to the maximum pressure recorded in the EGJ. This plot was used to calculate 4 second integrated relaxation pressure. Resting EGJ pressure was recorded for 10 seconds prior to EGJ relaxation onset. All EGJ pressures were referenced to average gastric pressure.

Statistics

Non-parametric grouped data were presented as medians [inter-quartile range] and compared using the Mann-Whitney Rank Sum Test. Parametric grouped data were presented as means±SEM and compared using a t-test. Paired data pre/post surgery were compared using Wilcoxon Signed Rank Test or paired t-Test. For multiple comparisons Kruskal-Wallis One Way Analysis of Variance on Ranks or One Way Analysis of Variance was used and pair-wise comparisons were made using multiple comparison procedures (Dunn's Method or Holm-Sidak method). For all tests a $p<0.05$ indicated statistical significance.

The sensitivities and specificities were determined for candidate predictive variables. The optimal level of concordance between baseline criteria and the presence of post-operative dysphagia was expressed with Cohen's kappa Statistic. The scale for kappa values is: 0.00=no agreement, 0.00-0.2=slight, 0.21-0.40=fair 0.41-0.60=moderate, 0.61-0.8=substantial, 0.81-1.00=almost perfect.

Results

Eight patients reported dysphagia symptoms before surgery, compared to fourteen after surgery. In no patients with pre-operative dysphagia, did the symptoms completely resolve post-operatively. However, six patients without dysphagia symptoms developed "new" dysphagia post-operatively. Only four patients reported no dysphagia symptoms both pre and post surgery.

The Dakkak dysphagia score was not significantly different following surgery (average score 6±2 pre vs 9±2 post, p=0.327). Pre-surgical dysphagia scores were significantly higher in patients with a hiatus hernia (HH) compared to no HH (median score 10 [0-21] vs 0 [0, 3], p=0.032). Increased hernia size was also related to higher pre-operative dysphagia scores (Spearman Rank Order Correlation r=0.562, p=0.015). Baseline esophageal and EGJ variables were however not significantly different in relation to HH.

Table 5, as provided in FIG. 29, provides pressure flow variables for viscous swallows pre and post surgery and in relation to the presence of dysphagia pre a nd/or post surgery. Paired data from all patients before and after surgery compared using Wilcoxon Signed Rank Test or paired t-test. Data for patients with and without dysphagia compared using Mann-Whitney Rank Sum Test or t-test. P-values ≤0.10 shown in parenthesis. Significant comparisons highlighted as black cells.

Seven patients received a partial wrap Nissen and 11 a full wrap Nissen. Post-surgical dysphagia scores were not significantly different in relation to operation type (median score 6 [0-21] partial vs 4 [0-12] full Nissen, p=0.466). Post-operative esophageal and EGJ variables were not significantly different in relation to operation type. Table 5 shows results for all measured pressure-flow variables for all patients before and after surgery. Esophageal variables were not significantly altered by surgery, whilst EGJ variables were all significantly altered consistent with fundoplication increasing pressures at the level of the EGJ (Table 5).

Table 5 also shows results for variables grouped based on the time of measurement (before/after surgery) and the presence of dysphagia symptoms before or after surgery. Across pre-surgical studies, patients with dysphagia symptoms pre-surgery had lower Peak Pressures than those without symptoms (29 vs 45 mmHg, p<0.05).

No other variable was significantly altered in relation to dysphagia pre-surgery. Across post-surgical studies, no variable was significantly altered in relation to dysphagia post-surgery (Table 5). When variables recorded pre-surgery were compared for patients with and without dysphagia symptoms post-surgery several variables were significantly different (Table 5). At baseline study, patients who developed dysphagia symptoms post-surgery had elevated esophageal IBP (also referred to as distal IBP)(19 vs 10 mmHg, p<0.05), elevated esophageal IBP slope (also referred to as distal IBP Slope)(9 vs 2 mmHg/sec, p<0.05) and shorter esophageal TNadImp-PeakP (also referred to as distal TNadImp-PeakP)(2.5 vs 4.0 sec, p<0.05). Based on these findings a dysphagia risk index (DRI) was defined by the formula:

$$DRI=IBP \times IBP\ Slope \times TNadImp-PeakP^{-1}$$

At baseline study, patients who developed dysphagia symptoms post-surgery had an elevated DRI (43 vs 9, p<0.05). Table 6 compares patients with no dyphagia symptoms with those who had symptoms pre and post surgery and those that had symptoms after surgery only. Preoperative measurements of esophageal TNadImp-PeakP and DRI were significantly different among the three groups using ANOVA. Pairwise comparisons of esophageal TNadImp-PeakP and DRI were also significantly different between patients with no dyphagia symptoms and those with symptoms after surgery only (Table 6). In contrast, post-operative measurements of these variables were not significantly different between the three groups of patients (Table 6).

Table 6, as provided by FIG. 30, provides pressure flow variables and the dyphagia risk index for viscous swallows before and after surgery grouped by patients with no dysphagia, dysphagia pre and post surgery and dysphagia post-surgery only. P-values are for Kruskal-Wallis One Way Analysis of Variance on Ranks or One Way Analysis of Variance. *pairwise p<0.05 vs No Dysphagia using Multiple Comparison Procedures (Dunn's Method or Holm-Sidak method). Significant comparisons highlighted as black cells.

Figure 15:
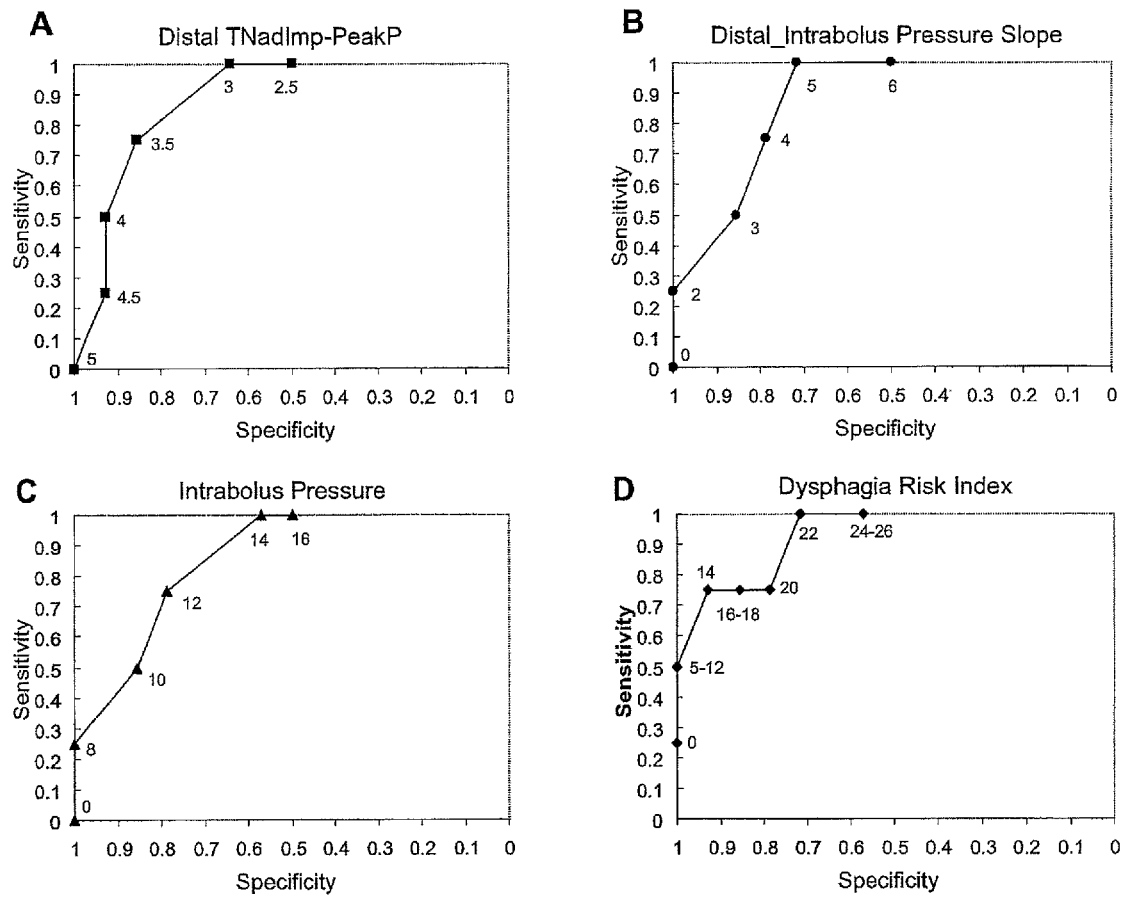
FIG. 15 shows ROC curves for data obtained from the study described in Example 4 showing the baseline esophageal pressure-flow variables found to be significantly related to post-operative dysphagia.

The predictive value of baseline esophageal TNadImp-PeakP, esophageal IBP Slope, IBP and Dyphagia Risk Index for determining post-operative dysphagia symptoms was assessed. Optimal predictive criteria were an esophageal TNadImp-PeakP of <3.5 sec (sens 0.75, spec 0.86, Kappa 0.557), esophageal IBP Slope >5 (sens 0.71, spec 1.0, Kappa 0.526) and IBP>12 (sens 0.75, spec 0.79, Kappa 0.454). Optimal criteria for the Dysphagia Risk Index was >14 (sens 0.75, spec 0.93, Kappa 0.679=substantial agreement). Receiver operator curves for the three most predictive variables and DRI are shown in FIG. 15.

Example 5

Identification of Pressure-Flow Variables as Markers of Obstruction Along the Pharyngo-Esophageal Segment The aim of this experiment was to determine if pressure-flow variables identified by the methods of the present invention could be used to identify the position of an obstruction in the pharynx and/or esophagus of a subject, wherein the obstruction arises as a result of surgery or therapy.

Obstruction of the UES or esophageal body is a common cause of dysphagia. UES obstruction can occur following radio-therapy for head and neck cancer, following cervical surgery, in relation to neurological diseases such a cerebral palsy and in relation to anatomical abnormalities (bars/strictures). Esophageal body obstruction can occur in relation to formation of strictures/webs which occlude the lumen.

Regardless of the cause, the ability to identify the precise location of an obstruction may help guide interventions for obstruction (e.g. dilatation). In the pharynx, radiological imaging sometimes is unable to distinguish failure of UES opening due to obstruction vs failed UES opening to poor bolus propulsion.

The novel pressure and impedance methods described herein can be applied along the length of the lumen in order identify the precise location of abnormality/inefficiency. By way of example we present two cases of patients with obstruction and how pressure-flow variables, such as the value of NadImp and the TNadImp-PeakP, are altered in the region of the obstruction allowing the position of the obstruction to be identified without the need for radiology.

Subject 1

Figure 16:
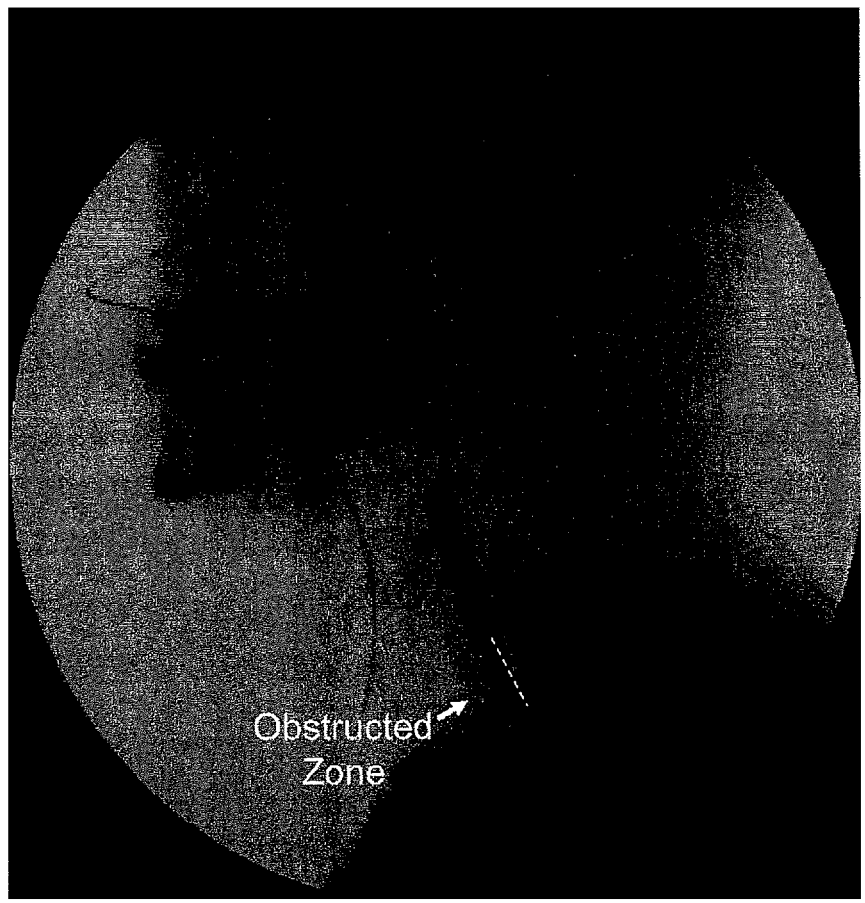
FIG. 16 is a radiological image of subject 1 used in the study described in Example 5. The image was taken during swallowing and identifies a region of narrowing which is adjacent to the metal supports that have been implanted in the cervical spine of the subject.
Figure 17:
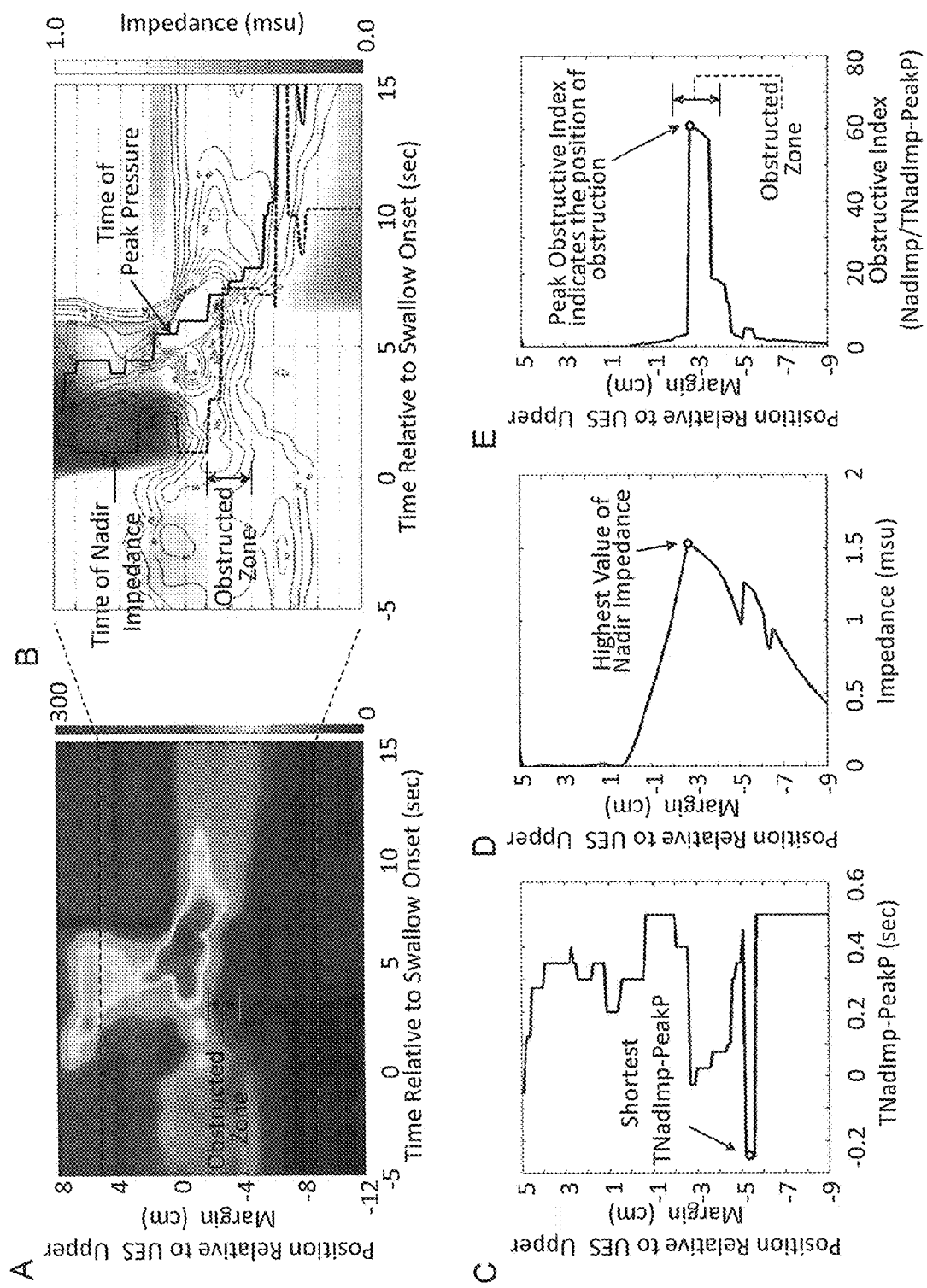
FIG. 17 shows a series of plots and graphs summarising how the impedance and pressure measurements taken from subject 1 of Example 5 were analysed to identify an obstructed zone. (A) A pressure iso-contour plot of a 10 ml bolus swallow in subject 1 with the spatial region of the obstruction identified on the plot zone (between position −2 to −4 cm relative to proximal margin of UES). (B) A pressure impedance plot showing the spatio-temporal location of NadImp and Peak P. (C) A plot of TNadImp-PeakP, noting that TNadImp-PeakP is shortest between positions −2 and −6 cm (relative to UES proximal margin). (D) A plot of NadImp, noting that the level of NadImp is highest at position −2 cm (relative to UES proximal margin). (E) A plot of the "obstructive index" (NadImp/TNadImp-PeakP) which is highest precisely within the obstructed zone.

A 58 year old man who developed symptoms post anterior cervical fusion (C5-C6) surgery in whom fluoroscopy demonstrated high obstruction. FIG. 16 shows a radiological image of subject 1 taken during swallowing that identifies a region of narrowing which is adjacent to the metal supports that have been implanted in the cervical spine of the subject. FIG. 17 shows the analysis of pressure and impedance measurements taken from the subject during swallowing.

Subject 2

Figure 18:
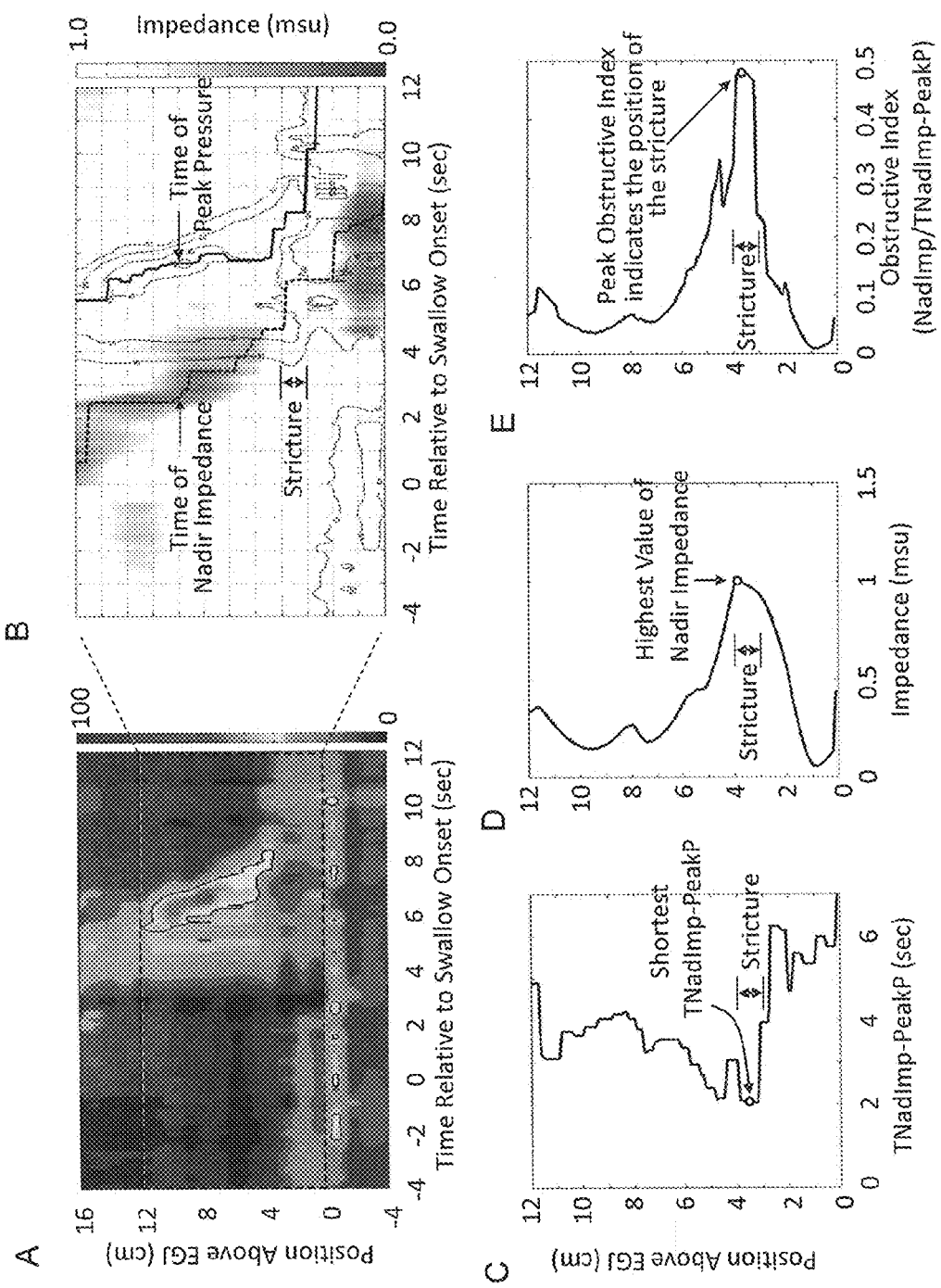
FIG. 18 shows a series of plots and graphs summarising how the impedance and pressure measurements taken from subject 2 of Example 5 were analysed to identify an obstructed zone.

A 13 year old Girl with GERD who received a Nissen Fundoplication operation as a toddler and who has ongoing symptoms of esophageal dysphagia refractory to dilatation of the esophago-gastric junction. Manometry revealed a peristaltic dysfunction with impaired deglutitive EGJ relaxation. When the recorded swallows in this patient are analysed in a similar fashion to subject 1 (see FIG. 18), a region of obstruction 3-4 cm proximal to the EGJ is identified. Radiologically this region appears as a small esophageal stricture which, whilst observed, was not considered problematic by the attending physician. In contrast the recording identifies this region as being important and therefore a target for intervention in order to achieve symptomatic relief.

Discussion

The studies performed in subjects 1 and 2 establish the value of measurement of pressure-flow variables along the length of the pharyngo-esophageal segment to identify the precise location of abnormality. We demonstrate two variables which we believe have utility for detecting obstruction; however, it is likely that other pressure-flow variables (as described in previous sections of this specification) may also have utility in this regard. This study also establishes the value of combining different pressure-flow variables to return a more precise indication of the location of the abnormality. Again it is likely that other pressure-flow variables (as described in previous sections of this specification) may also have utility in this regard.

Example 6

Assessment of Esophageal Motor Function with Respect to the Pressure-Flow Variables Zn and ZPp, and Analysis of their Utility as Markers of Obstruction In an evaluation of further pressure-flow variables useful for assessing swallowing motor function, the inventor hypothesised that particular impedance measurements could be used to derive diagnostically meaningful information on oesophageal function through a comparison of the impedance signals measured during bolus flow prior to the oesophageal contractile wave with impedance signals measured during the oesophageal contractile wave. Specifically this method relies upon the nadir of impedance preceding the pressure peak (Zn) and the impedance at the time of pressure peak (ZPp).

Figure 19:
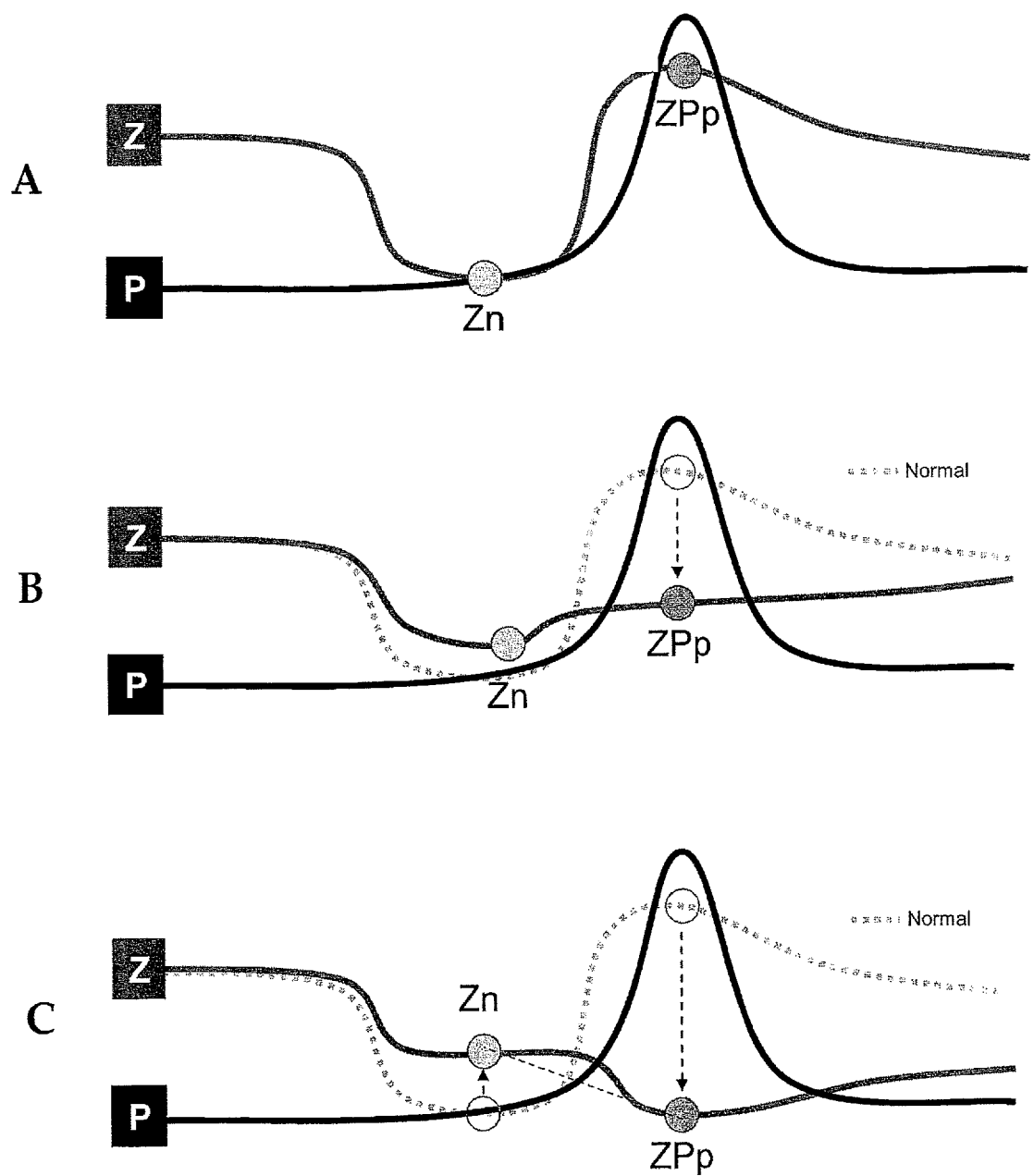
FIG. 19 provides a series of representative graphs which show impedance (Z) and pressure (P) measurements (represented as respective waveforms) derived from the passage of a bolus from the mouth to the esophagus of a subject.

During a normal effective swallow, ZPp exceeds Zn by several fold as shown in FIG. 19A. An ineffective swallow is defined when a bolus fails to clear the esophageal lumen. When this occurs, the impedance signal remains low because bolus residue acts as a conductor for current flow between luminal electrodes. During an ineffective swallow, ZPp approaches Zn as shown in FIG. 19B. A further iteration of this concept is one where the oesophageal lumen is physically obstructed, either due to a zone of narrowing, or due to reduced luminal compliance which reduces the degree to which the lumen can distend/stretch to accommodate passage of a bolus. When this occurs, the reduced cross-sectional area increases the value of Zn such that ZPp drops to below Zn. This is due to the presence of residue and the fact that the oesophageal contractile wave 'bares down' upon the impedance segment with much greater force than normal. Hence a Zn/ZPp>1 is a maker of obstruction over ineffective swallow as shown in FIG. 19C.

Figure 20:
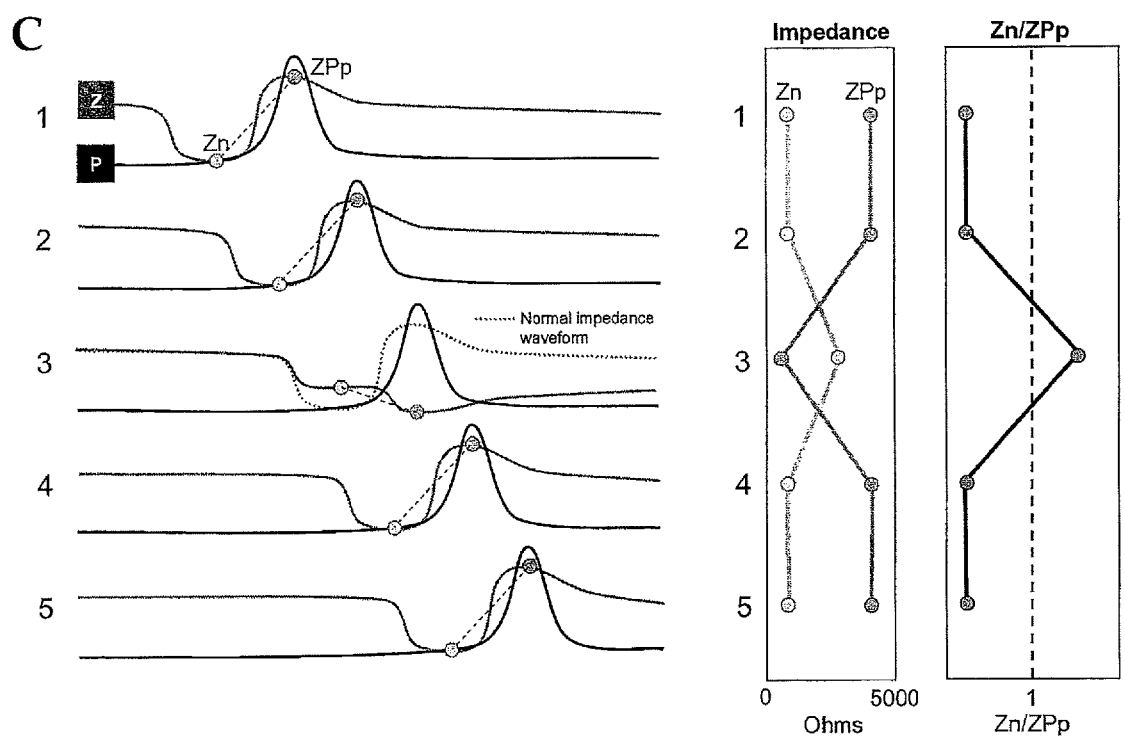
FIG. 20 provides a series of representative graphs which show impedance (Z) and pressure (P) measurements (represented as respective waveforms in the left hand side of the figure) derived from five locations (1-5) along the length of the lumen as a bolus passes from the mouth to the esophagus of a subject. The boxed sections on the right of the figure show impedance values for Zn and ZPp (measured in Ohms) at each of the five locations, and the value of Zn/ZPp at each of the five locations.

The inventor hypothesised that the value of Zn and ZPp and the relationship of Zn/ZPp may be simple markers of oesophageal function/dysfunction. These variables are easily derived by automated analysis and axial location of the maximum Zn, minimum ZPp and maximum Zn/ZPp may identify the position of an abnormality. This concept is shown in FIGS. 20A-20C where impedance and pressure measurements taken from varying positions distal to the esophago-gastric junction (positions 1-5) are shown. In a normal swallow (FIG. 20A), Zn and ZPp measurements are expected to be consistent at each position such that the Zn/ZPp ratio remains below 1. In an individual with an ineffective swallow that is not due to an obstruction (FIG. 20B), the Zn value at the position of the ineffective swallow (position 3) is expected to increase in comparison to positions 1, 2, 4 and 5 where swallowing motor function is normal. Similarly, the ZPp value at position 3 is expected to approach the Zn value (i.e. decrease) in comparison to positions 1, 2, 4 and 5. As a result, the Zn/ZPp ratio approaches 1. In an individual whose ineffective swallow is due to an obstruction (FIG. 20C), the ZPp value at the position of the obstruction (position 3) is expected to fall below the Zn value at that position. As a result, the Zn/ZPp ratio at the position of the obstruction is greater than 1. This hypothesis was confirmed in the following study.

Methods

Fifteen healthy adults (5 M, mean age 33 yrs (20-48) and 15 non-obstructive dysphagia patients were investigated with a combined impedance perfusion manometry catheter incorporating 7 impedance segments (2 cm spaced) and 22 side hole sensors (sensors adjacent impedance array at 2 cm). The catheter was placed with the most distal impedance segment 2 cm proximal to the EGJ junction. Subjects swallowed 5×2 cm and 5×4 cm solid boluses.

Figure 21:
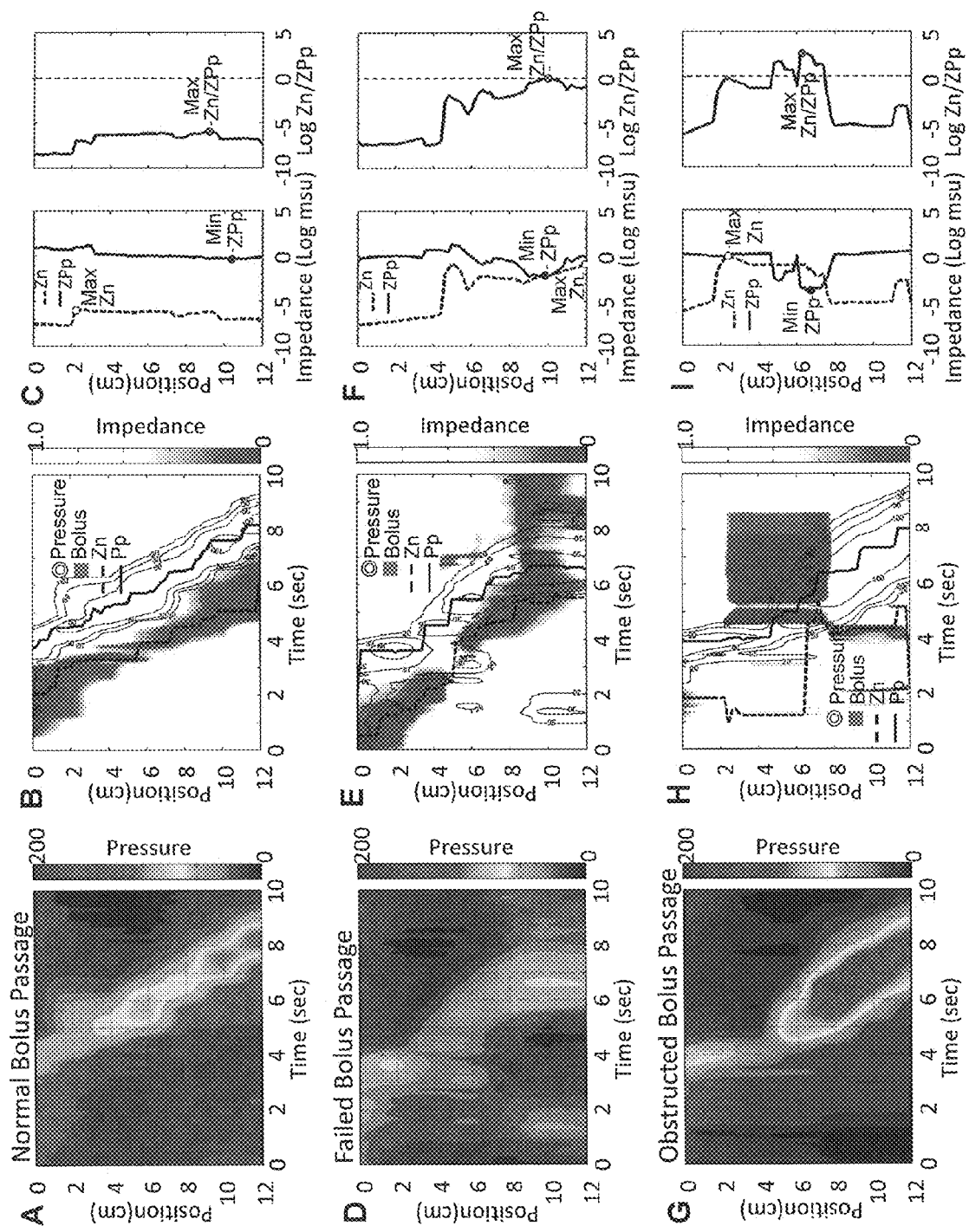
FIG. 21 provides results obtained from the analysis methods used in the study described in Example 6. Subjects with normal swallowing (A-C), failed (ineffective) esophageal bolus passage (D-F) and obstructed bolus passage due to aortic arch compression of the esophagus (G-I) are shown. A, D and G show iso-contour plots of pressures generated during the swallow. B, E and H show pressure-impedance iso-contour plots with pressure as lines (20, 30 and 50 mmHg iso-contours) and impedance superimposed (purple iso-contour showing impedance levels <0.5 msu). The timings of Zn and ZPp are marked at all positions down the plots. Note that in E and H, retention of the bolus within the esophageal lumen after the peristaltic wave has passed is indicated by the impedance iso-contour which remains <0.5 msu (purple shading). C, F and I show graphs of values of Zn, ZPp and Zn/ZPp at all positions down the plots. Note that these real in-vivo recordings mirror the changes in Zn, ZPp and Zn/ZPp previously described in FIG. 20, whereby ineffective bolus passage (F in this Figure, B in FIG. 20) is indicated by an increase in Zn and decrease in ZPp and obstructed bolus passage (I in this Figure, C in FIG. 20) is indicated when Zn exceeds ZPp (i.e. Zn/ZPp>1).

Using commercially available software (Medical Measurement Systems Inc) pressure-impedance recordings were analysed for standard measures; there were total bolus transit time (TBTT), mean bolus presence time (BPT), distal contractile integral (DCI), size of the 30 mmHg isocontour defect (cm<30ICP). Exported text files of swallows (30 sec at 20 Hz) were also analysed using our new methods (as per Example 4). Impedance data were standardised to the median for each channel (presented as median standardised units, msu) and analysed objectively using a MATLAB-based algorithms. The new approach to analysis of pressure-impedance recordings was used to derive pressure-flow variables as detailed in Example 4 (i.e. PNadImp, PeakP, mIBP and TNadImp-PeakP). In addition, changes in the nadir impedance preceding peak pressure (Zn), impedance at the time of peak pressure (ZPp), and the obstructive index (Zn/ZPp), were recorded in association with bolus flow along the oesophageal body (see FIG. 21).

Results 150 control and 150 patient solid bolus swallows were analysed. Results are shown in Table 7. Of standard pressure-impedance measures, only the 30 mmHg iso-contour defect was altered in patients compared to controls.

TABLE 7

|  | CONTROL | PATIENT |
|---|---|---|
| Standard Pressure only and Impedance only Variables | | |
| TBTT | 10.1 | 14.1 |
| Sec | [9.6, 12.4] | [9.6, 12.4] |
| Mean BPT | 7.7 | 10.3 |
| Sec | [4.7, 10.1] | [8.5, 11.2] |
| DCI | 1465 | 1279 |
| mmHg | [1206, 2016] | [648, 2441] |
| cm < 30ICP | 0.8 | 3.4* |
|  | [0, 2.1] | [1.2, 4.4] |
| Pressure-Impedace Pressure-Flow Variables | | |
| Mean Peak P mmHg | 46 | 83* |
|  | [42, 71] | [57, 91] |
| PNadImp | 9 | 8 |
|  | [7, 12] | [6, 11] |
| Mean IBP mmHg | 13 | 14 |
|  | [11, 15] | [6, 18] |
| Mean TNadImp-PeakP sec | 2.6 | 2.6 |
|  | [2.3, 2.7] | [2.4, 3.1] |
| Pressure Guided Impedance Variables | | |
| Mean Log Zn | −1.9 | −0.9*** |
|  | [−2.6, −1.4] | [−1.2, −0.8] |
| Max Log Zn | −4.8 | −1.3*** |
|  | [−5.2, −4.0] | [−2.7, 0.7] |
| Min Log ZPp | −0.6 | −1.5** |
|  | [−1.2, −0.5] | [−1.7, −1.2] |
| Max Log Zn/ZPp | −5.1 | −0.8*** |
|  | [−5.4, −3.7] | [−1.8, 0.2] |

Data expressed as median (IQR).
*Mann-Whitney Rank Sum Test *p < 0.050, p < 0.005, *p < 0.001.

Figure 22:
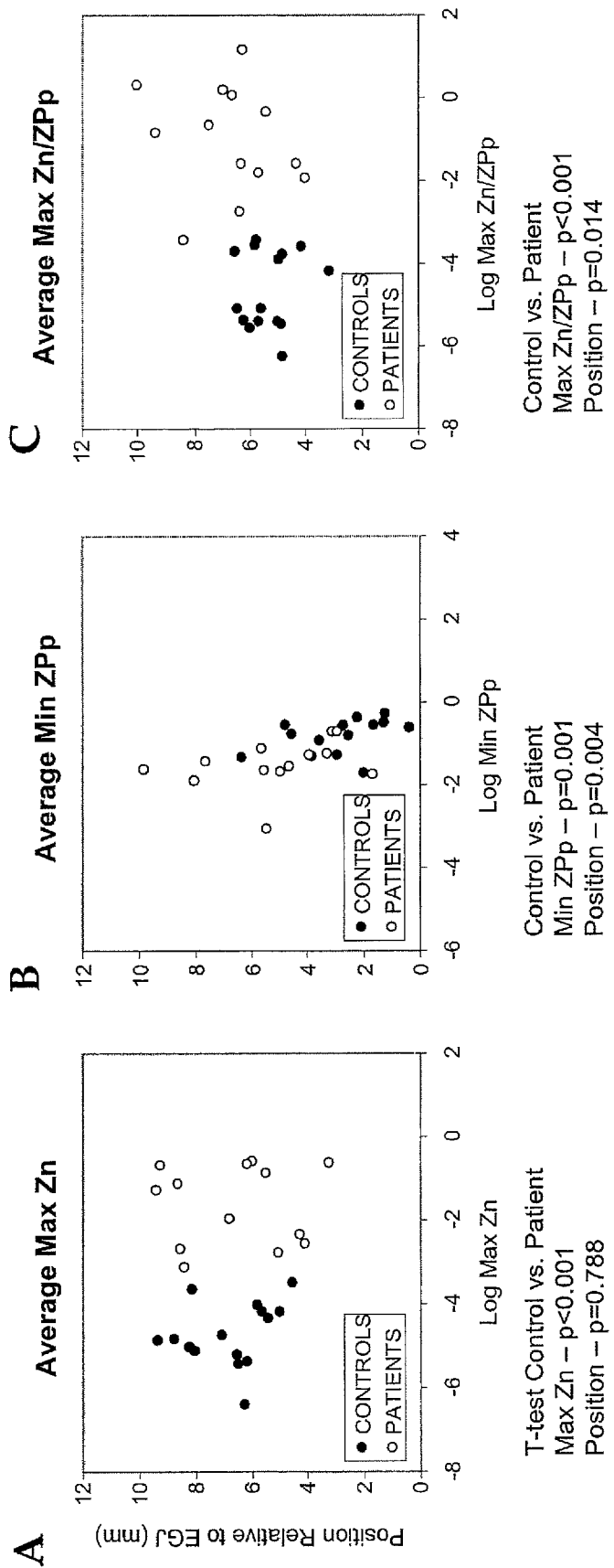
FIG. 22 provides a series of scatter plots of mean values for Zn max, ZPp max and Zn/ZPp max obtained from 15 control subjects and 15 patients with non-obstructive dysphagia who demonstrated no evidence of obstruction on endoscopy and/or video fluoroscopy. (A) shows the average value of each subject/patient and average position of the max Zn value relative to the Oesophago-Gastric Junction (EGJ). (B) shows the average value of each subject/patient and average position of the min ZPp value relative to the Oesophago-Gastric Junction. (C) shows the average value of each subject/patient and average position of the max Zn/ZPp value relative to the Oesophago-Gastric Junction. Note that in C four patients actually had a Zn/ZPp of >1 (Log Zn/ZPp>0) which is suggestive of obstruction, even though obstruction was not detected using the standard tests.

Of pressure-flow variables peak pressure was significantly lower in patients compared to controls (Table 7). In contrast, all impedance only variables based were significantly altered in patients compared to controls, also with great statistical confidence. The data for value and axial position of max Zn, min ZPp and max Zn/ZPp along the esophagus for each individual studied are shown in FIG. 22. There was complete separation of controls and patients based on the value of maxZn, however this variable alone did not differentiate the patients based on the position of the abnormality (FIG. 22A). In contrast, min ZPp was significantly lower in value in patients and the position of the min ZPp was localised significantly more proximally (higher in the esophagus) (FIG. 22B) as was the position of Zn/ZPp (FIG. 22C).

CONCLUSIONS

These data show that patients with non-obstructive dysphagia can also be differentiated from controls using pressure-guided impedance variables (Zn, ZPp). Whilst it has been demonstrated that standard pressure only variables, impedance only variables and pressure-impedance pressure-flow variables are altered, and can be used to assess swallowing motor function, the greater statistical confidence of differences in Zn and ZPp suggests that these variables are ideal predictors of pharyngeal and/or esophageal dysfunction. In addition, ZPp appears to be a marker of the location of dysfunction. Hence the ratio of Zn/ZPp provides a reliable index of both the degree of pharyngeal and/or esophageal dysfunction as well as the location of the dysfunction. We predict that a Zn/ZPp of >1 is a marker of physical obstruction, and this may allow for targeted intervention to the location of the dysfunction. Alternatively, circumstances of dysphagia symptoms without an abnormal Zn/ZPp would suggest that the problem may be localised elsewhere, function obstruction of the esophago-gastric junction, to give one example.

Example 7

Figure 23:
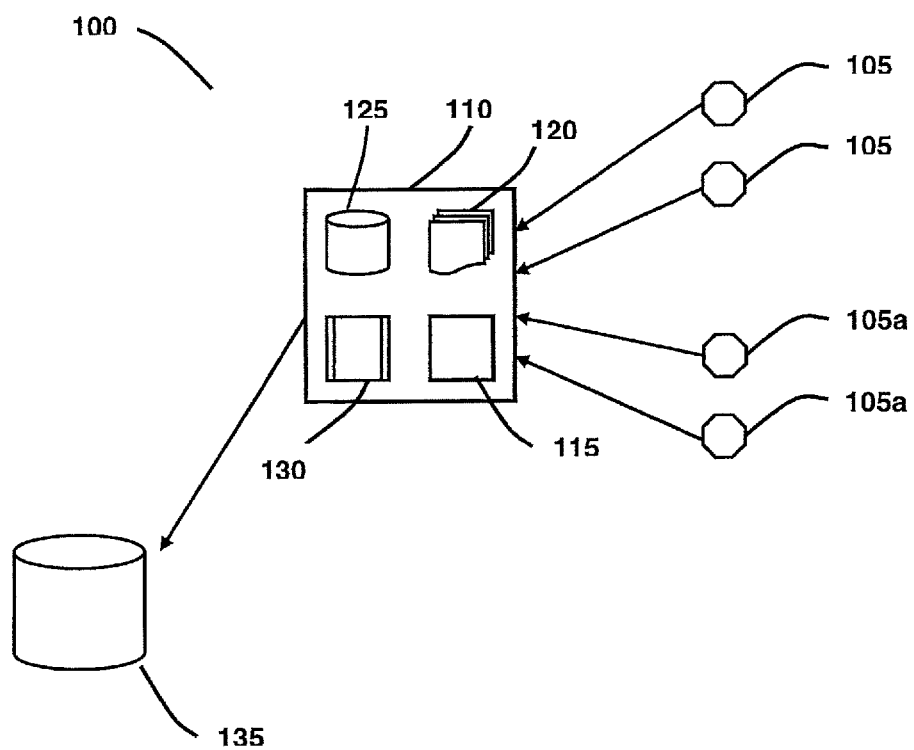
FIG. 23 is a schematic diagram of an apparatus according to an embodiment of the present invention.

Apparatus and Software for Enabling an Assessment of Swallowing Motor Function in a Subject The methods of the present invention, as described above, can be performed in any manner of means as would be understood by a person skilled in the art. For example, with reference to FIG. 23 there is shown an example apparatus 100 for enabling an assessment of swallowing motor function in a subject according to a sixth aspect of the invention.

The apparatus 100 communicates with or includes one or more sensors 105,105a which measure intraluminal impedance and pressure changes, respectively, in the pharynx and/or esophagus of a subject (not shown) during clearance of a bolus from the mouth and/or throat of the subject. In addition and/or as an alternative to the one or more sensors 105,105a, a server 135 containing intraluminal impedance measurements and pressure measurements previously taken from a subject may be provided, said server 135 being in communication with the apparatus 100.

The apparatus 100 may for example include a computer 110 which is in communication with the one or more sensors 105,105a, and/or with the server 135. The computer 110 receives and processes measurements obtained by the one or more sensors 105,105a or from intraluminal impedance and pressure measurements previously taken from the subject and stored on the server 135. The computer 110 includes a processor 115 for processing and computing various signals received from the one or more sensors 105,105a, or from previously obtained measurements stored on the server 135, and software to carry out these functions. The software will be described further with reference to FIG. 24.

The computer 110 may also include a memory 120 for storing data temporarily and running software. A database 125 may be included to store measurements obtained by the one or more sensors 105,105a. The computer 110 may also include a display 130 for displaying data processed by the processor 115.

It will be appreciated that the computer 110 may be any one or more of a desktop computer, portable computer, tablet or mobile communication device. The server 135 may be directly connected to the computer 110 or may be connected over a local area network or a network such as the Internet so that the server 135 may be at a remote location. The computer 110 can retrieve intraluminal impedance and pressure measurements previously obtained, as required, and store the measurements on the database 125 or on the server 135, as required.

The one or more sensors 105 measure intraluminal impedance and this may be measured in any suitable way, as would be understood by a person skilled in the art, and as previously described in detail above. For example, the one or more sensors 105 may be electrodes which are longitudinally spaced on a narrow indwelling catheter, as described above. When placed in the pharynx and/or esophagus of a subject, the electrodes are in electrical contact with the luminal mucosa. A high frequency electrical current is applied through consecutively connected impedance electrode pairs. The spaces between electrodes form linear segments along the catheter. The impedance to current flow for each segment is measured and stored in the memory 120 or on the database 125 in a sequential scan cycle fast enough to capture the impedance change along the catheter during a swallow accurately.

Preferably, impedance measurements obtained by the one or more sensors 105 are captured electronically and recorded by the apparatus 100. Impedance patterns may be analysed by the processor 115 through the visual detection of the occurrence of impedance drops.

The one or more sensors 105a measure intraluminal pressure changes and these may be measured in any suitable way, as would be understood by a person skilled in the art, and as previously described in detail above. For example, the one or more sensors 105a may form part of an indwelling catheter with pressure changes due to bolus passage being measured and stored in the memory 120 or on the database 125 of the computer 110.

In some embodiments, both pressure and impedance measurements can be obtained simultaneously by providing a single catheter which incorporates the impedance electrodes and pressure sensors.

In the operation of one embodiment, the one or more sensors 105,105a communicate with the computer 110, which receives the impedance and pressure information from the one or more sensors 105,105a, and combines and analyses this information via encoded instructions to derive a value for one or more pressure flow variables in order to assess swallowing motor function in the subject. Details with respect to analysis of combined impedance and pressure measurements and derivation of a value for one or more pressure flow variables is described in detail above. It will be clearly understood that in an alternative embodiment, impedance and pressure measurements that have previously been obtained from a subject may be received by the computer 110 from data which has been stored either on the database 125 or obtained via the server 135. Analysis of the data stored on the database 125, obtained via the server 135, or obtained directly from the sensors 105,105a may be carried out in hardware (such as on a processor 115) or software running in the memory 120.

Figure 24:
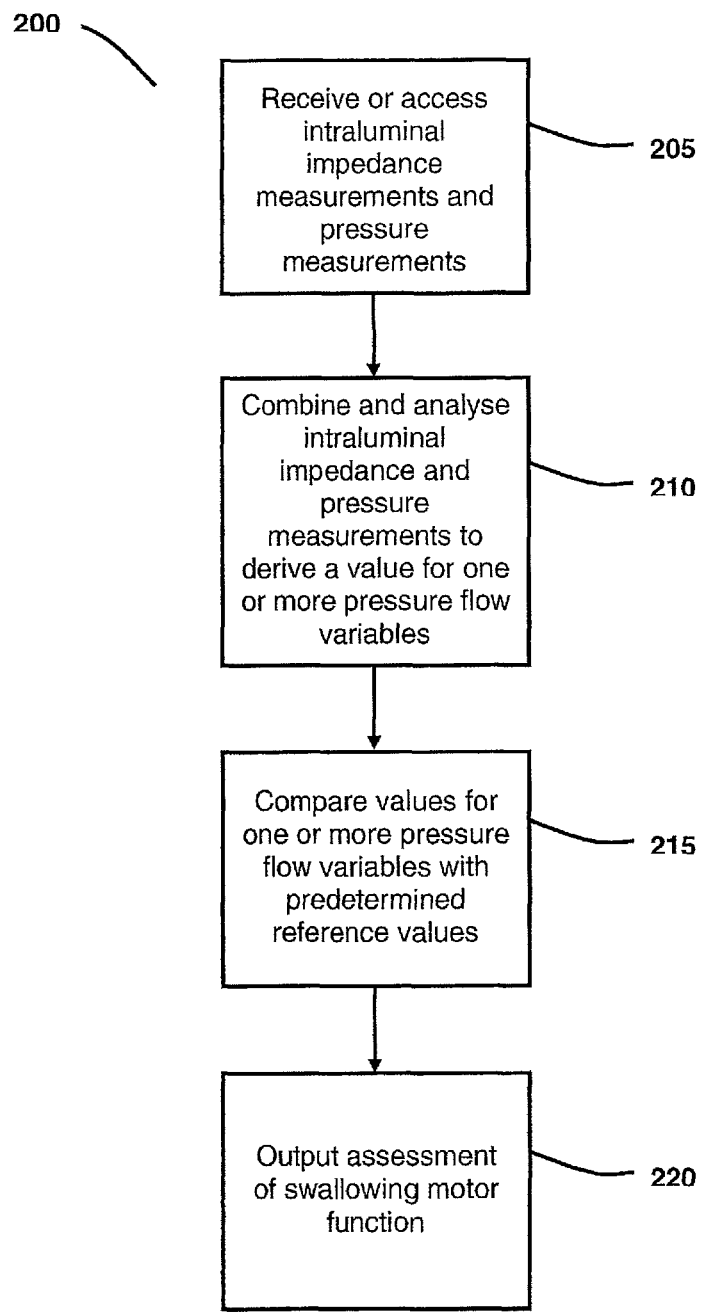
FIG. 24 is a flow diagram of a method for assessing swallowing motor function in a subject according to a first aspect of the present invention.

FIG. 24 describes a method 200 for assessing swallowing motor function in a subject according to a first aspect of the present invention. In this embodiment, the method 200 is carried out by the computer 110 or on software running in the memory 120. At step 205 intraluminal impedance measurements and pressure measurements obtained from the pharynx and/or esophagus of a subject during clearance of a bolus from the mouth and/or throat of the subject are accessed or received. As indicated above, this may be done in real-time from a subject via the one or more sensors 105,105a and a computer 110, as also discussed with reference to FIG. 23. Alternatively, data can be accessed or received from the database 125 or the server 135 which contains impedance and pressure measurements that have previously been obtained from a subject. Control then moves to step 210 where the intraluminal impedance and pressure measurements are combined and analysed to derive a value for one or more pressure-flow variables in the pharynx and/or esophagus of the subject. This step may be carried out by the processor 115 on the computer 110. Control then moves to step 215 where swallowing motor function in the subject is assessed by performing a comparison between the value of the one or more pressure-flow variables with a predetermined pharyngeal and/or esophageal reference value for the one or more pressure-flow variables. The comparison may be carried out by the processor 115 on the computer 110. The predetermined pharyngeal and/or esophageal reference value for the one or more pressure-flow variables may be stored in the database 125, on the server 135, and/or in the memory 120 of the computer 110. Finally, at step 220 an assessment of swallowing motor function in the subject on the basis of comparison is provided as an output. The assessment is preferably displayed on the display 130 of the computer 110 and/or stored on the database 125 or the server 135.

The method 200 may further include the step of providing an alert via display 130 if ineffective swallowing in the subject on the basis of the comparison is identified. In addition, the method 200 may further include the step of determining and outputting via the display 130 the risk of aspiration in the subject, a diagnosis of an increased likelihood of aspiration in the subject, a prediction of aspiration in the subject, and/or identifying that the subject is susceptible to aspiration. Alternatively, or in addition, the method 200 may include the step of determining and outputting via the display 130 a prediction for the occurrence of dysphagia in the subject following therapy and/or surgery. Alternatively, or in addition, the method 200 may include the step of generating a swallow risk index, a dysphagia risk index and/or an obstructive risk index. Alternatively, or in addition, the method 200 may include the step of determining the location of an obstruction which is causing ineffective swallowing.

Figure 25:
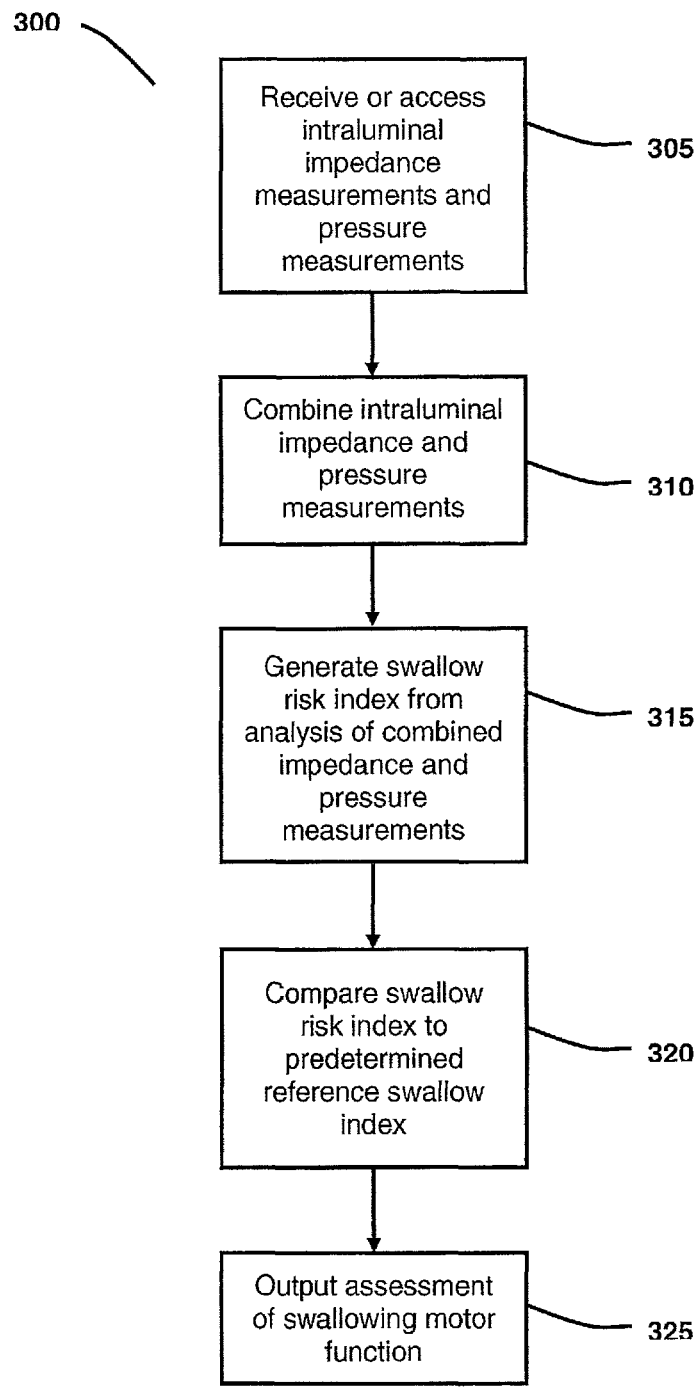
FIG. 25 is a flow diagram of a method for assessing swallowing motor function in a subject according to a second aspect of the present invention.

FIG. 25 describes a method 300 for assessing swallowing motor function in a subject according to a second aspect of the present invention. In this embodiment, the method 300 is carried out by the computer 110 or on software running in the memory 120. At step 305 intraluminal impedance measurements and pressure measurements obtained from the pharynx esophagus of a subject during clearance of a bolus from the mouth and/or throat of the subject are accessed or received. As indicated above, this may be done in real-time from a subject via the one or more sensors 105,105a and a computer 110, as also discussed with reference to FIG. 23. Alternatively, data can be accessed or received from the database 125 or the server 135 which contains impedance and pressure measurements that have previously been obtained from a subject. Control then moves to step 310 where the intraluminal impedance and pressure measurements are combined. This step may be carried out by the processor 115 on the computer 110. Control then moves to step 315 where a swallow risk index for the subject is generated based on a combination of a value of more than one pressure-flow variable in the pharynx and/or esophagus of the subject, wherein the value is derived from an analysis of the combined intraluminal impedance and pressure measurements. This step may be carried out by the processor 115 on the computer 110. Control then moves to step 320 where swallowing motor function in the subject is assessed by performing a comparison between the swallow risk index for the subject to a predetermined reference swallow index. The comparison may be carried out by the processor 115 on the computer 110. The predetermined reference swallow index may be stored in the database 125, on the server 135, and/or in the memory 120 of the computer 110. Finally, at step 325 an assessment of swallowing motor function in the subject on the basis of the comparison is provided as an output. The assessment is preferably displayed on the display 130 of the computer 110 and/or stored on the database 125 or the server 135.

The method 300 may further include the step of providing an alert via display 130 if ineffective swallowing in the subject on the basis of the comparison is identified. In addition, the method 300 may further include the step of determining and outputting via the display 130 the risk of aspiration in the subject, a diagnosis of an increased likelihood of aspiration in the subject, a prediction of aspiration in the subject, and/or identifying that the subject is susceptible to aspiration. Alternatively, or in addition, the method 200 may include the step of determining and outputting via the display 130 a prediction for the occurrence of dysphagia in the subject following therapy and/or surgery. Alternatively, or in addition, the method 200 may include the step of generating a dysphagia risk index.

Figure 26:
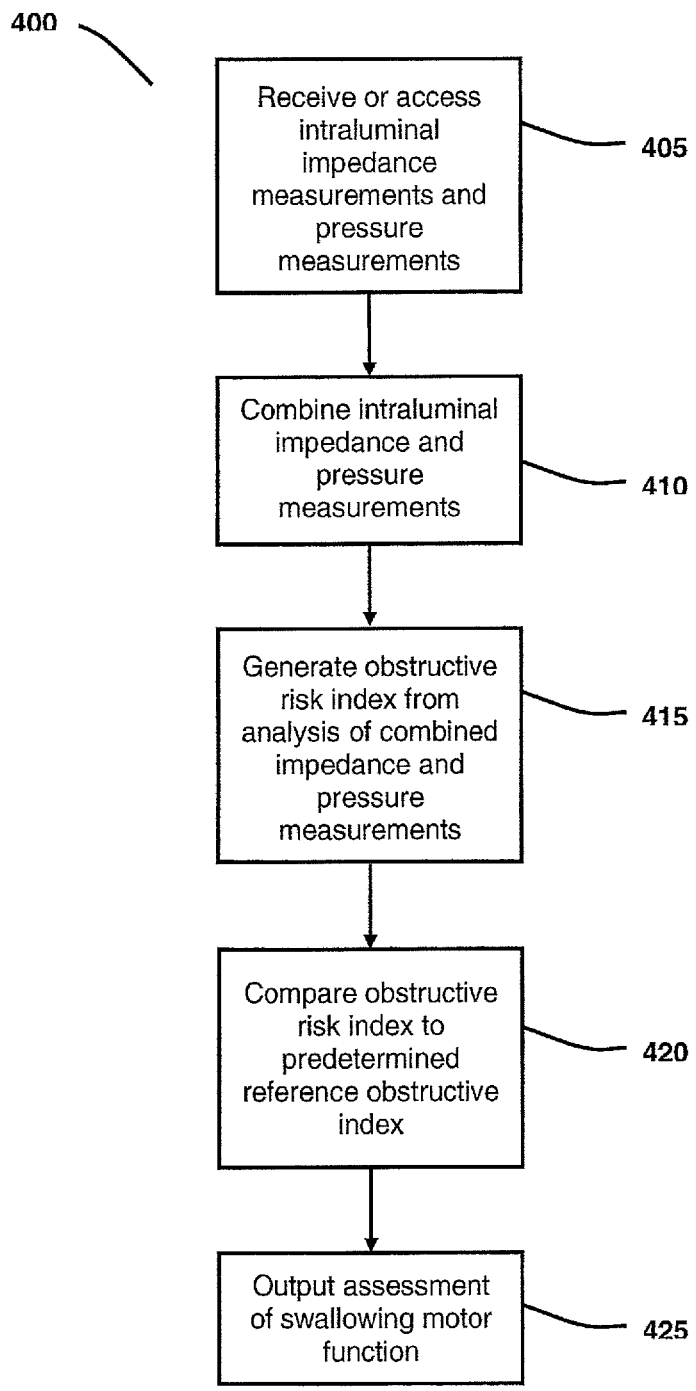
FIG. 26 is a flow diagram of a method for assessing swallowing motor function in a subject according to a third aspect of the present invention.

FIG. 26 describes a method 400 for assessing swallowing motor function in a subject according to a third aspect of the present invention. In this embodiment, the method 400 is carried out by the computer 110 or on software running in the memory 120. At step 405 intraluminal impedance measurements and pressure measurements obtained from the pharynx and/or esophagus of a subject during clearance of a bolus from the mouth and/or throat of the subject are accessed or received. As indicated above, this may be done in real-time from a subject via the one or more sensors 105,105a and a computer 110, as also discussed with reference to FIG. 23. Alternatively, data can be accessed or received from the database 125 or the server 135 which contains impedance and pressure measurements that have previously been obtained from a subject. Control then moves to step 410 where the intraluminal impedance and pressure measurements are combined. This step may be carried out by the processor 115 on the computer 110. Control then moves to step 415 where an obstructive risk index for the subject is generated based on a combination of a value of more than one pressure-flow variable in the pharynx and/or esophagus of the subject, wherein the value is derived from an analysis of the combined intraluminal impedance and pressure measurements. This step may be carried out by the processor 115 on the computer 110. Control then moves to step 420 where swallowing motor function in the subject is assessed by performing a comparison between the obstructive risk index for the subject to a predetermined reference obstructive index. The comparison may be carried out by the processor 115 on the computer 110. The predetermined reference obstructive index may be stored in the database 125, on the server 135, and/or in the memory 120 of the computer 110. Finally, at step 425 an assessment of swallowing motor function in the subject on the basis of the comparison is provided as an output. The assessment is preferably displayed on the display 130 of the computer 110 and/or stored on the database 125 or the server 135. The method 400 may further include the step of providing an alert via display 130 if ineffective swallowing in the subject on the basis of the comparison is identified.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

What is claimed:

1. A method for treating a subject having ineffective swallowing motor function or at risk of aspiration, the method including:
   passing a bolus through the pharynx, the esophagus, or a combination of the pharynx and esophagus of the subject;
   measuring intraluminal impedance and pressure in the pharynx, the esophagus, or a combination of the pharynx and esophagus, of the subject during clearance of the bolus from the mouth, the throat, or a combination of the mouth and the throat, of the subject;
   accessing intraluminal impedance measurements and pressure measurements obtained from the pharynx, the esophagus, or a combination of the pharynx and esophagus, of the subject during clearance of a bolus from the mouth, the throat, or a combination of the mouth and the throat, of the subject;
   generating an impedance waveform of the bolus clearance from the intraluminal impedance measurements;
   generating a pressure waveform of the bolus clearance from the pressure measurements;
   combining and analyzing the intraluminal impedance measurements and pressure measurements, wherein the intraluminal impedance measurements are used to guide analysis of the pressure measurements;
   deriving values for pressure-flow variables identified by combining and analyzing the intraluminal impedance measurements and pressure measurements, wherein the pressure-flow variables include:
      duration in the drop in intraluminal impedance during bolus clearance (Flow Interval);
      intraluminal distention pressure at the nadir of an impedance waveform (PNadImp);
      peak pressure of a pressure waveform (PeakP); and
      time from the nadir of the impedance waveform to a peak pressure of the pressure waveform (TNadImp-PeakP);
   generating a value for a swallow risk index for the subject, wherein the swallow risk index has the following formula:

$$\frac{(\text{Flow Interval} \times PNadImp)}{(PeakP \times (PNadImp - PeakP + 1))} \times 100$$

assessing swallowing motor function in the subject by comparing the generated swallow risk index value with a predetermined reference swallow risk index value; and
   when the swallow risk index value of the subject is higher than a predetermined reference swallow risk index value treating the subject to alleviate ineffective swallowing and/or aspiration.

2. The method according to claim 1, wherein if the value of PNadImp in the subject is higher than a predetermined PNadImp reference value, treating the subject comprises one or more of dilatation, myotomy and botox.

3. A method for treating a subject having ineffective swallowing motor function or at risk of aspiration, the method including:
   passing a bolus through the pharynx, the esophagus, or a combination of the pharynx and esophagus of the subject;
   measuring intraluminal impedance and pressure in the pharynx, the esophagus, or a combination of the pharynx and esophagus, of the subject during clearance of the bolus from the mouth, the throat, or a combination of the mouth and the throat, of the subject;
   accessing intraluminal impedance measurements and pressure measurements obtained from the pharynx, the esophagus, or a combination of, the pharynx and esophagus, of the subject during clearance of a bolus from the mouth, the throat, or the mouth and throat, of the subject;

generating an impedance waveform of the bolus clearance from the intraluminal impedance measurements;

generating a pressure waveform of the bolus clearance from the pressure measurements;

combining and analyzing the intraluminal impedance measurements and pressure measurements, wherein the intraluminal impedance measurements are used to guide analysis of the pressure measurements;

deriving values for pressure-flow variables identified by combining and analyzing the intraluminal impedance measurements and pressure measurements, wherein the pressure-flow variables include:

intrabolus pressure (IBP);

intrabolus pressure slope (IBP slope); and time from the nadir of the impedance waveform to a peak pressure of the pressure waveform (TNadImp-PeakP);

generating a value for a dysphagia risk index for the subject, wherein the dysphagia risk index has the following formula:

$$IBP \times IBP\ Slope \times (TNadImp\text{-}PeakP)^{-1}$$

assessing swallowing motor function in the subject by comparing the generated dysphagia risk index value with a predetermined reference dysphagia risk index value; and when the dysphagia risk index value of the subject is higher than a predetermined reference dysphagia risk index treating the subject to alleviate ineffective swallowing and/or aspiration.

4. The method according to claim 1, wherein a value for a further pressure-flow variables is derived, wherein the pressure-flow variable is the nadir of the impedance waveform preceding peak pressure (Zn) in the pharynx, in the esophagus, or in a combination of the pharynx and esophagus, of the subject, and wherein when, the subject's Zn value is higher than a predetermined Zn reference value treating the subject to alleviate ineffective swallowing and/or aspiration.

5. A method for identifying a location of an obstruction in the pharynx, in the esophagus, or in a combination of the pharynx and esophagus, of a subject having ineffective swallowing motor function, the method including:

passing a bolus through the pharynx, the esophagus, or a combination of the pharynx, and esophagus of the subject;

measuring intraluminal impedance and pressure in the pharynx, the esophagus, or a combination of the pharynx and esophagus, of the subject during clearance of the bolus from the mouth, the throat, or a combination of the mouth and the throat, of the subject;

generating an impedance waveform of the bolus clearance from measurements of intraluminal impedance;

generating a pressure waveform of the bolus clearance from measurements of pressure;

combining and analyzing measurements of intraluminal impedance and measurements of pressure, wherein the measurements of intraluminal impedance are used, to guide analysis of the measurements of pressure, and wherein the measurements of pressure are used to guide analysis of the measurements of intraluminal impedance;

deriving values for pressure-flow variables identified by combining and analyzing the measurements of intraluminal impedance and measurements of pressure, wherein a value for at least one of the pressure-flow variables is derived from identifying the nadir of the impedance waveform (NadImp), wherein NadImp is a time marker to plot intraluminal distension pressure, and wherein the pressure-flow variables include:

nadir of the impedance waveform preceding peak pressure (Zn); and impedance at the time of peak pressure of the pressure waveform (ZPp), wherein the position of the maximum $$Zn/ZPp$$

in the subject is indicative of the location of the obstruction.

6. The method according to claim 3, wherein treating the subject comprises one or more of dilatation, myotomy and botox.

7. The method according to claim 3, wherein a value for a further pressure-flow variable is derived, wherein the pressure-flow variable is the nadir of the impedance waveform preceding peak pressure (Zn) in the pharynx, in the esophagus, or in a combination of the pharynx and esophagus, of the subject, and wherein when the value of Zn in the subject is higher than a predetermined Zn reference value treating the subject to alleviate ineffective swallowing and/or aspiration.

8. The method according to claim 7, wherein heating the subject comprises one or more of dilatation, myotomy and botox.

9. The method according to claim 4, wherein treating the subject comprises one or more of dilatation, myotomy and botox.

10. The method according to claim 5, further comprising treating the obstruction by one or more of dilatation, myotomy and botox.

11. The method according to claim 5, further comprising the steps of:

preparing an obstructive index plot indicative of an obstructed zone in the pharynx, the esophagus, or a combination of the pharynx and esophagus, of the subject;

deriving values for pressure-flow variables identified by combining and analyzing the measurements of intraluminal impedance and measurements of pressure, wherein the pressure-flow variables include:

time from the nadir of the impedance waveform to a peak pressure of the pressure waveform (TNadImp-PeakP); and nadir of the impedance waveform (NadImp), wherein the highest ratio of NadImp/(TNadImp-PeakP) in the subject corresponds to the obstructed, zone.

\* \* \* \* \*